(12) United States Patent
Flickinger

(10) Patent No.: US 11,975,164 B2
(45) Date of Patent: *May 7, 2024

(54) NASAL DRUG DELIVERY DEVICE AND METHOD OF MAKING SAME

(71) Applicant: Monaghan Medical Corporation, Plattsburgh, NY (US)

(72) Inventor: William J. Flickinger, Medina, OH (US)

(73) Assignee: MONAGHAN MEDICAL CORPORATION, Plattsburgh, NY (US)

(*) Notice: Subject to any disclaimer, the term of this patent is extended or adjusted under 35 U.S.C. 154(b) by 967 days.

This patent is subject to a terminal disclaimer.

(21) Appl. No.: 16/875,763

(22) Filed: May 15, 2020

(65) Prior Publication Data

US 2021/0030711 A1 Feb. 4, 2021

Related U.S. Application Data

(63) Continuation of application No. 15/263,233, filed on Sep. 12, 2016, now Pat. No. 10,682,331, which is a
(Continued)

(51) Int. Cl.
*A61M 11/06* (2006.01)
*A61K 9/00* (2006.01)
(Continued)

(52) U.S. Cl.
CPC .......... *A61M 3/025* (2013.01); *A61K 9/0043* (2013.01); *A61K 31/351* (2013.01); *A61K 38/14* (2013.01);
(Continued)

(58) Field of Classification Search
CPC ...... A61M 11/06; A61M 11/08; A61M 15/00; A61M 15/0028; A61M 15/003;
(Continued)

(56) References Cited

U.S. PATENT DOCUMENTS 59,562 A 11/1866 Cutter
258,632 A 5/1882 Cooper
(Continued)

FOREIGN PATENT DOCUMENTS

EP 1941927 7/2008
GB 2327223 1/1999
(Continued)

OTHER PUBLICATIONS

Husen et al., "Nasal Airway and CPAP Outcomes," Sleep Apnea Research Group, Washington University, School of Public Health and Community Medicine, located at http://depts.washington.edu/ccor/studies/SleepApnea/Nasal_AinNay_and_CPAP_Outcome, printed on Nov. 30, 2012, 5 pages.
Manes, R. Peter et al. "Prospective Evaluation of Aerosol Delivery by a Powered Nasal Nebulizer in the Cadaver Model" International Forum of Allergy & Rhinology, vol. 1, No. 5, Sep./Oct. 2011, pp. 366-371.
(Continued)

*Primary Examiner* — Margaret M Luarca
(74) *Attorney, Agent, or Firm* — Crowell & Moring LLP

(57) ABSTRACT

A drug delivery device capable of forming a medicated mist that reaches the nasal and paranasal sinus cavities contains a puncturing element within its canister. The puncturing element is used in combination with a compartment that contains a filling. The compartment is optionally detachable from an interior of the device or entirely separate from the device. The puncturing element punctures the compartment, releasing the filling into the reservoir of the device to provide a medicated liquid. The device may store any form of medication so long as the medication remains stable. When dry powder forms are desired, the reservoir and/or compartment may be filled with a solution or diluent so as to form the medicated liquid, which may then be dispensed as a mist through the device following the puncturing.

20 Claims, 35 Drawing Sheets

Related U.S. Application Data continuation-in-part of application No. 15/225,465, filed on Aug. 1, 2016, now abandoned, which is a continuation-in-part of application No. 14/295,502, filed on Jun. 4, 2014, now abandoned, which is a continuation-in-part of application No. 13/404,623, filed on Feb. 24, 2012, now Pat. No. 9,440,020.

(51) Int. Cl.

| | | |
|---|---|---|
| *A61K 31/351* | (2006.01) | |
| *A61K 38/14* | (2006.01) | |
| *A61M 3/02* | (2006.01) | |
| *A61M 15/08* | (2006.01) | |
| *A61M 16/00* | (2006.01) | |

(52) U.S. Cl.
CPC .......... *A61M 3/0279* (2013.01); *A61M 11/06* (2013.01); *A61M 15/08* (2013.01); *A61M 16/0063* (2014.02); *A61M 2202/064* (2013.01); *A61M 2205/07* (2013.01); *A61M 2205/276* (2013.01); *A61M 2205/3553* (2013.01); *A61M 2205/3584* (2013.01); *A61M 2205/3592* (2013.01); *A61M 2205/50* (2013.01); *A61M 2205/52* (2013.01); *A61M 2205/583* (2013.01); *A61M 2205/6009* (2013.01); *A61M 2205/6018* (2013.01); *A61M 2205/6054* (2013.01); *A61M 2205/6063* (2013.01); *A61M 2205/6072* (2013.01); *A61M 2205/609* (2013.01); *A61M 2205/75* (2013.01); *A61M 2205/8206* (2013.01); *A61M 2207/00* (2013.01); *A61M 2210/0618* (2013.01)

(58) Field of Classification Search
CPC .......... A61M 15/0031; A61M 15/0033; A61M 15/0035; A61M 15/0036; A61M 15/0038; A61M 15/004; A61M 15/0041; A61M 15/0045; A61M 15/0046; A61M 15/0061; A61M 11/00; A61M 11/006–008; A61M 11/02; B67B 7/24; B67B 7/26; B67B 7/28; B05B 7/04; B05B 7/0408; B05B 7/00869; B05B 7/1436; B05B 7/144
See application file for complete search history.

(56) References Cited

U.S. PATENT DOCUMENTS

| | | | |
|---|---|---|---|
| 526,741 | A | 10/1894 | Rees |
| 746,749 | A | 12/1903 | Seidel |
| 757,157 | A * | 4/1904 | Turner .................. B05B 11/06 239/356 |
| 2,266,704 | A | 12/1941 | Fox et al. |
| 2,340,068 | A | 1/1944 | Rollin |
| 2,385,808 | A | 10/1945 | Goldbert |
| 2,485,184 | A | 10/1949 | Blackman |
| 2,564,400 | A | 8/1951 | Hall et al. |
| 2,566,806 | A | 9/1951 | Miller |
| 2,583,821 | A | 1/1952 | DuBios |
| 2,826,194 | A | 3/1958 | Golden |
| 3,066,669 | A | 12/1962 | Melfy |
| 3,097,645 | A | 7/1963 | Lester |
| 3,269,389 | A | 8/1966 | Meurer et al. |
| 3,802,604 | A * | 4/1974 | Morane .................. B65D 51/28 222/85 |
| 3,826,255 | A * | 7/1974 | Havstad .................. A61M 16/08 239/338 |
| 4,012,473 | A | 3/1977 | Lindsey |
| 4,018,387 | A | 4/1977 | Erb et al. |
| 4,093,124 | A | 6/1978 | Morane et al. |
| 4,351,003 | A | 9/1982 | Harlan et al. |
| 4,484,577 | A | 11/1984 | Sackner |
| 4,525,341 | A | 6/1985 | Deihl |
| 4,560,519 | A | 12/1985 | Cemy |
| 4,657,007 | A * | 4/1987 | Carlin .................. A61M 11/002 128/200.21 |
| 4,699,136 | A | 10/1987 | Xrauser |
| D295,787 | S | 5/1988 | Hegemann |
| 4,746,067 | A | 5/1988 | Svoboda |
| 4,982,875 | A * | 1/1991 | Pozzi .................. B65D 81/3222 604/416 |
| 5,086,765 | A | 2/1992 | Levine |
| 5,127,548 | A * | 7/1992 | Brunet ................ B05B 11/0078 222/321.6 |
| 5,149,330 | A | 9/1992 | Brightbill |
| 5,209,225 | A | 5/1993 | Glenn |
| 5,209,255 | A * | 5/1993 | Dehio .................. G05D 16/166 137/115.14 |
| 5,224,471 | A | 7/1993 | Marelli et al. |
| 5,287,847 | A | 2/1994 | Piper |
| 5,299,565 | A | 4/1994 | Brown |
| 5,396,986 | A * | 3/1995 | Fountain .................. A61C 5/66 206/219 |
| 5,503,139 | A * | 4/1996 | McMahon .......... B05B 7/0012 239/338 |
| 5,549,102 | A | 8/1996 | Lintl et al. |
| 5,579,757 | A * | 12/1996 | McMahon .......... B05B 7/0012 128/205.24 |
| 5,584,285 | A | 12/1996 | Salter et al. |
| 5,586,551 | A | 12/1996 | Hilliard |
| 5,624,898 | A | 4/1997 | Frey, II |
| 5,649,530 | A | 7/1997 | Ballini |
| 5,653,223 | A | 8/1997 | Pruitt |
| 5,653,700 | A | 8/1997 | Byrne et al. |
| 5,683,361 | A | 11/1997 | Elk et al. |
| 5,765,552 | A | 6/1998 | Zanen et al. |
| 5,806,723 | A | 9/1998 | DuBose |
| 5,906,198 | A | 5/1999 | Flickinger |
| RE36,070 | E | 9/1999 | Ballini |
| 6,045,530 | A | 4/2000 | Krueger et al. |
| 6,085,741 | A | 7/2000 | Becker |
| 6,135,358 | A | 10/2000 | Ballini |
| D438,612 | S | 3/2001 | Frey, II |
| 6,206,849 | B1 | 3/2001 | Martin et al. |
| 6,313,093 | B1 | 11/2001 | Frey, II |
| 6,474,861 | B1 * | 11/2002 | De Laforcade .... B65D 81/3211 215/DIG. 8 |
| 6,619,284 | B2 | 9/2003 | Kong |
| 6,644,304 | B2 | 11/2003 | Grychowski et al. |
| 6,644,305 | B2 | 11/2003 | MacRae et al. |
| 6,698,421 | B2 | 3/2004 | Attolini |
| 6,701,916 | B2 | 3/2004 | Mezzoli |
| 6,726,005 | B2 * | 4/2004 | Lentine .................. A61C 5/66 206/63.5 |
| 6,732,731 | B1 | 5/2004 | Tseng |
| 6,997,357 | B2 * | 2/2006 | Fuchs .................. B05B 11/0083 222/145.5 |
| 7,131,439 | B2 | 11/2006 | Blacker et al. |
| D542,910 | S | 5/2007 | MacRae |
| 7,288,083 | B2 | 10/2007 | Holman |
| D557,407 | S | 12/2007 | Lithgow et al. |
| 7,407,118 | B2 | 8/2008 | Sevy |
| 7,543,581 | B2 | 6/2009 | Djupesland |
| 7,559,491 | B1 | 7/2009 | Chang |
| D629,884 | S | 12/2010 | Stephens |
| 7,870,952 | B2 * | 1/2011 | Fontana .............. B65D 51/2814 206/219 |
| D641,764 | S | 7/2011 | Lipscomb et al. |
| 8,146,587 | B2 | 4/2012 | Flickinger |
| 8,162,921 | B2 | 4/2012 | Flickinger |
| D689,185 | S | 9/2013 | Flickinger |
| 8,616,195 | B2 | 12/2013 | Power et al. |
| D704,825 | S | 5/2014 | Flickinger |
| 8,925,544 | B2 | 1/2015 | Flickinger |
| 2003/0195507 | A1 | 10/2003 | Stewart et al. |
| 2004/0031485 | A1 * | 2/2004 | Rustad .................. A61M 11/00 128/200.14 |

(56) References Cited

U.S. PATENT DOCUMENTS

| | | |
|---|---|---|
| 2004/0254562 A1 | 12/2004 | Tanghoj et al. |
| 2005/0048436 A1 | 3/2005 | Fishman et al. |
| 2006/0124778 A1 | 6/2006 | Vendrine et al. |
| 2008/0054099 A1 | 3/2008 | Giroux et al. |
| 2008/0147040 A1 | 6/2008 | Dikshteyn |
| 2008/0154183 A1 | 6/2008 | Baker |
| 2008/0283050 A1* | 11/2008 | Faram ............... A61M 15/0003 128/200.21 |
| 2009/0054833 A1 | 2/2009 | O'hare |
| 2009/0247941 A1 | 10/2009 | Lu |
| 2011/0040250 A1 | 2/2011 | Abate |
| 2011/0132354 A1 | 6/2011 | Flickinger et al. |
| 2011/0137290 A1 | 6/2011 | Flickinger et al. |
| 2011/0247610 A1 | 10/2011 | Nakamura |
| 2011/0303218 A1 | 12/2011 | Yadidi |
| 2012/0000460 A1 | 1/2012 | Flickinger |
| 2012/0152238 A1 | 6/2012 | Flickinger |
| 2012/0160237 A1 | 6/2012 | Flickinger |
| 2013/0267864 A1* | 10/2013 | Addington ........... A61B 5/7278 128/200.14 |
| 2014/0171880 A1 | 6/2014 | Carpenter |
| 2014/0283820 A1 | 9/2014 | Flickinger |

FOREIGN PATENT DOCUMENTS

| | | |
|---|---|---|
| TW | 200932204 | 8/2009 |
| WO | 0189615 | 11/2001 |
| WO | 111153406 | 12/2011 |

OTHER PUBLICATIONS

Foo et al., "The Influence of Spray Properties on Intranasal Deposition" Journal of Aerosol Medicine, vol. 20, No. 4, 2007, pp. 495-508 (15 pages).

Harvey et al., "Fluid residuals and drug exposure in nasal irrigation" Otolaryngology-Head and Neck Surgery (2009) 41, 757-761 (5 pages).

Laube, "Devices for Aerosol Delivery to Treat Sinusitis" Journal of Aerosol Medicine, vol. 20, Supplement 1, 2007 pp. S5-S18 (14 pages).

Ying, "The Nose May Help The Brain: Intranasal Drug Delivery for Treating Neurological Disease"; Future Neural, 2008, 3(1), pp. 1-4.

Rhee et al., "Clinical Consensus Statement: Diagnosis and Management of Nasal Valve Compromise" Otolaryngology Head and Neck Surgery (2010) 143, pp. 48-59.

* cited by examiner

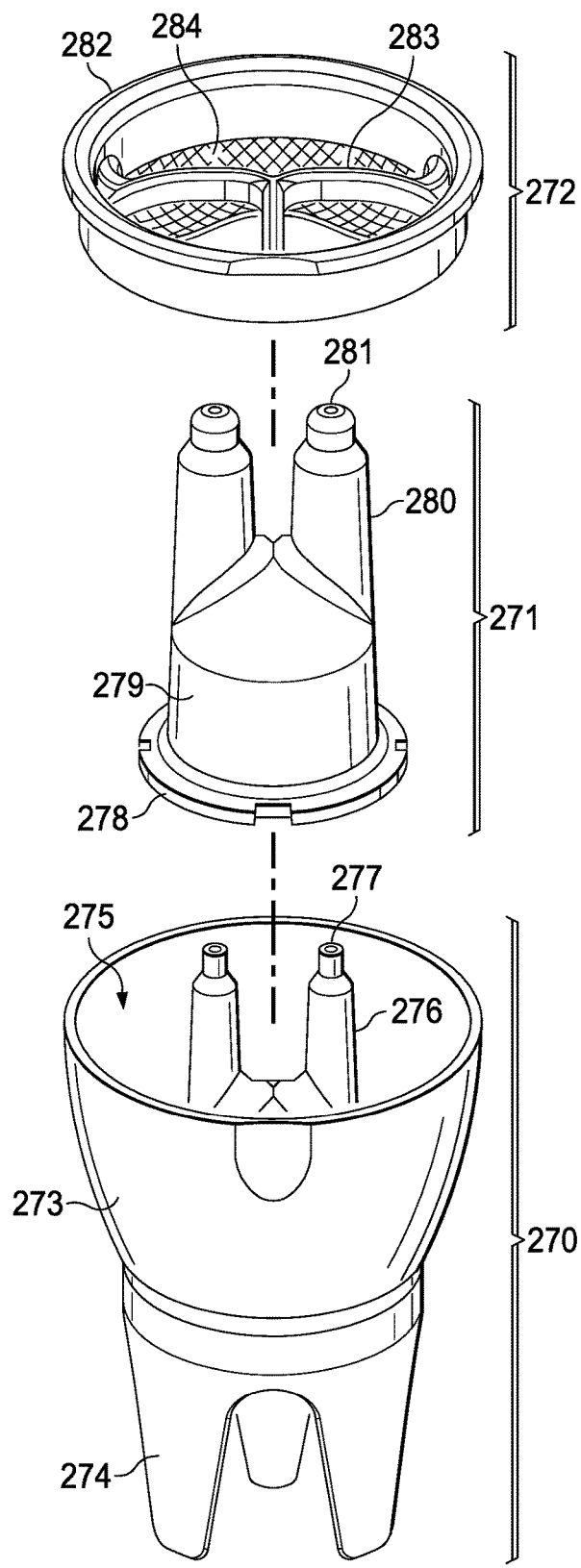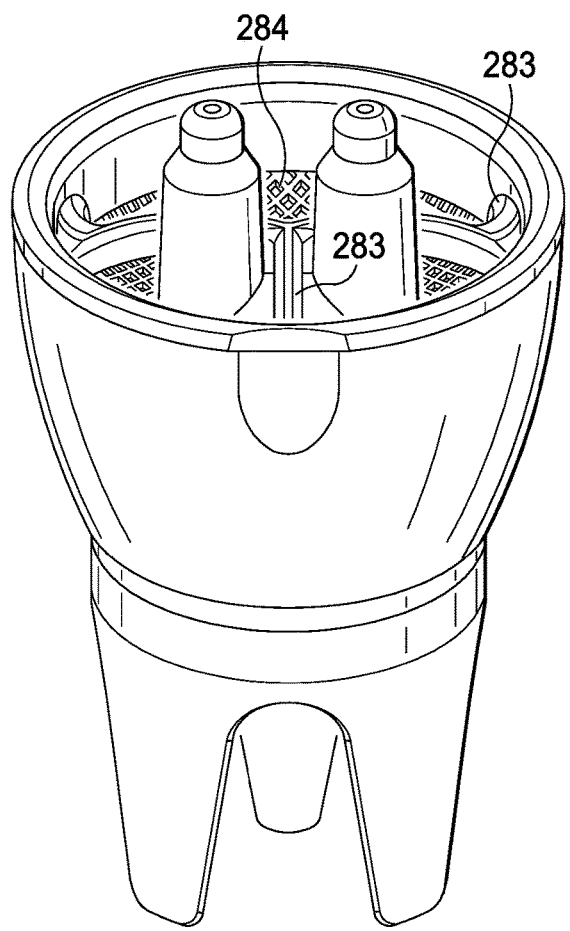
FIG. 15
FIG. 16

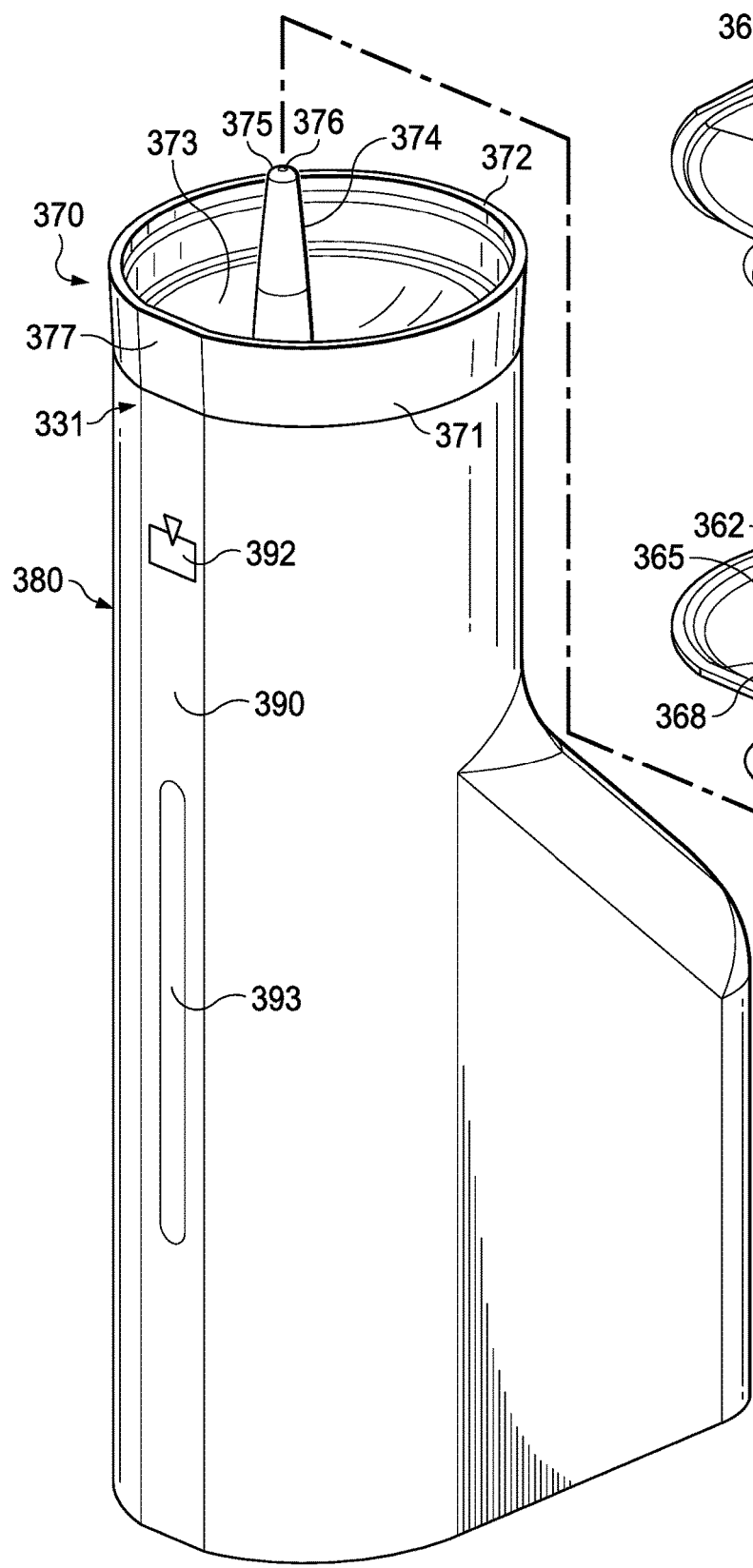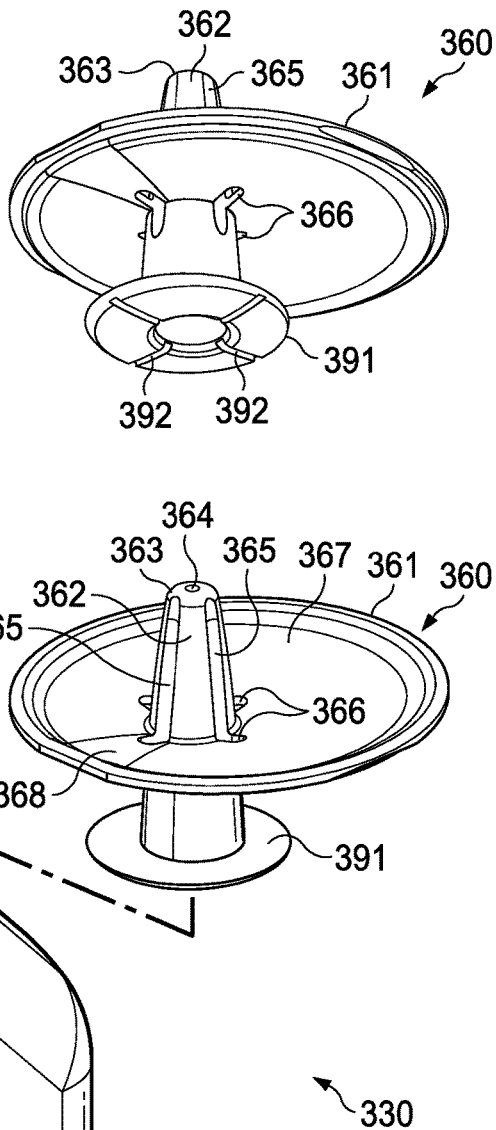

NASAL DRUG DELIVERY DEVICE AND METHOD OF MAKING SAME

CROSS-REFERENCE TO RELATED APPLICATIONS

This application is a continuation of U.S. application Ser. No. 15/263,233, filed Sep. 12, 2016, now U.S. Pat. No. 10,682,331, which is a continuation-in-part of U.S. application Ser. No. 15/225,465 filed Aug. 1, 2016, abandoned, which is a continuation-in-part of U.S. application Ser. No. 14/295,502, filed Jun. 4, 2014, abandoned, which is a continuation-in-part of U.S. application Ser. No. 13/404,623, filed Feb. 24, 2012, now U.S. Pat. No. 9,440,020, wherein all of the above-mentioned applications are hereby incorporated herein by reference.

TECHNICAL FIELD

The present invention generally relates to devices for administering medicated fluids to the upper airway in mist or droplet form.

BACKGROUND OF THE INVENTION

Devices used for administering liquid medication to a patient by way of mist or liquid droplets are generally called nebulizers and are primarily used for the delivery of medication into the lungs or lower airways. These devices are best suited for the inhalation of the mist or aerosol through the patient's mouth or nose. This is accomplished by creating an aerosol of small droplets or particles of 3-5 microns in diameter, and holding the resultant aerosol in a reservoir. The aerosol is then inhaled and the droplets are drawn into the lungs on the inhaled airstream. Aerosol droplets or particles are therefore so small and lightweight that, for the most part, they bypass the mouth, nose and throat, leaving very little, if any, of the aerosol deposited in the nasal cavity. However, some cases require the introduction of liquid droplets to the patient's nasal passages.

Current nasal drug delivery devices require medications to be delivery in a separate container such as an ampoule or capsule, which requires additional handling steps by the user. In the case of medicated powders, for example, additional preparation must be performed to form a solution. These preparation steps may result in contamination, spillage, incorrect dosage dispensing, or misplacement. Shelf life, sterility, and stability of certain drugs is also shortened when drugs are delivered as a fluid to a patient. For example, some medications require cold storage throughout their life cycle.

SUMMARY OF THE INVENTION

There is a need for a drug delivery device that provides ease of use and accurate dosage in a quick step. There is further a need for a device capable of storing liquids and/or powders to alleviate the problems caused by additional handling of certain medications by a user. The device should be simple and minimize handling while alleviating the problems of shortened shelf-life. These benefits, among others, are provided by the improvements described herein.

Below is a simplified summary of this disclosure meant to provide a basic understanding of some aspects of the products and methods described herein. This is not an exhaustive overview and is not intended to identify key or critical elements or to delineate the scope of the description. Its sole purpose is to present some concepts in a simplified form as a prelude to the more detailed description below.

Provided herein is a nasal drug delivery device comprising a canister comprising a reservoir, an air exit port and a puncturing element on an inner surface of the canister, the air exit port extending beyond a rim of the canister and the puncturing element comprising a puncturing tip below the rim; an insert comprising a fluid channel that fits over the air exit port, and a pressurized air supply source for introducing pressurized air through the air exit port to dispense a medication within the reservoir in the form of a mist. In one embodiment, the nasal drug delivery device comprises an extension between the fluid channel and the canister, and a storage compartment comprising filling, the storage compartment attached to the extension and the extension comprising an air vent to release air from the storage compartment, wherein at least a portion of the storage compartment is formed of a material that can be penetrated by the puncturing element to release a filling into the canister to provide for a medication to be dispensed through an exit hole of the fluid channel directly to a user. That is, the medication or medicated liquid is dispensed as a mist without passing through any intervening structures or components. In one embodiment, the medication within the reservoir is derived at least in part from a separate, detached storage compartment, said detached storage compartment pierceable by the puncturing tip to provide for the filling of the reservoir with the medication due to piercing. In any of the above embodiments, the reservoir comprises a powder. In some embodiments wherein the reservoir comprises a powder, the storage compartment comprises a liquid capable of substantially dissolving the powder. In any of the above embodiments, the filling comprises a liquid. In any of the above embodiments comprising an extension, the storage compartment is permanently attached to the extension. In any of the above embodiments, the storage compartment is optionally detachable. In any of the above embodiments, the storage compartment comprises an accessible filling port. In some embodiments, the storage compartment comprises a hermetic seal. In any of the above embodiments, the canister and the insert are sealed together.

In any of the above embodiments, the nasal drug delivery device may comprise more than one storage compartment. In any of the above embodiments, the nasal drug delivery device may comprise more than one puncturing element.

In any of the above embodiments, the fluid channel fits over the air exit port to provide a small space between an outer surface of the air exit port and an inner surface of the fluid channel. In any of the above embodiments, the fluid channel comprises a groove extending vertically along the exterior of the fluid channel to an aperture in the extension, the aperture creating a channel to the reservoir of the canister.

A wide number of medications for the device described herein may be used to reach the nasal and paranasal cavities, including dry forms such as powders, liquid forms, and/or medications that require dilution, as further described below.

Other aspects, embodiments and features of the invention will become apparent from the following detailed description of the invention when considered in conjunction with the accompanying drawings. The accompanying drawings are schematic and not intended to be drawn to scale. In the figures, each identical or substantially similar component that is illustrated in various figures is represented by a single numeral or notation. For purposes of clarity, not every component is labeled in every figure. Nor is every component of each embodiment of the invention shown where illustration is not necessary to allow those of ordinary skill in the art to understand the invention.

BRIEF DESCRIPTION OF THE DRAWINGS

The novel features believed characteristic of the invention are set forth in the appended claims. The invention itself, however, as well as mode of use and advantages thereof, will best be understood by reference to the following detailed description of illustrative embodiments when read in conjunction with the accompanying drawings, wherein:

In one aspect, a nasal irrigator of the present invention comprises a main canister with a reservoir for holding fluid, wherein the canister includes at least two air exit ports; a removable insert with a circular base that fits within said main canister, wherein the insert includes at least two fluid channels that mate with said air exit ports of the main canister, said fluid channels comprising two tubes ending in a common bell housing above the base, wherein said base holds the insert just off of the main canister surface, allowing fluid to pass between the base and main canister, and further wherein the fluid channels are larger in diameter than the air exit ports, thereby providing a small space between the outer surface of the air exit ports and the inner surface of the fluid channels that allows fluid from said reservoir to be drawn upward between the air exit ports and fluid channels and expelled as a mist in an aerosol plume through exit holes in the fluid channels due to a venturi effect created by pressurized air from the air exit ports; and at least one nozzle coupled to the bottom of said main canister to create at least one air chamber defined by the nozzle and said air exit ports, wherein the nozzle includes an air inlet for providing pressurized air into said air chamber.

Figure 1:
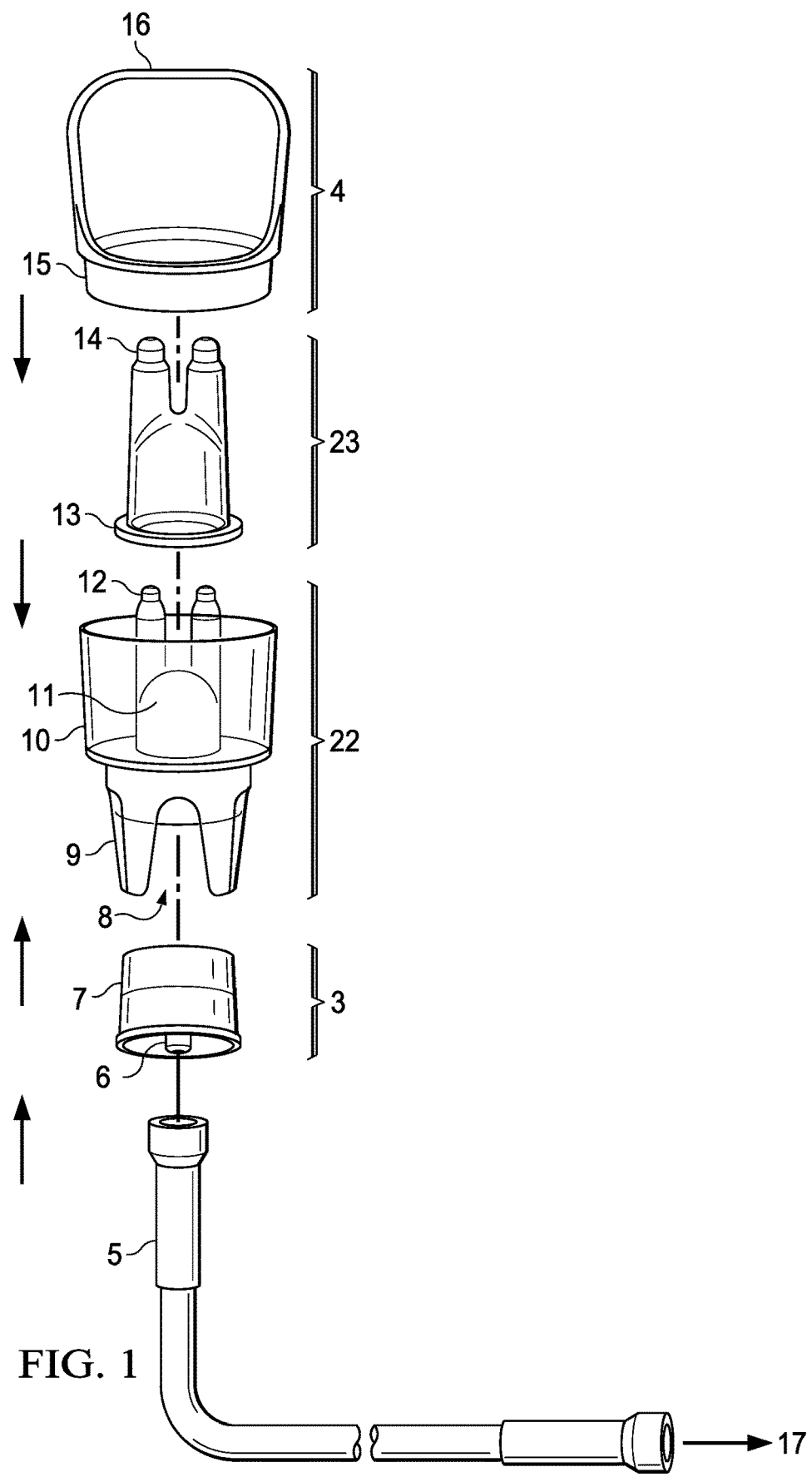
FIG. 1 is an exploded view of a nasal irrigator in accordance with an embodiment of the present invention.

FIG. 1 is an exploded view of a nasal irrigator in accordance with an embodiment of the present invention. The nasal irrigation device comprises three major sections. The first major section is the main canister 22 which has an expanded reservoir 10 that is capable of holding up to 50 ml of fluid. The inner portion of the reservoir shaped at the bottom to ensure maximal uptake of fluid to reduce waste.

The main canister 22 also includes an air chamber 11 terminating in two air exits 12 (one for each nostril) with holes sufficient to deliver an airstream that is able to atomize fluid and stent-open the upper airway. In one embodiment, each exit port 12 has at least one hole of between 0.020" and 0.060" (0.508 mm-1.524 mm) in diameter and a web-thickness or hole length of between 0.030" and 0.200" (0.762 mm-5.08 mm).

On the bottom of the main canister 22 is a foot section 9 that includes one or more feet for stability and an air inlet 8 for the admission of pressurized air to create the air stream through air exits 12. The foot section 9 enables the canister 22 to stand up when set on a horizontal surface and is designed to fit into a standard docking port of an air compressor pump to enable the device to remain upright in a hands-free manner so as to remain filled with the air supply tube attached.

In the shown example, the main canister 22 has a two-step circumference to fit a holder (not shown) and provide adequate fluid volume for nasal irrigation, with the smaller diameter foot section 9 enabling the user to rest device in the holder with tube attached. In an alternate embodiment (not shown) the foot section 9 is wider than the reservoir section 10.

The second major section of the irrigator is the insert 23, which is shown with a base 13 that holds the inside surface of the insert 23 just off of the outer surface of the feature within reservoir 10 of the main canister 22. At least one channel is located in the bottom of the insert 23 to act as a conduit for fluid from the reservoir 10 to enter the base of the insert. The insert 23 includes fluid channels 14 that mate with the air exit ports 12 of the main canister 22. Peaks or extensions may be included on the air exits 12 to ensure centering of the insert 23 and its fluid channels 14 on the air exits. Similarly, tabs may extend from the inside of the fluid channels of the insert to the outer surface of the main canister to ensure alignment. As shown, fluid channels 14 of the insert 23 comprise two tubes with one end at the bottom of the reservoir 10 and one end that is positioned in the airstream so that the airstream creates a negative pressure in each tube that draws fluid into the airstream where it is atomized (described below).

In the embodiment shown in FIG. 1, the atomizer outlets 12, 14 extend above the edge of the main canister 22. However, in an alternate embodiment (not shown) the atomizer nozzles are even with or recessed within the edge or portions of the edge of the main canister.

The insert 23 is keyed in at least one location with the reservoir 10 to ensure that the insert does not rotate in relation to the exit ports 12 of the main canister and to aid in centering of the insert 23 and its fluid channels 14 on the air exits. The insert may include a feature to ensure that it is inserted into the main canister in only one orientation. In one embodiment, a loop (not shown) extends down to the saddle of the insert 23 to hold down the insert.

The fluid channels 14 are slightly larger in diameter than the air exit ports 12 of the main canister, thereby providing a small space (preferably 0.0001" to 0.010" (0.00254-0.254 mm)) between the outer surface of the air exit ports and the inner surface of the fluid channels. This space allows fluid from the reservoir 10 to proceed upward between the air exit ports 12 and the fluid channels 14 until being expelled by pressurized air. When the insert 23 is installed in the main canister 22, the orifices of the fluid channels 14 are positioned relative to the air exits 12 so as to create a venturi effect with the pressurized gas expelled from the gas tubes. Because the fluid exits 14 in the insert 23 are larger than the air exits 12, when air is forced through the air exits at an appropriate volume and speed, fluid in the reservoir 10 is drawn up into the space between the insert and air exits ports. When this fluid meets the subsequent airstream it is atomized into particles conducive to deposition in the upper airway. The airstream is sufficient to penetrate the nasal cavity above the inferior turbinate so as to deposit the fluid and provide a washing, irrigation, or deposition to the upper reaches the nasal cavity.

The exit holes of the fluid channels 14 are small enough to ensure that mist is created but large enough to ensure that the holes of the insert may be chamfered so that the walls of the exit holes are angled away from a central axis at an angle that exceeds the cone of the aerosol plume to reduce agglomeration of the mist particles upon exit, providing a more uniform particle size throughout the plume. The fluid channel size may be adjusted to change the particle size of the mist. In one embodiment the tubes have a mating section on the upper end that enables the changing of the orifice in the air stream via a series of nozzles that can be inserted into the upper end of the tubes such that the size of the nozzle orifice that is placed into the airstream is varied.

The third major section of the irrigator is nozzle cone 3. The nozzle 3 includes an air inlet 6 and a mating surface 7, which attaches to the air inlet 8 of the main canister 22 to create air chamber 11 defined by the nozzle and the two exit ports 12 described above. The length of all components on the nozzle cone 3 preferably is limited so that the nozzle cone or its components do not extend past the foot section 9 on the main canister 22 when the device is assembled to enable the device to be placed on a flat surface in an upright or standing position.

Ribs may also be molded into the nozzle cone 3 to provide radial stiffness. In another embodiment, the nozzle cone is made of rigid plastic.

The mating surface between the nozzle 3 and main canister 22 is designed to ensure a tight bond can be created. In an alternate embodiment the mating surface between the nozzle 3 and main canister 22 is essentially straight.

In one embodiment, the nozzle cone 3 is attached permanently to the main canister 22. In an alternate embodiment, the nozzle cone 3 may utilize a friction fit or have a positive connection such as a thread or other mechanism allowing the nozzle cone and main canister 22 to be disconnected for cleaning. This detachable embodiment may include an air seal such as an O-ring as well as a flange to grasp for easy disassembly.

An air supply tube 5 connects the air inlet 6 of the nozzle cone with an air supply 17.

Figure 2:
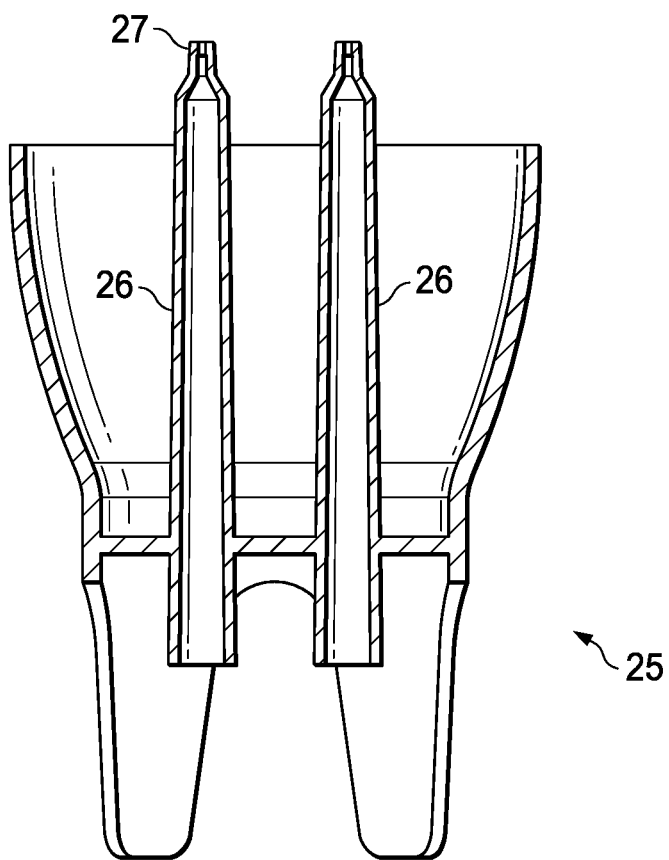
FIG. 2 shows a cross sectional view of a canister in accordance with an alternate embodiment of the invention.

FIG. 2 shows a cross section view of a canister 25 in accordance with an alternate embodiment of the invention. In this embodiment, rather than a single air chamber and nozzle, the canister 25 includes separate air passage chambers 26 that terminate in the air exits 27. These separate air passage chambers 26 can connect to separate air sources via separate nozzles. Alternatively, the separate air passage chambers 26 can be connected to a common air source via split tubing such as a Y or T adapter (not shown).

In addition to the three major sections described above, the irrigator may include a cover 4 that has a mating surface 15 that creates an isodiametric connection to the main canister 22. In the example shown in FIG. 1, the cover 4 is a broad cover region to block space between the nose, eyes and the rest of the face when in use as shown (see FIG. 4). In this embodiment the cover 4 is designed to confine the mist expelled from the fluid channels and shield the patient's eyes, with an opening to provide room for the patient's nose within the apparatus. The cover 4 is radiused along the distal end away from the main canister 22 to fit a broad variety of faces and is open to enable air to enter as the fluid is drawn down and capture and recycle fluid that falls off the face.

The cover may also incorporate a cross member or other device that retains the insert 23 to allow for clearance of the nose and prevent lifting of the insert at the initiation of atomization. In one embodiment a sleeve or partial sleeve extends from the cover 4 to the base of the insert 23 to hold the insert down.

Figure 3:
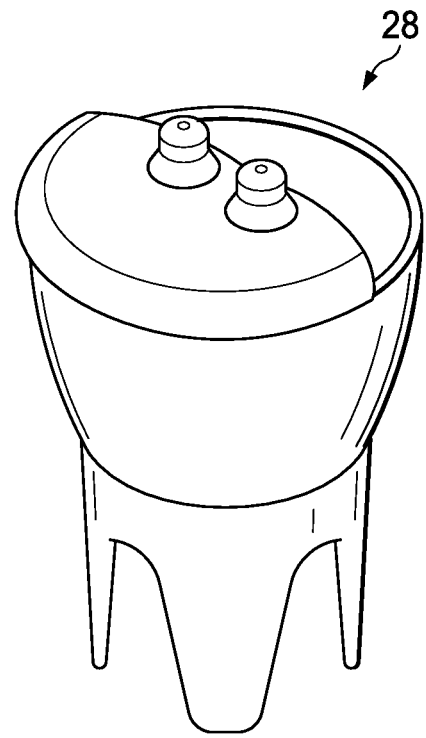
FIG. 3 shows an alternate embodiment of the cover in accordance with the present invention.

FIG. 3 shows an alternate embodiment of the cover in accordance with the present invention. In this embodiment, the cover 28 is a semi-circular lid that does not block the eyes but instead retains the insert and blocks material from re-entering the main canister from the nose.

The present invention may incorporate a feature that guides the user to angle the spray into the nose at a set angle from 0-90 degrees from the plane defined as the front of the face from the chin to the forehead (i.e. the vertical plane of the face). For example, the irrigator may include a setoff designed to set a specific angle of 30 degrees, 45 degrees, or 60 degrees from the vertical plane of the face. The setoff may be removable for various size faces or noses.

Materials suitable for construction of the irrigator include rigid plastic, glass, metal, ceramic, carbon fiber or other rigid material, or an elastomer plastic or some combination thereof.

One embodiment of the nasal irrigation device (not shown) is egg-shaped or ovoid for better fit into the hand and a pleasing look.

Figure 4:
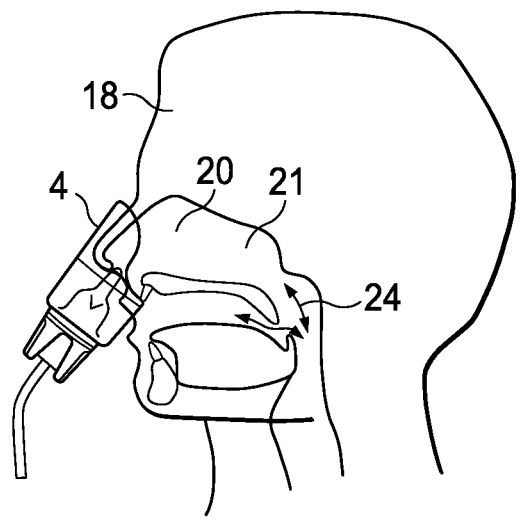
FIG. 4 illustrates the use of the nasal irrigator of FIG. 1 in accordance with an embodiment of the present invention.

FIG. 4 illustrates the use of the nasal irrigator in accordance with the present invention. The irrigator is placed over the face of the user 18 and angled such that the cover 4 blocks the eyes. The mist 20 enters the nasal passages 21, and the patient breathes through both the mouth and nose at the same time (24). The mist 20 passes into the nasal passages 21 independent of the patient's breathing.

The air-fluid mixture is calibrated to achieve nasal irrigation within a short period of time, without the need for the fluid to exit the nostrils at the time of irrigation, and with a particle size that is designed to loosen the mucous or to enter the sinus cavities, as desired by the end user and not enter the pharynx or the lungs.

In one aspect, the method of nasal irrigation comprises providing fluid in a canister that includes at least two air exit ports mated to corresponding fluid channels, wherein the fluid channels are larger in diameter than the air exit ports, thereby providing a small space between the outer surface of the air exit ports and the inner surface of the fluid channels. This space allows fluid from said reservoir to be drawn upward between the air exit ports and fluid channels. Pressurized air is pumped through the air exit ports, thereby creating a venturi effect that draws fluid from said reservoir upward between the air exit ports and fluid channels and expels the fluid as a mist in an aerosol plume through exit holes in the fluid channels and into a user's nasal cavity above the inferior nasal turbinate independent of the user's breathing. The pressurized air has a pressure of 0.069-1.035 bar and an airflow rate of 1-12 liters per minute, producing a fluid delivery rate of 1-20 ml per minute.

The method of nasal irrigation offers a fast, convenient method of atomizing saline or medication for delivery to the nose, with a variable particle size up to 100 microns. In one embodiment, particle size is at least 10 microns.

Using an air pressure of 1-15 psi (0.069-1.035 bar) creates a pressurized airflow that enables the resultant air-mist stream to stent-open the soft tissues of the upper airway. In one embodiment, the air pressure ranges from about 3-12 psi (0.207-0.823 bar), with about 1-12 lpm of airflow, and a fluid delivery rate of about 1-20 ml per minute. In one embodiment, the air pressure ranges from about 4-8 psi (0.276-0.552 bar), with about 3.5-8 lpm airflow, and about 15 ml per minute fluid delivery.

The resultant mist reaches the area of the nasal cavity and paranasal sinuses above the inferior nasal turbinate or chonchae to ensure that the mist reaches the areas of the sinus ostia to clear this area of the nasal cavity and enable the natural mucociliary flow to clear the sinuses.

Recent medical research has noted that the olfactory and trigeminal nerves may be used as a pathway to deliver large and small molecules to the brain and central nervous system that bypasses the blood brain barrier and first pass metabolism of intravenous and oral delivery routes. (See Dhanda, D., Frey W H $2^{nd}$, Leopold, D., Kompella, U B: "Nose-to-brain delivery approaches for drug deposition in the human olfactory epithelium." *Drug Delivery Technol.* 5(4), 64-72 (2005).) Frey and others have demonstrated that these nerves may be reached via the nasal mucosa overlying the olfactory cleft and cribriform plate where these nerves are concentrated. Furthermore, the frequency of dosing of many of these materials requires a delivery system that is practical and easy to use. In the case where systemic delivery of drugs via the nose is desired, maximizing the surface area of the mucosa covered by the medication may improve the amount of medication that is absorbed by the body and may reduce the variability of absorption between doses and across patients; thus improving the bioavailability of the drug and reducing the variability of bioavailability of the drug. Furthermore, by maximizing the surface area available for absorption of any given drug, the concentration required to deliver an effective dose may be reduced when compared to traditional metered dose inhaler technology, enabling more drugs to be delivered transnasally than with other systems.

However, the literature suggests that adequate delivery systems are lacking for the reliable and practical delivery of these substances to these areas. Delivery of large particles (>10 microns) of liquids in the described volumes as provided by the present invention, offers advantages over dry powder, minute volumes and high volume solutions. These advantages include covering the whole nasal mucosa, formulating drugs for patient comfort vs. concentration, reducing the inadvertent delivery of aerosolized materials to the lungs; and the ability to deliver precious materials economically and judiciously while reducing waste.

In one aspect, the present invention provides a method of treating neoplasms of the nasal cavity comprising fluid in a canister, wherein the canister includes a reservoir and at least two air exit ports, and wherein said fluid contains corticosteroids. The air exit ports are mated to corresponding fluid channels, wherein the fluid channels are larger in diameter than the air exit ports, thereby providing a space between the outer surface of the air exit ports and the inner surface of the fluid channels, which allows fluid from said reservoir to be drawn upward between the air exit ports and fluid channels. Pressurized air is pumped through the air exit ports, thereby creating a venturi effect that draws fluid from said reservoir upward between the air exit ports and fluid channels and expels the fluid as a mist in an aerosol plume through exit holes in the fluid channels and into a user's nasal cavity above the inferior nasal turbinate independent of the user's breathing.

The present invention allows for delivering steroids for the long-term control of benign neoplasms of the nasal cavity, such as inflammatory nasal polyps, granulomas, etc., without systemic doses of steroids or steroid injections. It also provides the ability to irrigate the whole nasal mucosa to manage the disruption of natural filtering and humidification often caused by ablative and reconstructive surgical treatment of neoplasms. Unlike prior art saline irrigation and nasal sprays which do not reach many of the areas of concern in the nasal vestibule and paranasal sinus areas, the irrigator of the present invention delivers adequate moisture in less than one minute to the areas of concern. The present invention also avoids pooling of moisture that can otherwise provide a nidus for infection and cause excessive removal of the immunologic mucus blanket of the nose.

The high frequency of steroid administration needed to control neoplasm growth requires a delivery system that is practical and easy to use. The irrigator of the present invention can deliver these steroids quickly—in less than one minute—covering the whole nasal cavity and does so without unduly exposing the body to the effects of systemic steroids.

For example, using the irrigator of the present invention, 0.60 mgs of corticosteroid is typically delivered to the nasal cavity, between two and ten times the amount delivered via metered dose inhalers. In some instances, antibiotics are delivered along with the corticosteroid to treat infections such as *Staphylococcus aureus*. Staph aureus endotoxin has been shown to up-regulate the beta isoform of cortisol receptor ($CR_\beta$) in cell membranes that is responsible for inhibiting the response to corticosteroids, and it is believed that the Staph infection may contribute to steroid-resistant nasal polyps. The concurrent administration of antibiotics with the corticosteroid via the irrigator of the present invention reduces this endotoxin effect on the cortisol receptor, thereby increasing the efficacy of the steroid therapy.

The pressure and airflow necessary to deliver material to the upper portion of the nose can be reduced if the aerosol is introduced distal of the nares at or above the nasal valve and proximal to the inferior turbinate. The present invention delivers droplets or mists with an air stream and particle sizes designed to stay in the upper airway under sufficient pressure and airflow to overcome the normal aerodynamics of the nose. Unlike prior art methods, the present invention releases mist at or above the nasal valve, thereby avoiding deflection of the fluid off the walls of the nostril and nasal valve.

Effective delivery of material to the nasal cavity requires a particle size that is large enough to fall out of the airway before reaching the oropharynx, delivered under sufficient pressure and airflow to overcome the aerodynamics of the nasal cavity. The nasal cavity is shaped to efficiently deliver air to the lungs. Air enters the nares and passes through the nasal valve, which resides approximately 1.3 cm above the nares and is the narrowest portion of the nose, with a cross-section of at approximately 0.73 $cm^2$. The nasal valve is the narrowest anatomic portion of the upper airway, resulting in the volume of air inspired nasally to be efficiently cleansed and humidified by the nasal cavity.

Figure 5:
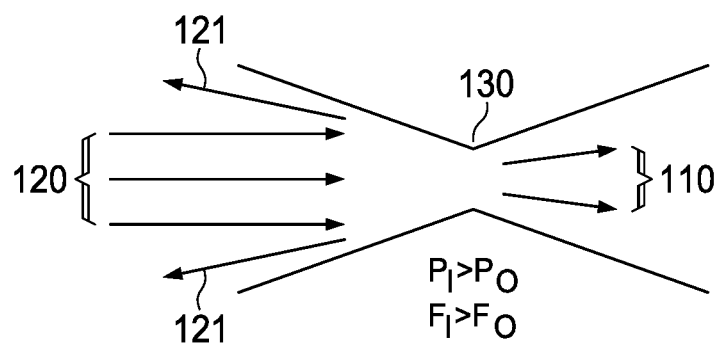
FIG. 5 conceptually illustrates the function of the nasal valve in aerosol delivery that particles of a size to ensure that the majority of the mist is retained or deposited within the upper airway. The invention also provides a nasal irrigator designed to deliver a mist to the upper airway through both nostrils simultaneously.

FIG. 5 conceptually illustrates the function of the nasal valve in aerosol delivery that is initiated below the nasal valve. Arrows 120 represent an aerosol flowing into the nasal nares. As illustrated by arrows 121, a portion of this aerosol is reflected off the walls of the nose as the passageway narrows to the nasal valve 130. This reflected material falls out of the nose and is either wasted or is recollected by the device to be delivered repeatedly.

The nasal valve 130 acts to reduce the flow (F) and pressure (P) of that portion of the aerosol stream that crosses the valve and enters the nasal cavity 110. Thus, Flow in ($F_I$) is greater than Flow out ($F_O$), and Pressure in ($P_I$) is greater than Pressure out ($P_O$). As a result, aerosol entering the nasal cavity external to the nasal valve requires a higher pressure and flow rate to achieve the same aerosol distribution as an aerosol introduced internal to the nasal valve.

Air entering the nose meets additional resistance at the level of the inferior turbinate, which directs air downward along the floor of the nose along the path of least resistance. During inhalation, the airflow is dominated by the negative pressure being generated from the lower airway and is directed to the nose from the pharynx. This negative pressure and the structure of the nasal cavity conspire to direct the majority of the air through the lower third of the nose, with very little air entering the upper portion of the nose. Indeed, studies have shown that to reach the upper portion of the nose under the negative pressure of normal breathing, an aerosol must be placed very precisely at the front of the nares. To overcome the aerodynamics of the nose, the delivery system must provide a positive pressure and sufficient airflow to fill the whole nasal cavity.

Prior art devices that deliver aerosol below the nasal valve must generate higher pressure and flow rates since the valve acts to lower the pressure and flow as the aerosol passes through it. The design of the present invention is directed to the self-administration of fluid to the nasal passages of a patient while ensuring the device fits a wide variety of faces and for simplicity of design, ease of manufacturer. It requires lower pressure and airflow and produces less mess by virtue of delivery above the nasal valve, and simplicity of use, including short delivery times.

The invention delivers fluid to the nasal passages with little interaction required by the user and under sufficient pressure to stent-open the airway. The invention delivers particles of a size to ensure that the majority of the mist is retained or deposited within the upper airway, while maximizing the amount of drug delivered and eliminating reflection back from the nasal valve.

Figure 6:
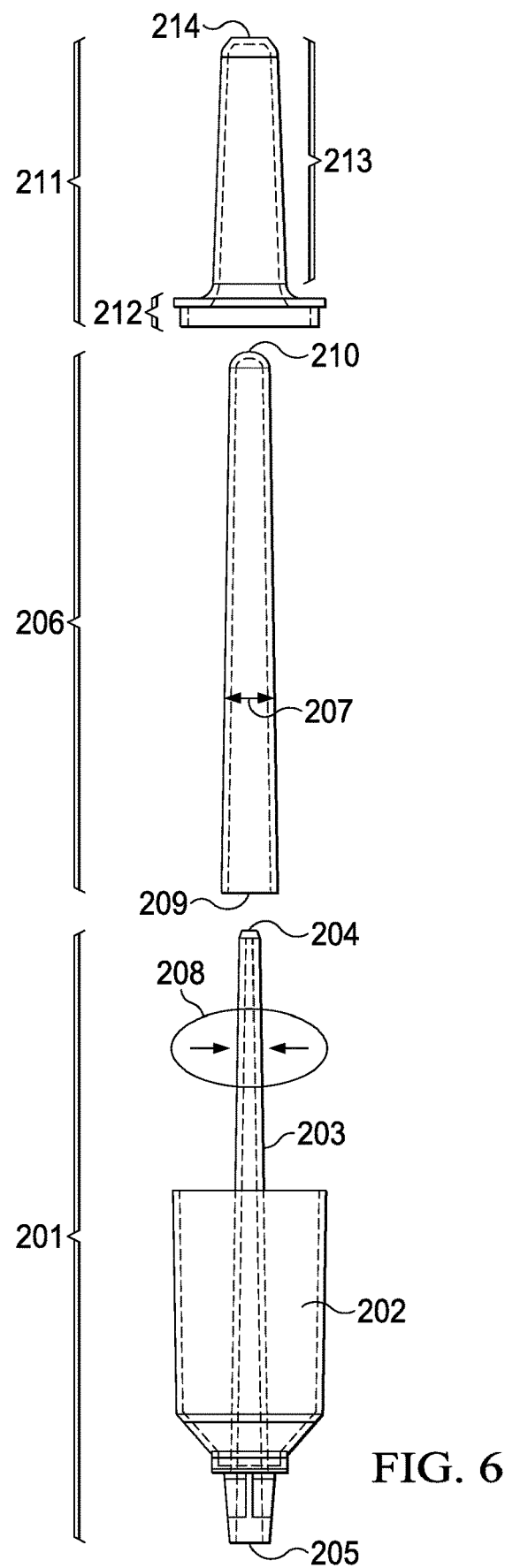

FIG. 6 shows an embodiment of a nasal irrigator in accordance with the present invention. The nasal irrigator comprises three main components. The first component is the main canister 201, which has a fluid reservoir 202 and an air exit port 203 that extends above the reservoir. In one embodiment, the reservoir 202 holds up to 30 ml of fluid or medication. As shown in FIG. 1, the lower portion of the reservoir is downward sloping to ensure fluid collects at the bottom, which allows maximal uptake of fluid through fluid channels (explained below), thereby minimizing waste.

The air exit port 203 has at least one exit hole 204 at the top sufficient to deliver an airstream that is able to atomize fluid and deliver the aerosol to the whole nasal cavity. In one embodiment, the exit hole 204 is between 0.020" (0.508 mm) and 0.060" (1.524 mm) in diameter and the air exit port has a web-thickness of between 0.030" and 0.200" (0.762 mm-5.08 mm).

The main canister 201 also included an air inlet 205 on the bottom for the admission of pressurized air to create the air stream exiting the air exit port 203.

In one embodiment, the main canister 201 has optional "feet" on the bottom (as shown in FIG. 1) for stability. The length of all components on the nozzle cone is limited so that the nozzle cone or its components do not extend past the feet on the main canister when the device is assembled to enable the device to be placed on a flat surface in an upright or standing position. The canister 201 may also be designed to fit into a standard docking port of an air compressor to enable the device to remain upright in a hands-free situation so as to be filled with the air supply tube attached.

The second main component of the nasal irrigator is an insert 206 that fits over the main canister's air exit port 203. The insert 206 can be permanently attached to the canister 201 or it may be removable. The insert 206 has an aerosol exit 210 that is concentrically aligned with the exit hole 204 of the air outlet 203. A peak or extension on the air exit port 203 may ensure centering of the insert over the air outlet. Similarly, tabs on the insert may be used to center the insert over the air outlet and prevent it from being moved by force. The aerosol exit 210 is slightly larger than the exit hole 204 of the air exit port 203 to enable atomization of fluid in the air stream.

The insert 206 has a tapered inner diameter 207 that is larger than and follows the contours of the outer diameter 208 of the air exit port 203. This difference in diameter creates a space of between 0.0001" (0.00254 mm) and 0.010" (0.254 mm) between the inner surface of the insert 206 and the outer surface of the air exit port 203. This space allows fluid to be drawn from the reservoir 202 through a channel 209 at the base that is sized to control the fluid flow.

The third main component of the nasal irrigator is the cover 211 that mates with the reservoir 202 of the main canister 201 and extends over the insert 206 such that the insert does not contact the nose as the device is inserted into the nasal cavity, thereby ensuring that the hole 210 in the insert 206 and the hole 204 in the air exit port 203 remain concentrically aligned. The cover 211 includes a mating surface 212 that creates a preferably isodiametric connection to the main canister 201 and extends around the nozzle formed by the insert 206 and air exit port 203. The cover 211 extends just above the insert 206 and has its own exit hole 214 designed not to restrict the flow of the aerosol plume. In one embodiment, the cover 211 provides a cross member or other feature that secures the insert 206 to prevent lifting of the insert at the initiation of atomization.

Figure 7:
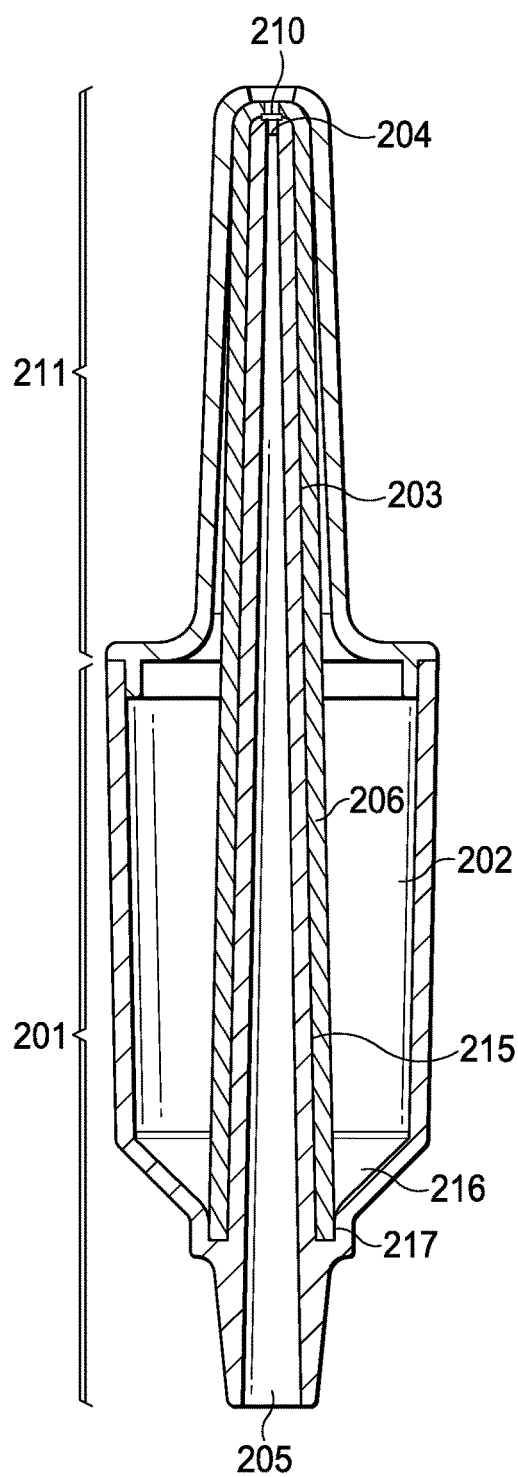

FIG. 7 is a schematic cross section view of the assembled nasal irrigator in accordance with the present invention. This view shows the alignment of the canister 201, insert 206, and cover 211 and the resulting fluid space 215. When fluid is in the reservoir 202 and a pressurized air source is introduced to the system via air inlet 205, a vacuum is created in the space 215 as air exits through outlets 204 and 210. Because the aerosol exit hole 210 in the insert 206 is larger than the exit hole 204 of the air exit port 203, when air is forced through the air exit port 203 at an appropriate volume and speed it creates a venturi effect as the pressurized gas is expelled, thereby drawing fluid in the reservoir 202 up into the space 215 between the insert and air outlet. When the fluid reaches the airstream between the exit holes 204, 210, it is atomized in the airstream to create an aerosol. This aerosol is sufficiently dispersed within the nasal cavity above the inferior turbinate so as to the reach the upper nasal cavity.

The aerosol exit 210 in the insert 206 is small enough to ensure that a mist is created yet large enough to ensure that the hole can be chamfered on the outer side to reduce agglomeration of the mist particles upon exit. The aerosol exit hole 210 is chamfered so that the walls of the exit are angled away from a central axis of the hole such that the angle is greater than that of the aerosol plume. This chamfering reduces agglomeration of particles on the walls of the aerosol exit hole 210, resulting in uniformity of particle size across the resultant aerosol plume.

The base of the insert 206 sits in a groove 217 at the base of the canister 201, ensuring that all fluid is drawn from the bottom of the canister.

The irrigator components of the present invention can be made from materials such as rigid plastic, glass, metal, ceramic, carbon fiber or other rigid material, an elastomer plastic, or some combination thereof.

Figure 8:
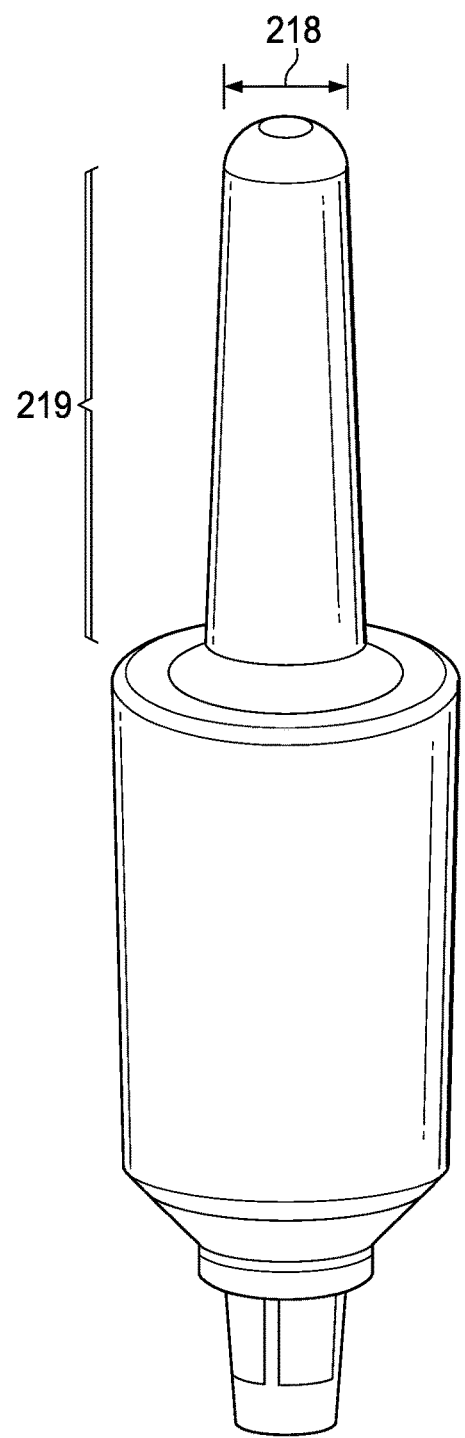

FIG. 8 shows a perspective view of an assembled nasal irrigator in accordance with the present invention. By maintaining a sufficiently narrow nozzle assembly 218, and a sufficiently long and smooth cover 219, the device can be easily and atraumatically inserted into the nose of the patient so that the nozzle 218 extends to or above the nasal valve. The device is then angled by the user to obtain the best distribution based on the user's anatomy. The mist enters the nasal cavity independent of the patient's breathing.

The nasal irrigator of the present invention may also include a feature that guides the user to angle the spray into the nose to a set angle of between 0 and 90 degrees from the vertical plane of the face (defined as the front of the face from the chin to the forehead). For example, one embodiment of the nasal irrigator includes a setoff that sets a specific angle of 30 degrees from the vertical plane of the face. In another embodiment, the setoff angle is 60 degrees from vertical, and in another embodiment the setoff angle is 45 degrees from vertical. The setoff described above is removable to accommodate various size faces and noses.

The method of nasal irrigation of the present invention uses a variable particle size up to 100 microns under a pressure of 1-15 psi (0.069-1.0345 bar), creating a pressurized airflow that enables the resultant air-mist stream to reach the whole nasal cavity independent of the patient's breathing. The resultant aerosol mist reaches the area of the nasal cavity above the inferior nasal turbinate or chonchae to ensure that the mist reaches the areas of the sinus ostia to clear this area of the nasal cavity and enable the natural mucociliary flow to clear the sinuses.

By adjusting the size of the exit holes 204 and 210, the air-fluid mixture can be calibrated to achieve nasal irrigation within a short period of time, without the need for the fluid to exit the nostrils at the time of irrigation, and with a particle size that is designed to loosen the mucous or to enter the sinus cavities, as desired by the end user. In many applications, ideally a mist of 20 microns is delivered at a rate of 0.5 ml per second.

The aerosol mist itself is typically medicated with at least one, and often two or more therapeutic agents. Possible therapeutic agents for use in the medicated mist, either alone or in combination include antibiotics, antifungal agents, corticosteroids and mucolytic agents. The mist may also be medicated with a neurologically-active agent targeting the central nervous system through the cranial nerves innervating at least a portion of the nasal cavity as well as systemically-active agents.

Figure 9A:
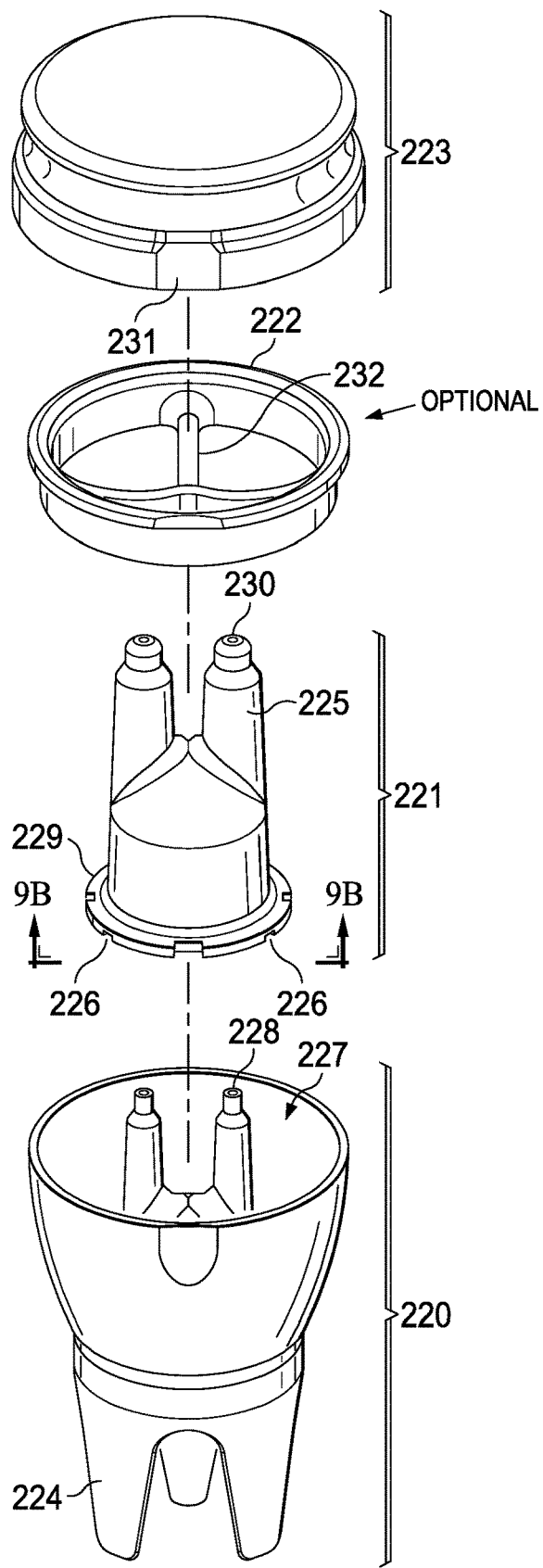
Figure 10:
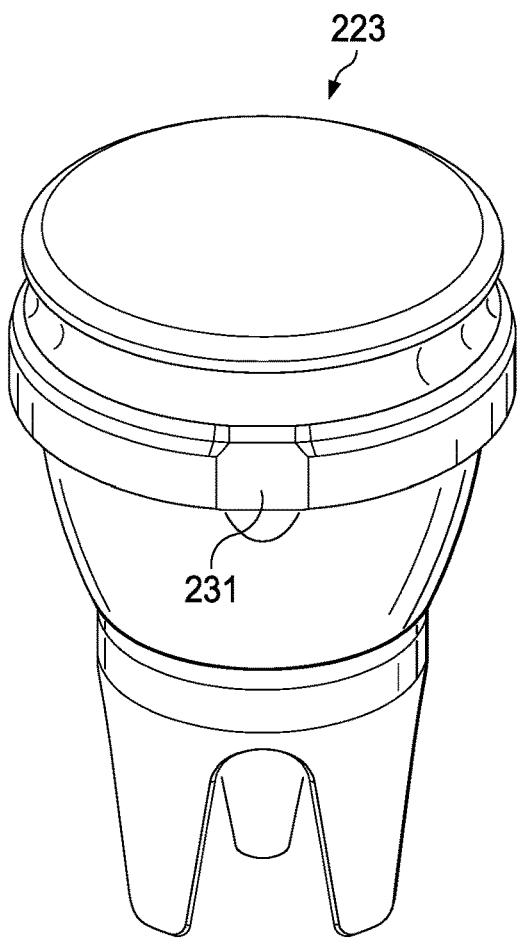
Figure 11:
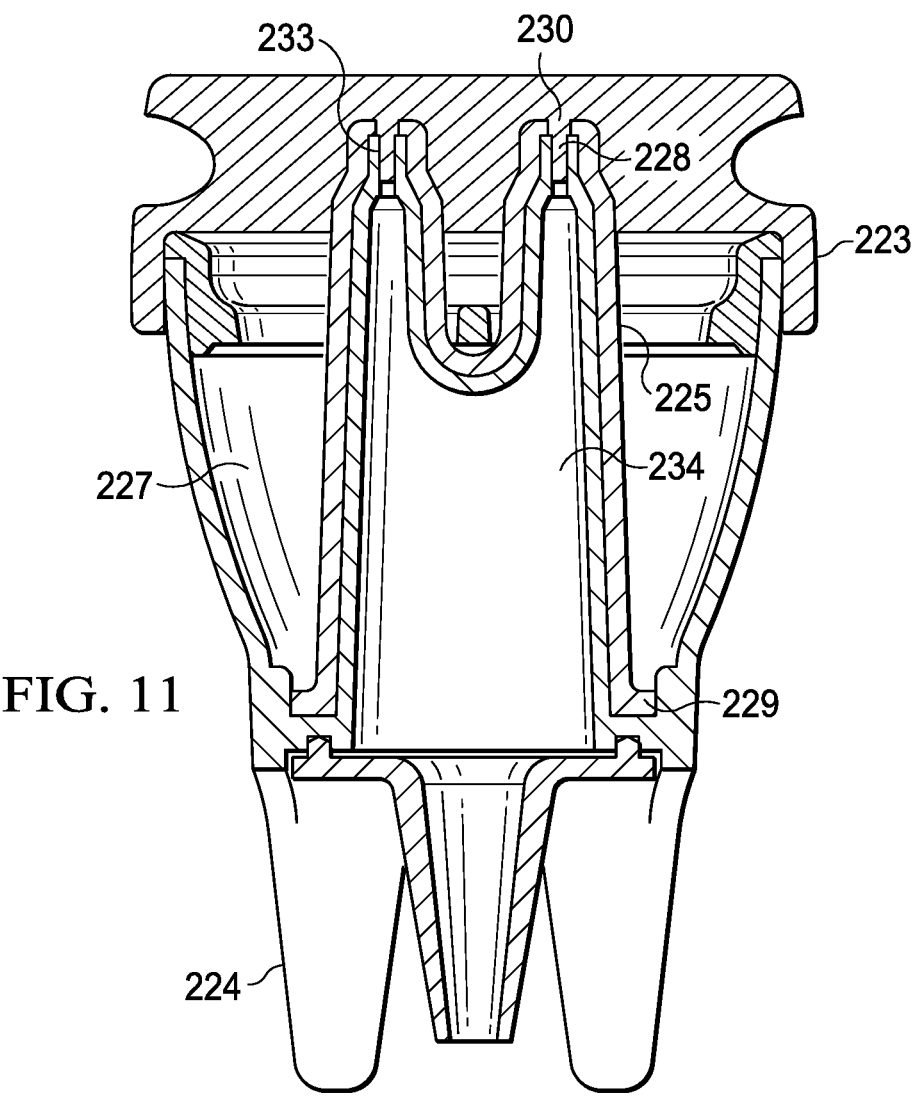
Figure 12B:
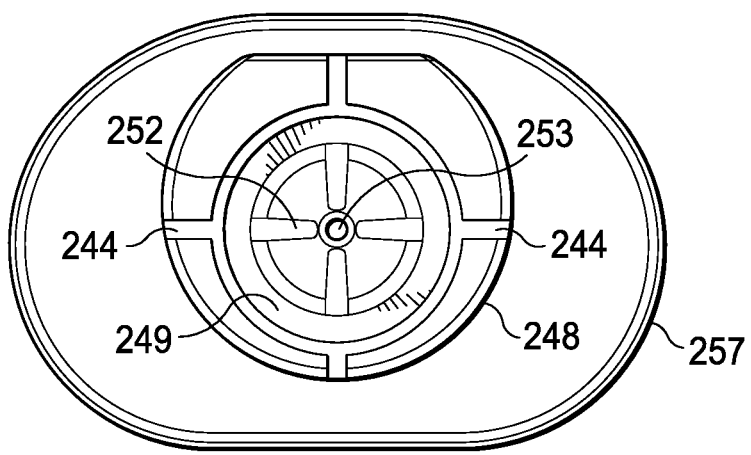
Figure 13A:
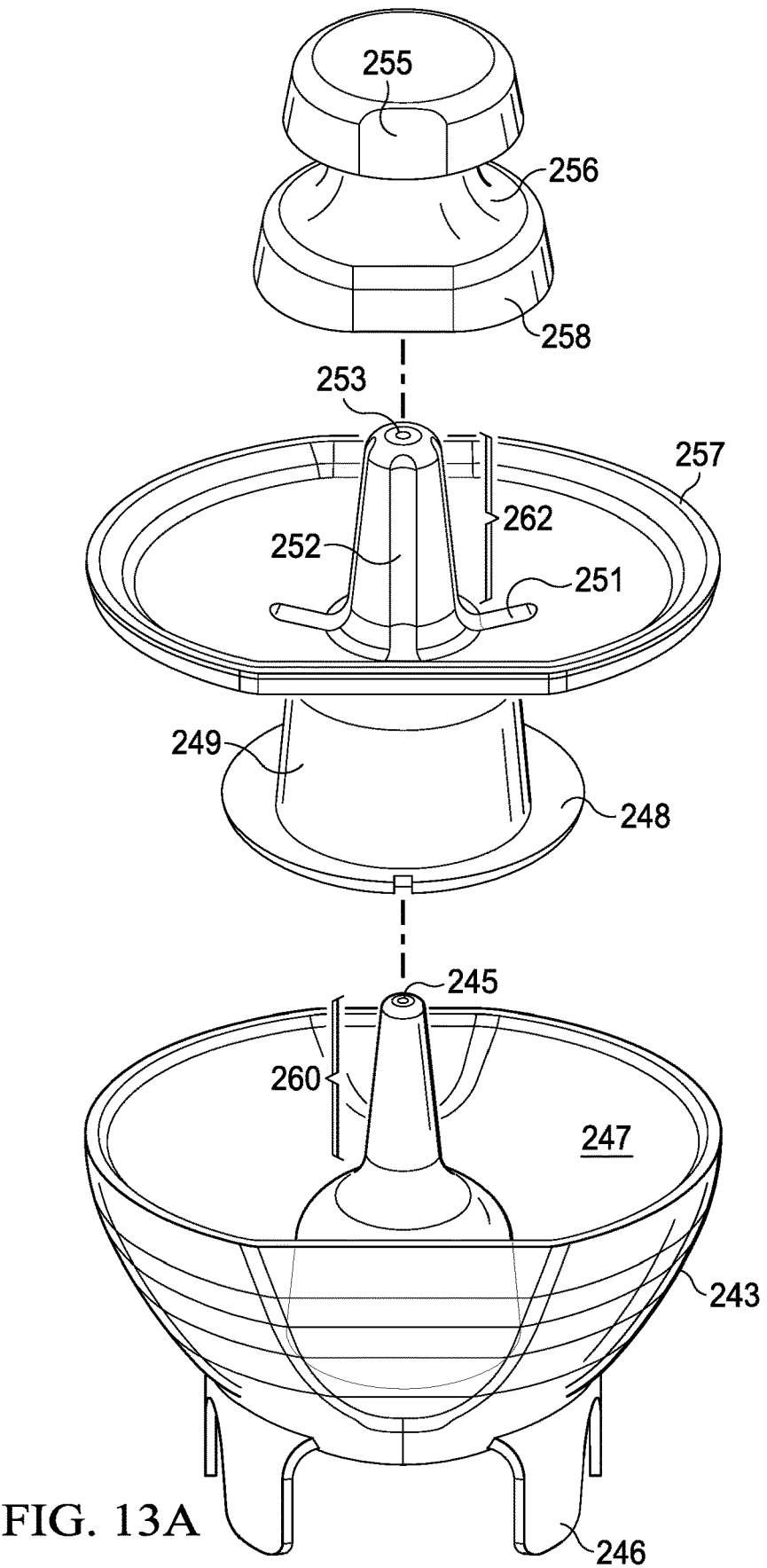
Figure 13B:
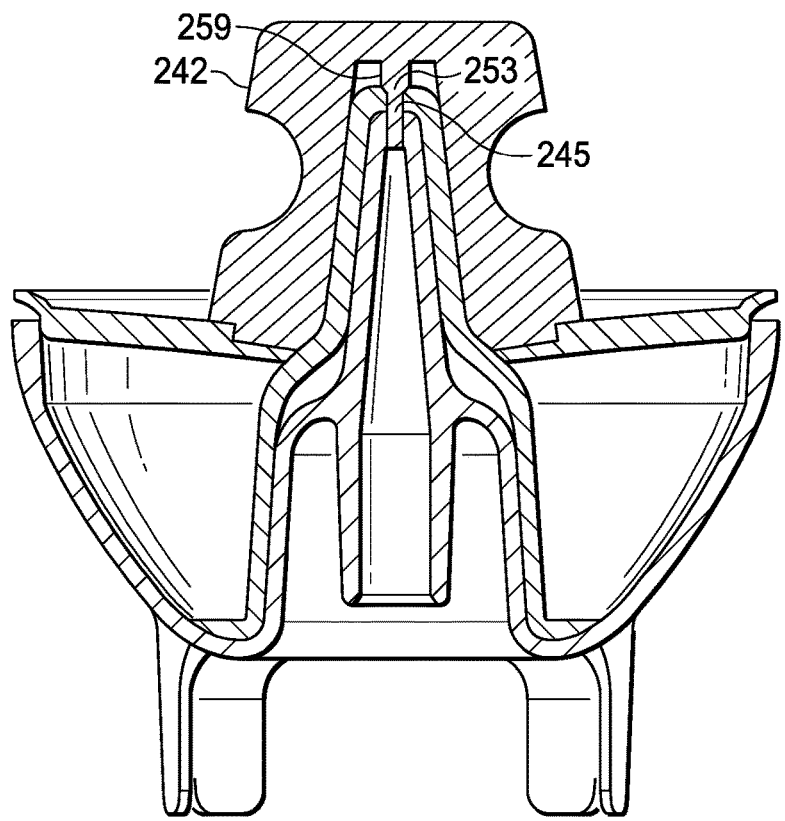
Figure 14:
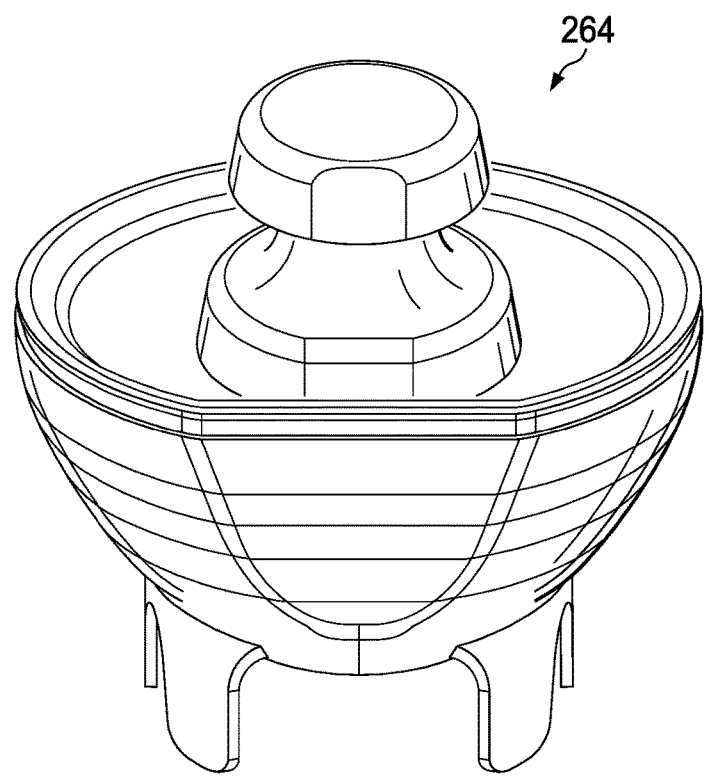
Figure 17:
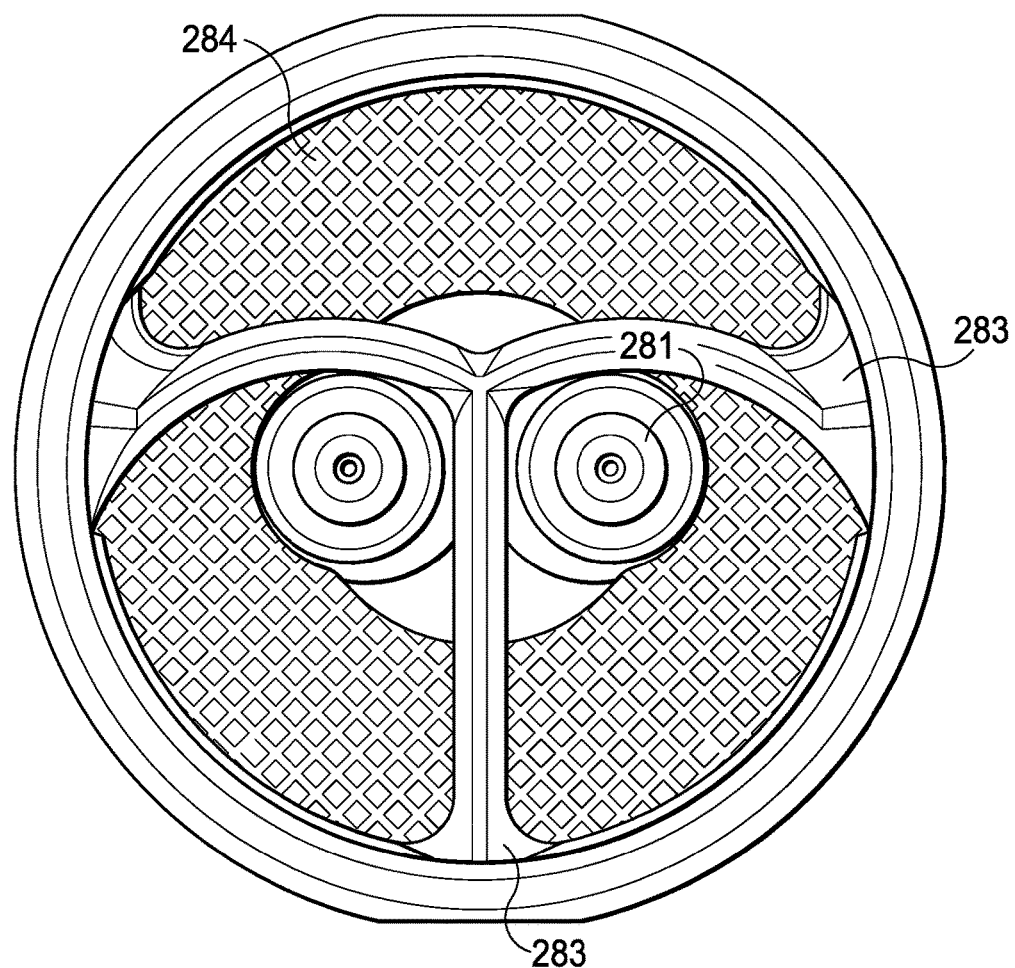
Figure 18:
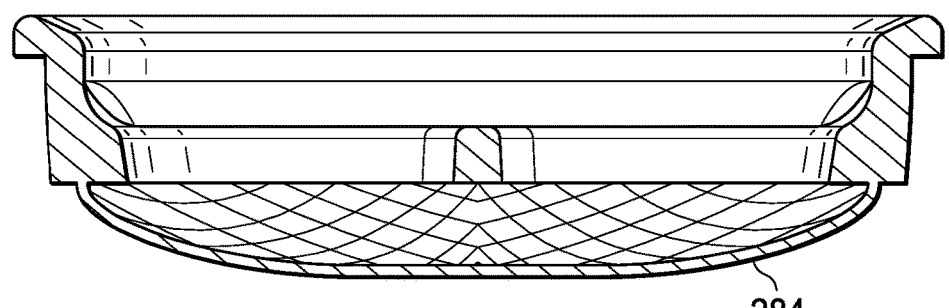

FIG. 9a is an exploded view of an improved nasal irrigator device according to one embodiment of the present invention. The device comprises a main canister 220, an insert 221, and a cap 223. The main canister 220 and the insert 221 comprise many of the same characteristics of the irrigator described with relation to FIG. 1. The main canister 220 comprises a rim surrounding a reservoir 227, which can hold up to 50 mL of fluid. While the reservoir is depicted as substantially circular, it should be appreciated that the reservoir may comprise any shape. In one embodiment, the reservoir comprises an oval shape. As previously described with respect to FIG. 1, the main canister 220 also comprises an air chamber that terminates into at least one air exit port 228. In one embodiment, as depicted in FIGS. 9-11, the air chamber of the canister terminates into two air exits ports 228 (one for each nostril). In another embodiment, as best depicted in FIGS. 12-14, the air chamber of the canister terminates into only one single air exit port.

As described above with respect to FIG. 1, each air exit port 228 has at least one hole of between 0.020" and 0.060" (0.508 mm-1.524 mm) in diameter and a web-thickness or hole length of between 0.030" and 0.200" (0.762 mm-5.08 mm). In addition, as with the embodiment of FIG. 1, on the bottom of the main canister 220 is a foot section 224 that includes at least one foot for stability and an air inlet (as depicted in FIG. 11) for the admission of pressurized air to create the air stream through air exit ports 228. The foot section 224 enables the canister 220 to remain standing on its own when set on a substantially horizontal surface and is designed to fit into a standard docking port of an air compressor pump to enable the device to remain upright in a hands-free manner so as to remain filled with the air supply tube attached.

The insert 221 comprises a base 229 that fits within the canister 220 and sits just off the bottom of the reservoir 227. In one embodiment, as depicted in FIG. 9, the base 229 is circular. However, the base may comprise any number of shapes so long as it fits within the canister. The insert 221 further comprises a fluid channel 225 that fits over the air exit port 228, said fluid channel 225 comprising a tube portion ending in a common bell housing 234 above the base. In one embodiment, the insert comprises two fluid channels. In another embodiment, described below, the insert comprises one fluid channel.

Figure 9B:
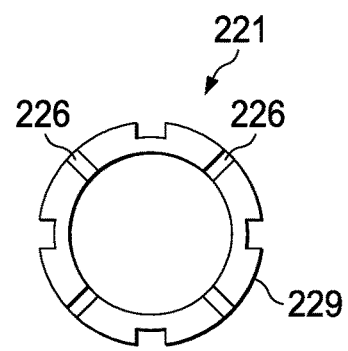

As best depicted in FIG. 9b, the bottom face of the base 229 of the insert 221 comprises at least one groove 226 that forms a communication channel between the canister and the common bell housing of the insert. The groove 226 extends from the outside of the base to the inside of the insert. The base should comprise at least one groove but may also comprise more than one, as depicted in FIG. 9b. The number of grooves as well as the width and depth of the groove will help regulate the flow of fluid up to the point that the airflow takes over the upper limit of flow. In one embodiment, the grooves may range in width from about 0.005" to about 0.150" (0.127 mm to about 3.81 mm). In one embodiment, the grooves may range in depth from about 0.001" to about 0.050" (0.0254 to about 1.27 mm). The fluid channel 225 is larger in diameter than the air exit port 228, thereby providing a small space between the outer surface of the air exit port 228 and the inner surface of the fluid channel 225 that allows fluid from said reservoir 227 to be drawn through the communication channel and upward between the air exit port 228 and the fluid channel 225 such that the fluid is expelled as a mist in an aerosol plume through an exit hole 230 in the fluid channel due to a venturi effect created by the introduction of pressurized air from the air exit port.

In one aspect, the canister 220 and the insert 221 are preferably affixed together such that the insert 221 and the canister 220 together form an integral piece. As used herein, "affix" relates to a secure attachment between the canister and insert and may include both permanent bonding and temporary bonding, which may only be subsequently manually separated. Preferably, the affixing of the insert and canister will not interfere with or negatively affect the communication channel(s) formed by the grooves in the bottom face of the insert. In one embodiment, the insert 221 is permanently affixed or bonded to the canister 220 at the bottom face of the insert. The bond may be formed by any means known in the art including without limitation use of a solvent bond, glue UV-cured adhesives, mechanical attachment, heat forming, or radiofrequency or ultrasonic welding. In another embodiment, the canister 220 and the insert 221 may mechanically mate together, such as with a friction fit or a snap fit, to form a temporary connection between them that can be subsequently separated by the user as desired.

In yet another embodiment, where the insert comprises two fluid channels, the nasal irrigator may further comprise a cross bar component 222 having an edge that fits around the rim of the canister. The crossbar component may comprise a single crossbar 232 that extends from one edge of the component 222 to another edge, dividing the component 222 into two substantially equal halves, as depicted in FIG. 9a for example; or it may comprise a crossbar that extends from one edge to one or more other edges at a different locations around the circumference, dividing the enclosed space into multiple areas. In such embodiments, the crossbar component 222 may be permanently affixed or bonded to the rim of the canister 220, thereby affixing the insert 221 to the canister 220. The bond may be formed by any means known in the art including without limitation use of a solvent bond, glue UV-cured adhesives, mechanical attachment, heat forming, or radiofrequency or ultrasonic welding.

Covering the canister 220, insert 221, and optional crossbar component 222 is a cap 223 without holes therethrough. As depicted in FIG. 10, a cap 223 fits over the rim of the canister 220 and covers the tube portion of the insert, plugging the exit hole 230 of the fluid channel 225 and the air exit port 228 to form an airtight, hermetic seal for the irrigator device, preventing the leakage of the fluid from the reservoir. The cap may further comprise an alignment feature or thumb hold 231 along its outer edge, which may align with a similar alignment feature or thumb hold on the exterior of the canister 220. Thus, the irrigator in one embodiment allows for sterile or non-sterile drug storage and serves as a carrier for the transport or shipment of medication or irrigation fluid.

FIG. 11 is a cross sectional view of an assembled nasal irrigator comprising a canister 220, insert 221, optional crossbar component, and cap 223. As best shown here in FIG. 11, the cap 223 may comprise sealing plugs 233 recessed within the cap, which extend through both the exit hole 230 of the fluid channel 225 and the air exit port 228. In one embodiment, the sealing plugs 233 may be comprised of an expandable material, which will expand once removed from the top of the irrigator device. In another embodiment, the cap may be threaded and include a gasket to form a compression seal. When ready for use, a user can remove the cap and connect an air supply to the air inlet beneath the reservoir.

A method of forming a disposable nasal irrigator in comprises the steps of providing a canister 220 with an air exit port 228 and a rim surrounding a reservoir 227 for holding fluid; providing an insert 221 with a base 229 that fits within the canister 220, the insert 221 comprising a fluid channel 225 that fits over the air exit port 228, said fluid channel comprising a tube portion ending in a common bell housing 234 above the base, said base comprising at least one groove 226 along its bottom face forming a communication channel between the reservoir 227 of the canister 220 and the common bell housing 234, wherein the fluid channel 225 is larger in diameter than the air exit port 228, thereby providing a small space between the outer surface of the air exit port 228 and the inner surface of the fluid channel 225 that allows fluid from said reservoir 227 to be drawn through the communication channel and upward between the air exit port 228 and fluid channel 225; and affixing the canister 220 together with the insert 221, thereby forming one integral structure.

The providing steps (a) and (b) can comprise the step of manufacturing the canister or the insert, or both the canister and the insert. The manufacturing can be performed by any means known in the art including without limitation molding, forming, shaping or any combination thereof. The providing step (a) may also comprise the step of obtaining the canister from any manufacturer or vendor, for example. Similarly, the providing step (b) may comprise the step of obtaining the insert from any manufacturer or vendor. By way of example, in one embodiment, the insert may be permanently attached to the canister along its base 229. Preferably, the bond would be formed such that the groove 226 remains a communication channel. Thus, the bonding should not substantially block or plug the groove 226. In one embodiment, the insert is bonded or permanently attached along its bottom face to an interior side of the canister. A suitable solvent bond includes, for example, any plastic adhesive including without limitation ABS, acrylic, polystyrene, and polycarbonate solvents such as cyclohexanone. With the insert and canister forming one integral structure, fluid may be inserted into the reservoir 227 and the cap 223 can be placed over the rim of the canister to seal the fluid within the irrigator device for transport or shipment.

Figure 12A:
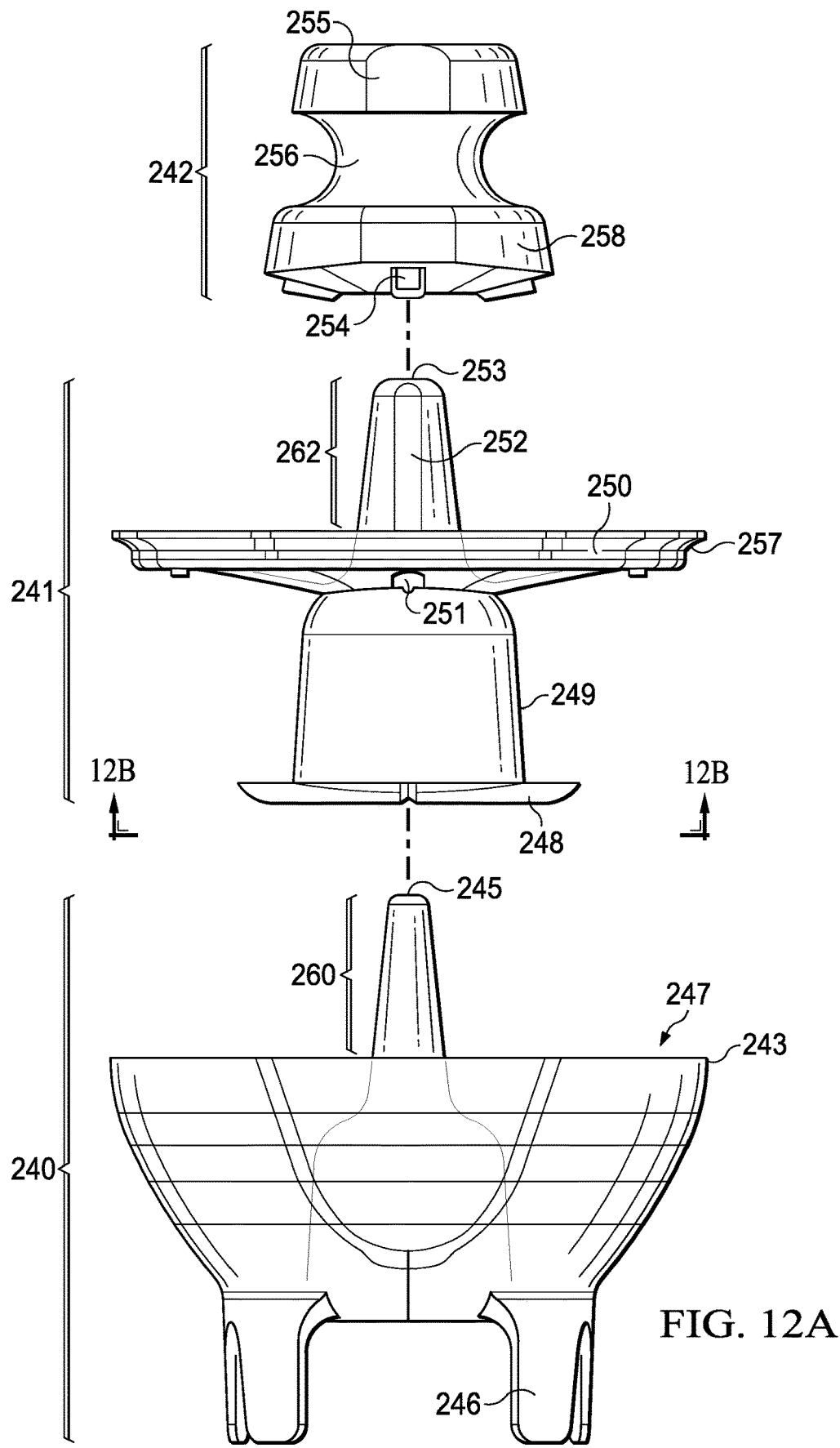

FIG. 12a depicts an exploded view of another embodiment of a nasal irrigator. Similar to the above devices, the nasal irrigator comprises a main canister 240 with an air exit port 245 and a rim 243 surrounding a reservoir 247 for holding fluid. The air exit port 245 extends beyond the rim 243 of the irrigator and has at least one exit hole at the top sufficient to deliver an airstream that is able to atomize fluid and deliver an aerosol. The main canister may also comprise the foot section 246 for stability. In addition, if desired, the canister may comprise one or more horizontal marks or lines to indicate specific fluid levels.

FIG. 12*b* depicts an embodiment of the insert 241 with a base 248 that fits within the main canister 240, wherein the insert has a bottom face with at least one groove 244 to form a communication channel between the canister 240 and the common bell housing 249. In one embodiment, as depicted in FIG. 12*b*, the groove at the bottom of the insert 241 may extend from the outside edge of the bottom face to a peripheral groove surrounding the opening of the common bell housing. The insert further comprises an extension 250. As depicted in FIGS. 12*a* and 13*a*, in one embodiment, the extension 250 protrudes outwardly from the mid-section of the insert 241 above the common bell housing 249. In other embodiments, however, the extension may also extend from another point along the insert, from the common bell housing to any point closer to the exit 253 of the fluid channel. The extension 250 forms a top, or lid, to the canister 240 that mates with the rim 243 of the canister. In one embodiment, the extension comprises a downward concave shape relative to a plane substantially perpendicular to the fluid channel; or, relative to the top surface of the lid. In one embodiment, the extension comprises a two-step diameter 257 to mate with the rim 243. The insert 241 further comprises one or more apertures 251 around the fluid channel, each of the apertures lining up with a vertical groove 252 along the exterior of the fluid channel 262. The groove 252 runs vertically from a point below the exit hole of the fluid channel 253 down to an aperture 251 in the extension 250. During use, the deflected fluid will begin to flow back down the vertical groove 252. The aperture 251 communicates with the inner chamber formed by the mating of the main canister 240 and insert 241. As fluid exits the inner reservoir, a vacuum is created that actually pulls the deflected fluid back into the reservoir 247 through the aperture 251, thereby ensuring maximum usage and minimized waste of the fluid.

The irrigator further comprises a cap 242 without holes that fits over and inserts into the fluid channel 253 and the air exit port 245 to seal the reservoir from the air exit and fluid exit. The cap comprises an elongated portion 256 to ensure a good fit over the tube portion. Optionally, the cap may comprise a flattened edge 255 to help with alignment with the apertures 251 of the insert 242 and also help with the grasping the cap 242. The bottom portion 258 of the cap mates with a portion of the top face of the extension. Thus, as best depicted in FIG. 12*a*, the bottom face of the cap 242 is relatively upwardly convex in one embodiment to mate with the downwardly concave extension 250. The cap 242 further comprises one or more projections 254 on its bottom face, which mates with the apertures 251 of the extension. In particular, the projection 254 aligns with and seals the aperture 251 when the cap 242 is placed over the insert 241, as best shown in FIG. 14. Thus, the number of projections 254 on the bottom face of the cap 242 should equal the number of apertures 251 in the insert 250. As best depicted in FIG. 13*b*, the cap further comprises a sealing plug 259 that projects into and fits within the exit hole of the fluid channel 253 in the insert 241 and the air exit port 245, thereby sealing the nasal irrigator.

Similar to the embodiments described above with regard to FIGS. 9-11, in order to make a disposable device in accordance with one aspect of the present invention, the canister 240 and the insert 241 are affixed together such that the insert 241 and the canister 240 together form an integral or single piece. In embodiments comprising an extension 250 extending from the insert to the rim of the canister (as depicted in FIGS. 12-13), the extension may form a top that mates with the rim of the canister and the edges of the extension may be permanently affixed to the rim of the canister. Thus, in one embodiment, it is the extension that is permanently affixed to the rim of the canister by way of bonding, for example. In another embodiment, the extension may form a top that mates together with a portion of the canister. A suitable solvent bond includes, for example, any plastic adhesive including without limitation ABS, acrylic, polyacetal, polyethylene, polyester, polypropylene, polystyrene, or polycarbonate solvent, UV-cured adhesive, heat or ultrasonic welding or over molding of materials. Bonding with such materials can be performed by any means known in the art. Having the insert and canister as a single integral piece, fluid may be inserted into the reservoir 247 and the cap 242 can be placed over the exit hole 253 and the aperture(s) 251 of the insert 241 to seal the fluid within the irrigator device for transport or shipment. The cap sits over the tube portion of the fluid channel and the fluid within the reservoir remains sealed within the irrigator device until ready for use. FIG. 14 depicts an assembled, sealed device 260 ready for transport.

As with the above embodiments, the orifices of the fluid channels should be positioned relative to the air exits so as to create a venturi effect with the pressurized gas expelled from the gas tubes. Thus, the affixing step should account for this positioning. Because the fluid channel exits in the insert are larger than the air exits, when air is forced through the air exits at an appropriate volume and speed, fluid in the reservoir is drawn up into the space between the insert and air exits ports. When this fluid meets the subsequent airstream it is atomized into particles conducive to deposition in the upper airway.

FIG. 15 is an exploded view of an embodiment of a nasal irrigator device comprising a canister section 270, an insert 271, and a filter 272. Similar to the above devices, the canister section 270 comprises a canister 273 with reservoir 275 and an air exit port 276 having an exit hole 277. The canister section 270 also comprises one or more feet 274 beneath the canister 273; and the insert 271 comprises a base 278 that fits within the reservoir of the canister and at least one fluid channel 280 with an exit hole 281. As described above, the insert and canister section once formed, shaped, molded or obtained, are affixed to one another.

In one embodiment, the nasal irrigator device further comprises a filter component 272 that may be inserted over the insert 271. The filter component 272 comprises a filter 284 comprised of a mesh structure with holes small enough to prevent any particulate matter or mucus that runs out of the nose from entering the reservoir 275, while allowing the irrigating or medicating fluid to run back into the reservoir 275 to be re-circulated or re-used. Suitable materials from which to create the filter are plastic, metal, carbon fiber, or other fiber. In embodiments comprising more than one fluid channel, the filter component also comprises a crossbar component 283. In one embodiment, the crossbar 283 is an integral part of the filter component 272. However, it should be understood that the crossbar 283 could also form a separate component, which is detached from the filter, and remains optional.

FIG. 16 is a perspective view of an assembled irrigator having an insert having two fluid channels 280 and a filter 284 with the optional crossbar 283, wherein the insert is affixed to the canister to form one single integral structure. As described above, in one embodiment, the insert is affixed to the canister by way of bonding. The bonding may comprise the joining of the bottom face of the insert base to the canister or the joining of the periphery of the base to the canister. In one embodiment, the insert may be affixed to the canister by permanently bonding the periphery 282 of the filter to the rim of the insert. As best depicted in FIG. 17, the filter 284 surrounds the tube portion 280 of the insert and extends from the rim of the canister to the tube portion 280, substantially covering the opening of the canister such that when in use, the filter prevents particulate matter from entering the reservoir.

With reference to FIGS. 12 and 13, where the nasal irrigator comprises an extension, in one embodiment, a filter entirely covers or fits within the apertures 251 in the extension 250 to similarly keep particular matter out of the reservoir and separate from the fluid for re-circulation. The filter may slide over the fluid channel of 241 or may be bonded over or under the apertures 251 or even molded into the insert 241.

FIGS. 19A and 19B show an exploded view of a portable nasal irrigator in accordance with an embodiment of the present invention. The portable irrigator comprises four sections. The first major section is the main canister 300, which comprises a reservoir 305 for receiving fluid. The main canister 300 further comprises an air exit port 301. As depicted in the figures, the air exit port 301 may extend above the top edge of the main canister 301. However, in alternate embodiments (not shown), the air exit port 301 may be even with or recessed within the edge or portions of the edge of the main canister 300. While the reservoir is depicted as substantially circular, it should be appreciated that the reservoir may comprise any shape. In one embodiment, the reservoir comprises an oval shape. Preferably, the reservoir should be shaped to allow for the receipt of a maximum amount of fluid.

Returning to the embodiment depicted beginning at FIG. 19A, the main canister further comprises a curved wall 302 surrounding the opening to the reservoir 305. The curved wall 302 comprises a convex shape that extends downwardly around the periphery of the opening into a bottom generally rectangular opening configured to mate with a pressurized air supply, as further discussed below. When viewed from below, the main canister 300 thus comprises a generally hollow portion surrounding the reservoir portion 305.

The second major section of the portable irrigator is the insert 307, which comprises a base 308 that fits within the reservoir section 305 of the canister. As depicted in FIGS. 19A and 19B, the base 308 is circular. However, the base may comprise any number of shapes so long as it fits within the canister. The insert comprises a fluid channel 309 with one end at the bottom of the reservoir 305 and one end that is positioned in the airstream so that the airstream creates a negative pressure in each tube that draws fluid into the airstream where it is atomized. The end positioned in the airstream comprises an exit hole 313. The fluid channel 309 is slightly larger in diameter than the air exit port 301 of the main canister 300, thereby providing a small space (preferably 0.0001" to 0.010" (0.00254-0.254 mm)) between the outer surface of the air exit ports and the inner surface of the fluid channels. This space allows fluid from the reservoir 305 to proceed upward between the air exit port 301 and the fluid channel 301 until being expelled by pressurized air. When the insert 307 is installed in the main canister 300, the orifice 313 of the fluid channel 301 is positioned relative to the air exit 301 so as to create a venturi effect with the pressurized gas. Because the fluid exit in the insert 313 is larger than the air exits 301, when air is forced through the air exits at an appropriate volume and speed, fluid in the reservoir 305 is drawn up into the space between the insert and air exit port. Thus, when this fluid meets the subsequent airstream it is atomized into particles conducive to deposition in the upper airway. The airstream is sufficient to penetrate the nasal cavity above the inferior turbinate so as to deposit the fluid and provide a washing, irrigation, or deposition to the upper reaches the nasal cavity. The fluid channel size may be adjusted to change the particle size of the mist.

The insert 307 may be keyed in at least one location with the reservoir 305 to ensure that the insert does not rotate in relation to the exit port 301 of the main canister 300 and to aid in centering of the insert 307 and its fluid channel 309 on the air exit port 301. In one embodiment, the insert may also include a feature to ensure that it is inserted into the main canister in only one orientation.

At least one channel is located in the bottom of the insert 307 to act as a conduit for fluid from the reservoir 305 to enter the base 308 of the insert. As best depicted above in FIGS. 9b and 12b, the bottom face of the base 308 of the insert 307 comprises at least one channel or groove that forms a communication channel between the canister and the insert. The groove extends from the outside of the base to the inside of the insert. The base should comprise at least one groove but may also comprise more than one, as depicted in FIG. 9b. The number of grooves as well as the width and depth of the groove will help regulate the flow of fluid up to the point that the airflow takes over the upper limit of flow. In one embodiment, the grooves may range in width from about 0.005" to about 0.150" (0.127 mm to about 3.81 mm). In one embodiment, the grooves may range in depth from about 0.001" to about 0.050" (0.0254 to about 1.27 mm).

The canister 300 and the insert 307 may or may not be affixed together to form one integral piece. The bond may be formed by any means known in the art including without limitation use of a solvent bond, glue UV-cured adhesives, mechanical attachment, heat forming, or radiofrequency or ultrasonic welding. Alternatively, the canister and insert may be affixed together via a mechanical interlocking element such as a friction fit or a snap fit to form a temporary connection.

Figure 19A:
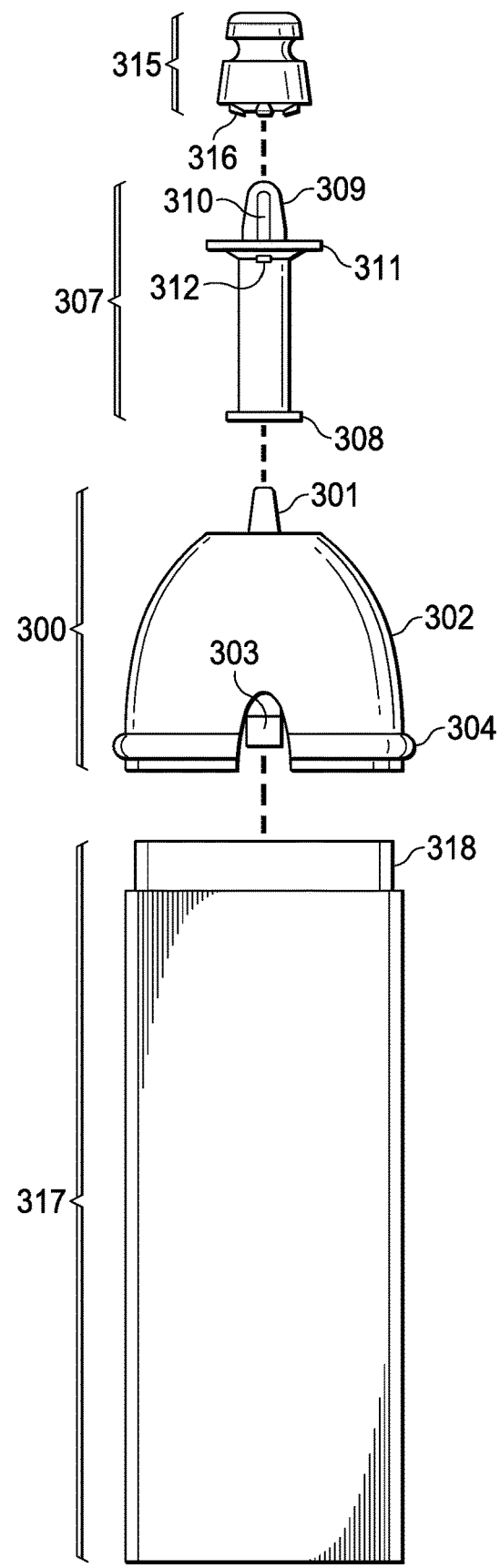
Figure 19B:
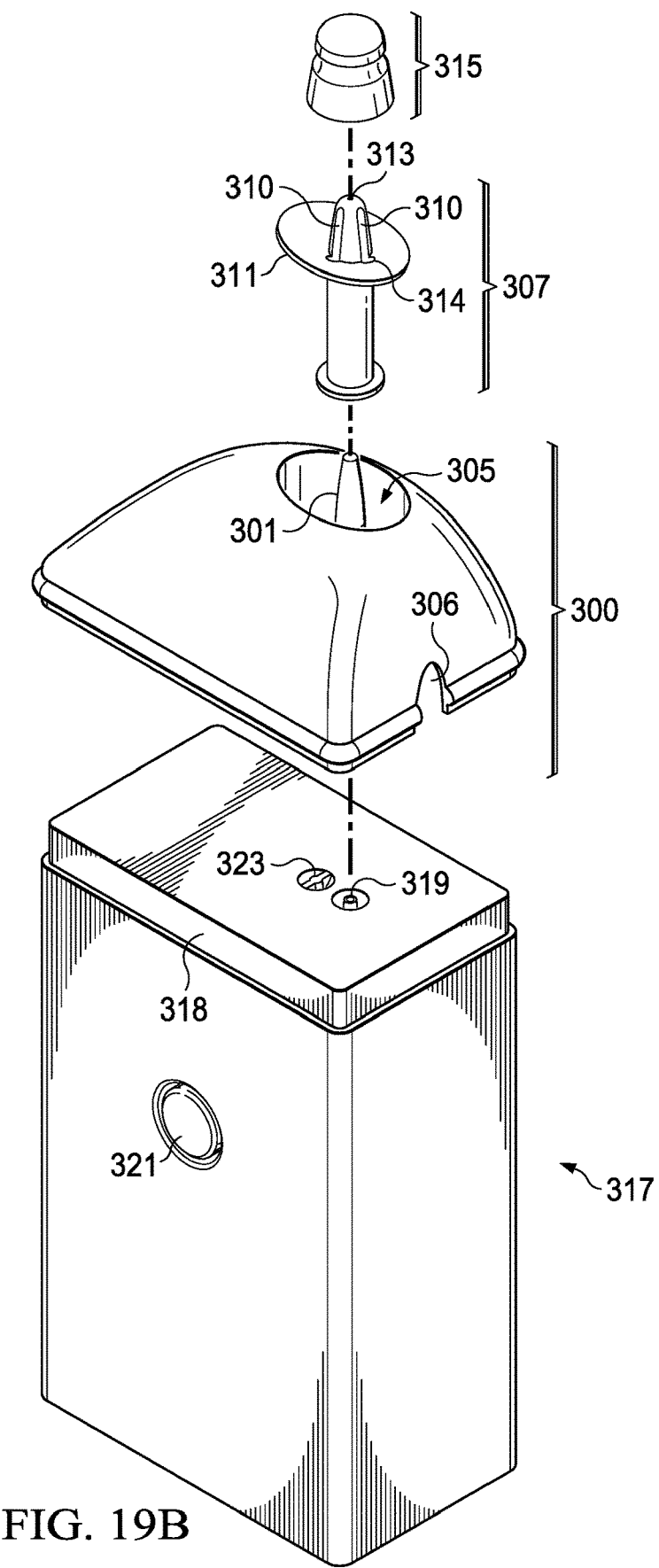

The insert further comprises an extension 311. As depicted in FIGS. 19A and 19B, the extension 311 protrudes outwardly from the insert 307. The extension 311 may extend from any point along the insert to form a top, or lid, to the canister 300. In one embodiment, the extension substantially covers the opening of the reservoir 305. In another embodiment, the extension entirely covers the opening of the reservoir 305. In one embodiment, the extension comprises a downward concave shape relative to a plane substantially perpendicular to the fluid channel; or, relative to the top surface of the lid. In one embodiment, the extension comprises a two-step diameter (not shown) to mate with a rim of the opening. The insert 307 further comprises one or more apertures 314 around the fluid channel, each of the apertures lining up with a vertical groove 310 along the exterior of the fluid channel 309. The groove 310 runs vertically from a point below the exit hole of the fluid channel 309 down to an aperture 314 in the extension 311. During use, the deflected fluid will begin to flow back down the vertical groove 310. The aperture 314 communicates with the inner chamber formed between the main canister 300 and insert 307. As fluid exits the inner reservoir, a vacuum is created that actually pulls the deflected fluid back into the reservoir 305 through the aperture 314, thereby ensuring maximum usage and minimized waste of the fluid.

Figure 22:
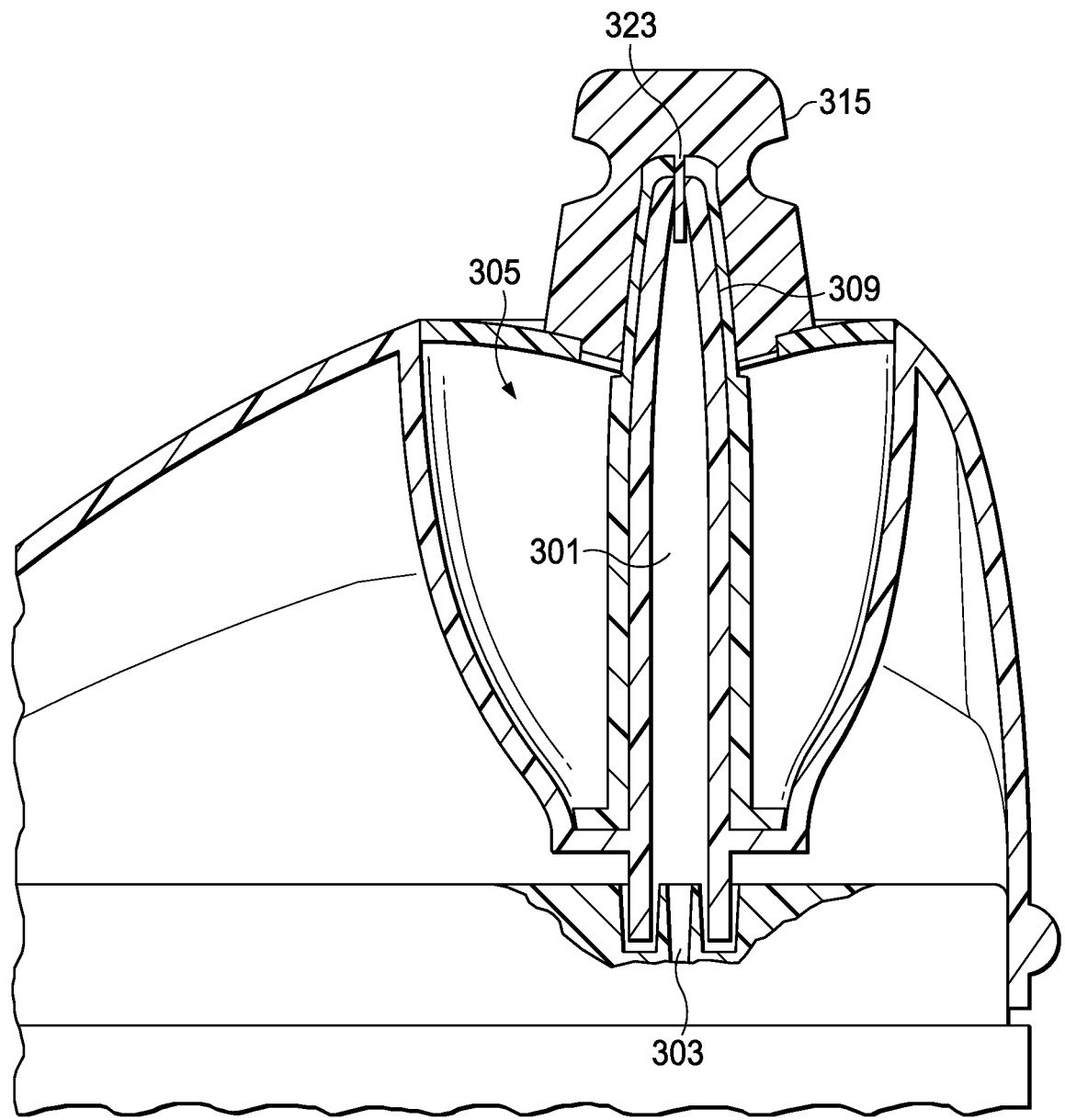

Another section of the portable nasal irrigator is a removable cap 315 of the nasal irrigator. The cap 315 comprises no holes and fits over and substantially covers the fluid channel 309. Optionally, the cap may comprise a flattened edge (as shown above in FIG. 12A) to help with alignment with the apertures 314 of the insert 307 and also help with the grasping the cap 315. The bottom portion of the cap should mate with a portion of the top face of the extension. The cap 315 further comprises one or more projections 312 on its bottom face, which mates with the apertures 314 of the extension. The number of projections 312 on the bottom face of the cap 315 should equal the number of apertures 314 in the insert 307. As best depicted in FIG. 22, the cap comprises a projection or sealing plug 323 that projects into and fits within the exit hole 313 of the fluid channel and extending into the air exit port 301 of the canister to seal the reservoir from the air exit port and fluid channel exit when the cap is placed over the insert.

A fourth section of the portable nasal irrigator is a handheld pressurized air supply source 317 onto which the main canister 300 fits. Preferably, the pressurized air supply source is a handheld air compressor. As shown in FIG. 19B, the air supply source comprises an air outlet 319, which connects with the air inlet 303 of the main canister. In one embodiment, the canister snap fits onto the pressurized air supply source 317 to form an airtight seal between the air inlet 303 and the air outlet 319. In one embodiment, the airtight seal may comprise an O-ring or soft plastic portion between the air inlet 303 and the air outlet 319 (not shown). An air input 320 supplies air to the pressurized air supply source 317 and may comprise a filter to keep out foreign materials. In order to accommodate for the air input 320, the main canister 300 comprises an air vent 306, which allows air into the air input 320 without interrupting the airtight seal between the canister 300 and air supply source 317. The bottom rim 304 surrounding the generally rectangular bottom of the main canister 300 is fashioned to fit onto the pressured air supply source 317 such that no wiring or connecting tubing is required. Thus, unlike previous embodiments, a foot section at the bottom of the main canister is not necessary in order to stabilize the canister on a substantially flat surface. Instead, the pressurized air supply connects directly and immediately with the main canister.

While the pressurized air supply source 317 is depicted as having a generally rectangular shape, the source 317 may comprise any shape so long as it remains portable and capable of directly attaching to the main canister without the use of tubing. In one embodiment, the pressurized air supply source 317 is substantially rectangular. Preferably, the pressurized air supply source comprises an ergonomic shape to increase user comfort. For example, the air supply source 317 may comprise a grasping or gripping portion having a shape that corresponds to a palm of a hand of the user. The gripping portion may be on one side of the air supply source, with a second opposing side substantially flat; or it may comprise curves substantially around the entire periphery of the air supply source such that user may hold the portable device lengthwise with his or her hand around substantially the entire pressurized air supply source 317. In one embodiment, the air supply source 317 comprises an ergonomic grasping portion. In another embodiment, the pressurized air supply source 317 is substantially rectangular with curves and features that make it easy to hold in the hand. In order to allow for portability of the irrigator device, the pressurized air supply should generally be small enough to easily carry or transport. In one embodiment, the pressurized air supply source comprises a ratio of width:length:depth of about 2.5:3:1. In another embodiment, the pressurized air supply source comprises a ratio of width:length:depth of about 9:15:5. In one embodiment, the pressurized air supply source comprises a ratio of width:length:depth of between about 2.5:3:1 to about 9:15:5. By way of example, in one embodiment, the length may be about 15.5 cm, the width may be about 9.2 cm, and the depth may be about 5.7 cm. It should be recognized that any number of sizes and dimensions is possible while maintaining portability.

The pressurized air supply source 317 may employ an AC/DC power supply. The source 317 is DC-operated and may include a rechargeable internal battery or an external, detachable battery for easy exchange of depleted batteries. The source 317 may further be operated using a power switch 321 capable of turning on the air supply. The switch 321 may be an intermittent switch conveniently located on the air supply source 317 such that a user may conveniently reach it with one of his or her fingers. In one embodiment, the air supply source 317 may also comprise an indicator for the level of charge on the battery (not depicted) or a timer that beeps at timed intervals to deliver medication evenly between nostrils (not depicted). As described above, the pressurized air has a pressure of 0.069-1.035 bar and an airflow rate of 1-12 liters per minute, producing a fluid delivery rate of 1-20 ml per minute.

Figure 20:
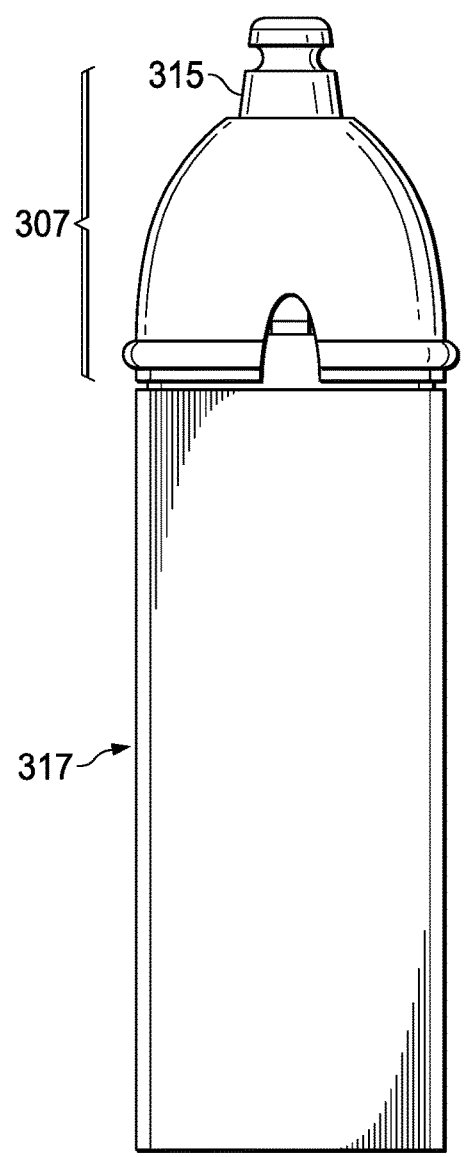
Figure 21A:
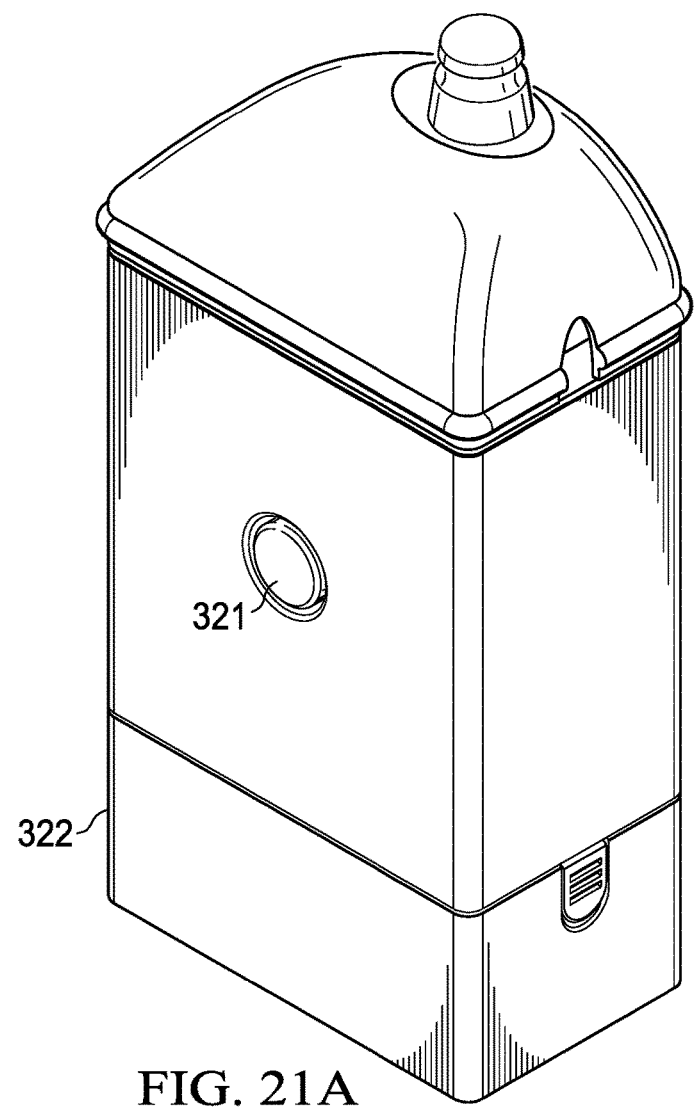
Figure 21B:
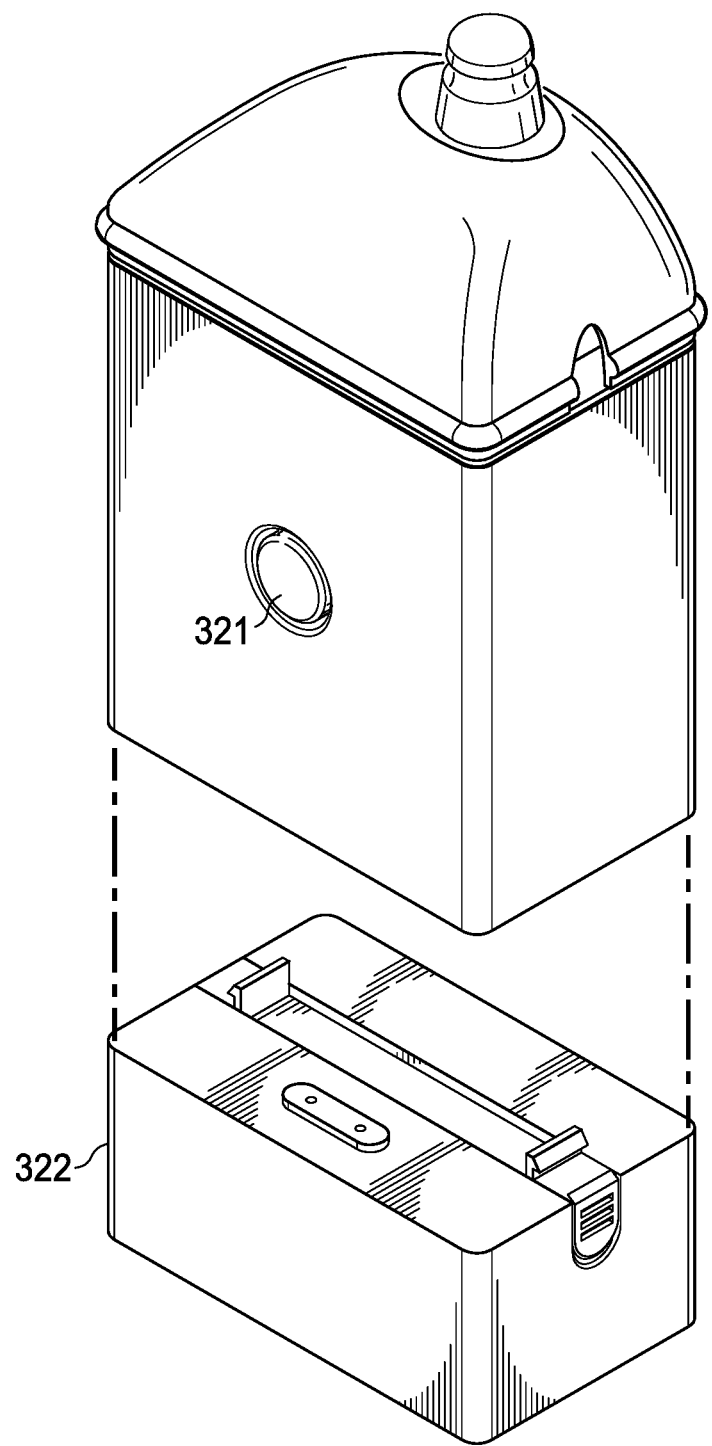

FIG. 20 shows a front perspective view of an assembled portable irrigator as shown in FIGS. 19A and 19B, with the removable cap positioned over the device. Thus, when fully assembled with the cap in place, the portable irrigator device is completely self-contained, prohibiting any leakage of fluids. As depicted in FIGS. 19A and 19B, in one embodiment, the pressurized air supply source 317 comprises an internal battery, which may or may not be rechargeable. FIG. 21A shows a perspective view of an assembled portable irrigator in another embodiment, with a detachable battery compartment 322 for one or more batteries which may or may not be rechargeable. In this embodiment, the battery compartment may detach from a portion of the pressurized air device by way of a switch element. FIG. 21B shows a perspective view of a portable irrigator as depicted in FIG. 21A, with the battery compartment 322 detached from the air supply source 317.

Figure 23:
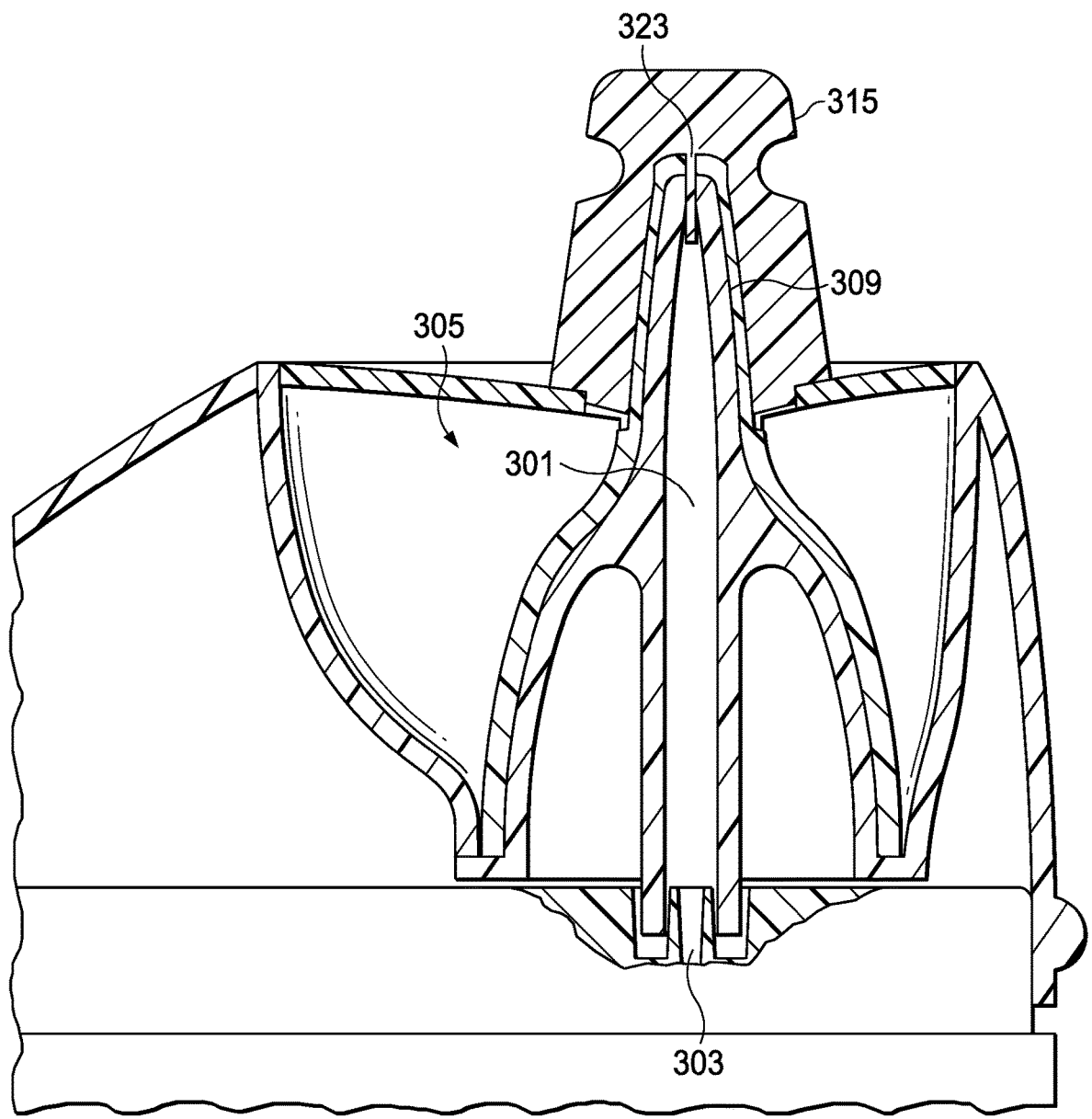

FIG. 22 shows a cross sectional detailed view of the main canister 300, insert 307 and cap 315 portions in an assembled portable irrigator according to one embodiment of the present invention. As best depicted here, the air exit port 301 and fluid channel 309 form two overlapping, concentric, tapered tubed having the requisite gap or space, as described above, between them in order to allow for the venturi effect. When connected to the pressurized air supply source 317, the air inlet of the main canister plugs directly the supply source or air compressor by way of its air outlet. An alternate embodiment depicted in FIG. 23 shows that the air exit port 301 and the fluid channel 309 may also include a common bell housing as with previous embodiments.

Figure 28:
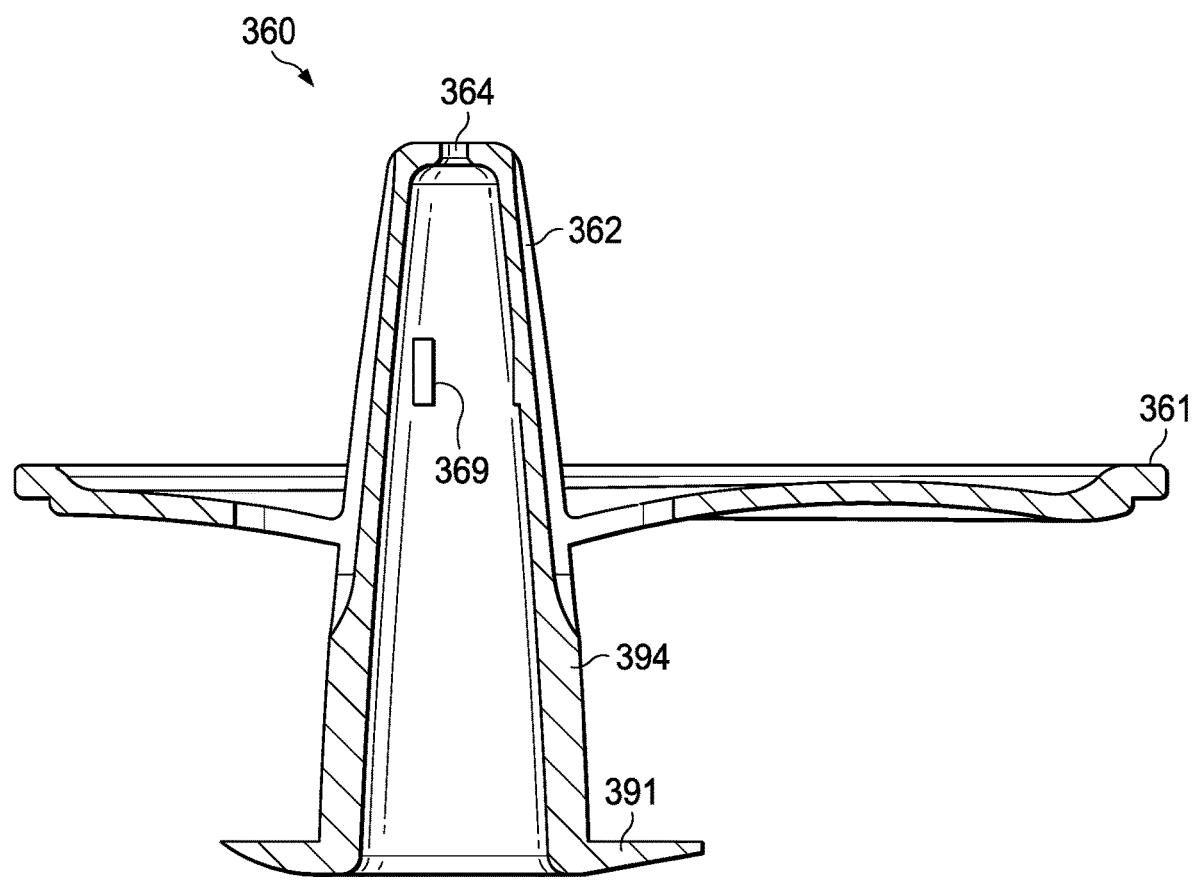
Figure 29:
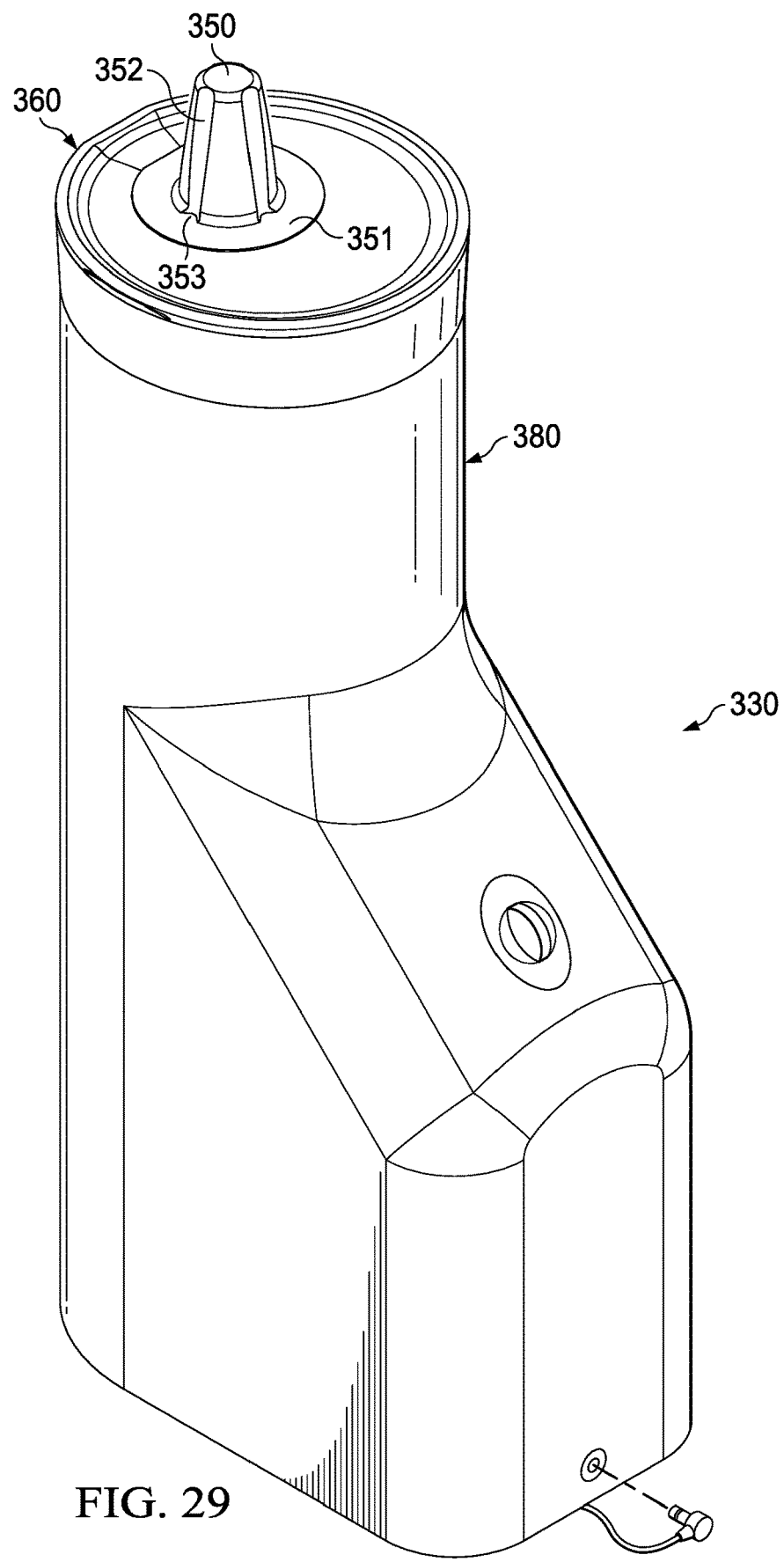
Figure 30:
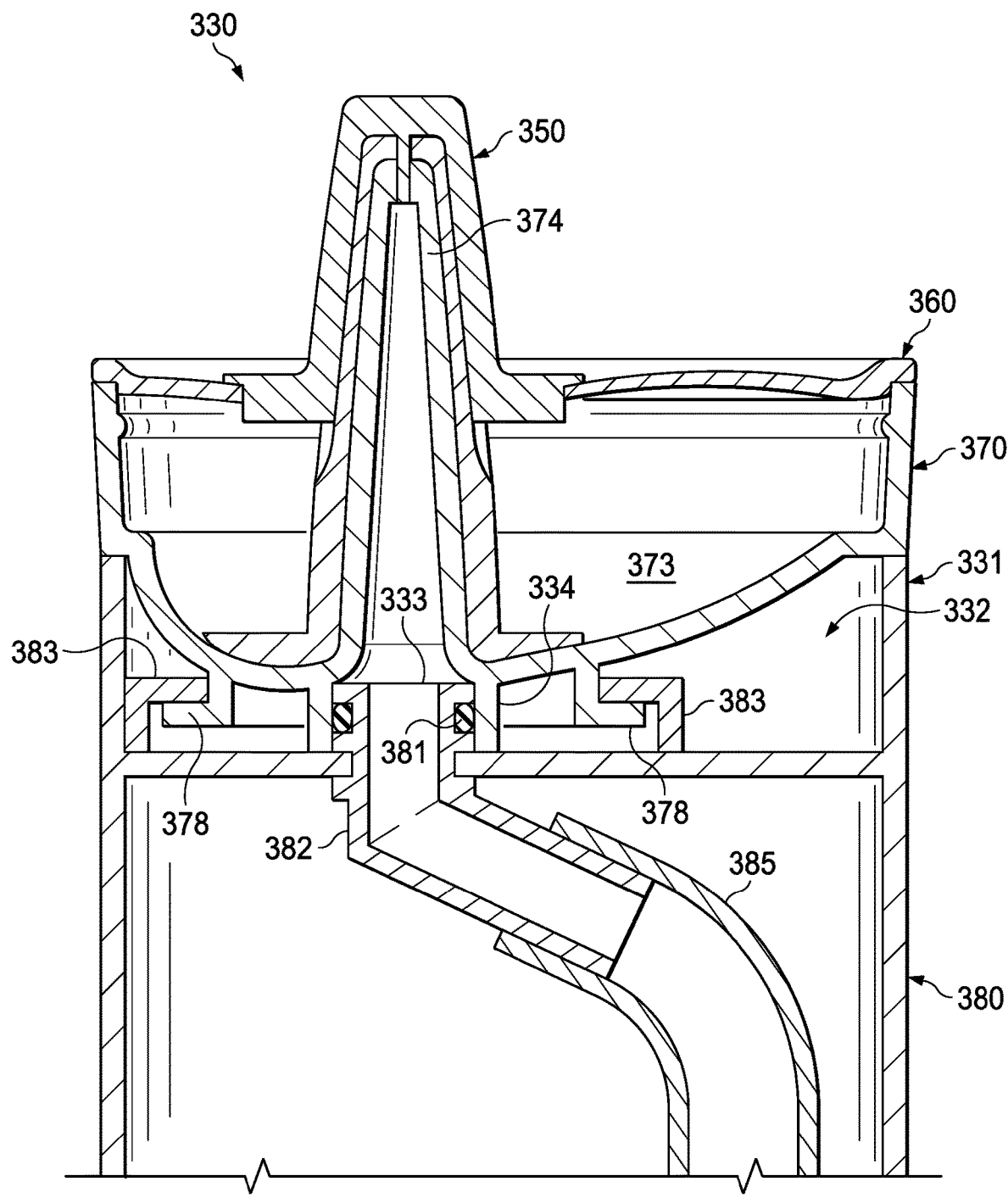

FIGS. 24-32 depict another embodiment of a portable irrigator 330. The portable nasal irrigator 330 comprises: a pressurized air supply source 380 comprising a rim 331 surrounding an opening 332 on one end with an air outlet 333 therein; a canister 370 with a reservoir 373 for holding fluid recessed within the opening 332, the reservoir 373 surrounding a tube 374 tapering to an air exit port 376; and an insert 360 comprising a base 391 that fits within the reservoir, an extension 367 above the base 391 protruding outwardly to the canister 370, and a fluid channel 394 (shown best in FIG. 25B and 28) that fits over the elongated tube 374, said fluid channel 394 having a discharge port 364 concentrically aligned with the air exit port 376, said discharge port 364 located at an uppermost end of the irrigator 330 above the extension 367, thereby providing a small space between the outer surface of the air exit port and the inner surface of the insert, creating a fluid conduit that allows fluid from said reservoir to be drawn upward between the air exit port and the fluid channel and expelled as a mist in an aerosol plume through exit holes in the fluid channel due to a venturi effect created by pressurized air from the air exit port. The fluid is thus expelled from the reservoir 373 as a mist through the discharge port 364. The canister 370 comprises: a lip 372 extending above and resting on the rim 331 of the pressurized air supply source 380; and an air inlet 334 below the reservoir 373, the air inlet 334 connected to the air outlet 333; and wherein the pressurized air supply source 380 houses an airflow regulating system. The canister 370 is retained to and sealed together with the pressurized air supply source 380 by the connection of a mating portion 383 and a tab 378, as further described below. A seal between the air outlet 333 and the tube 374 of the main canister 370 also helps maintain the connection between the canister 370 and the pressurized air supply source 380, as shown in FIGS. 26B and 30.

Figure 24:
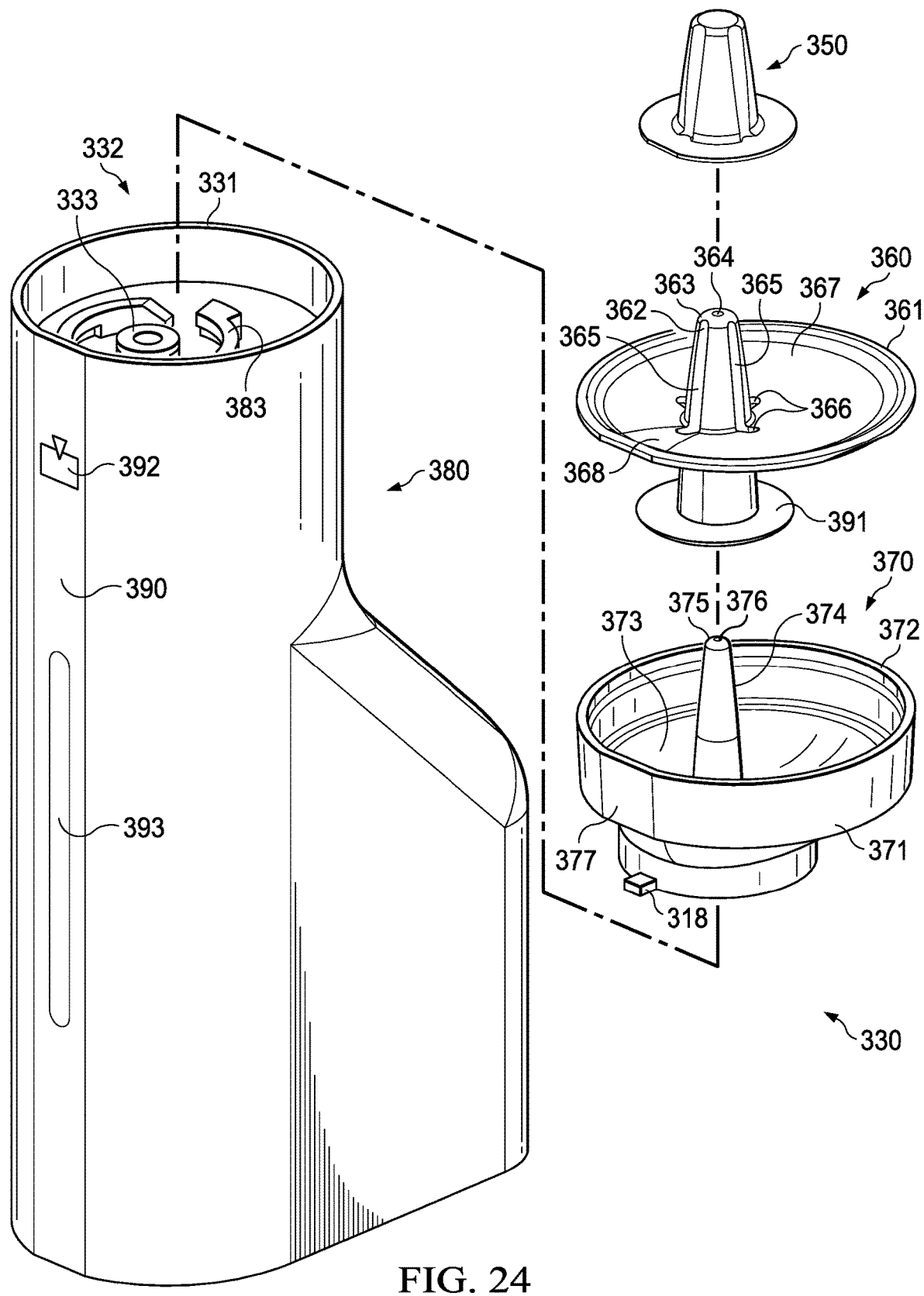
Figure 27:
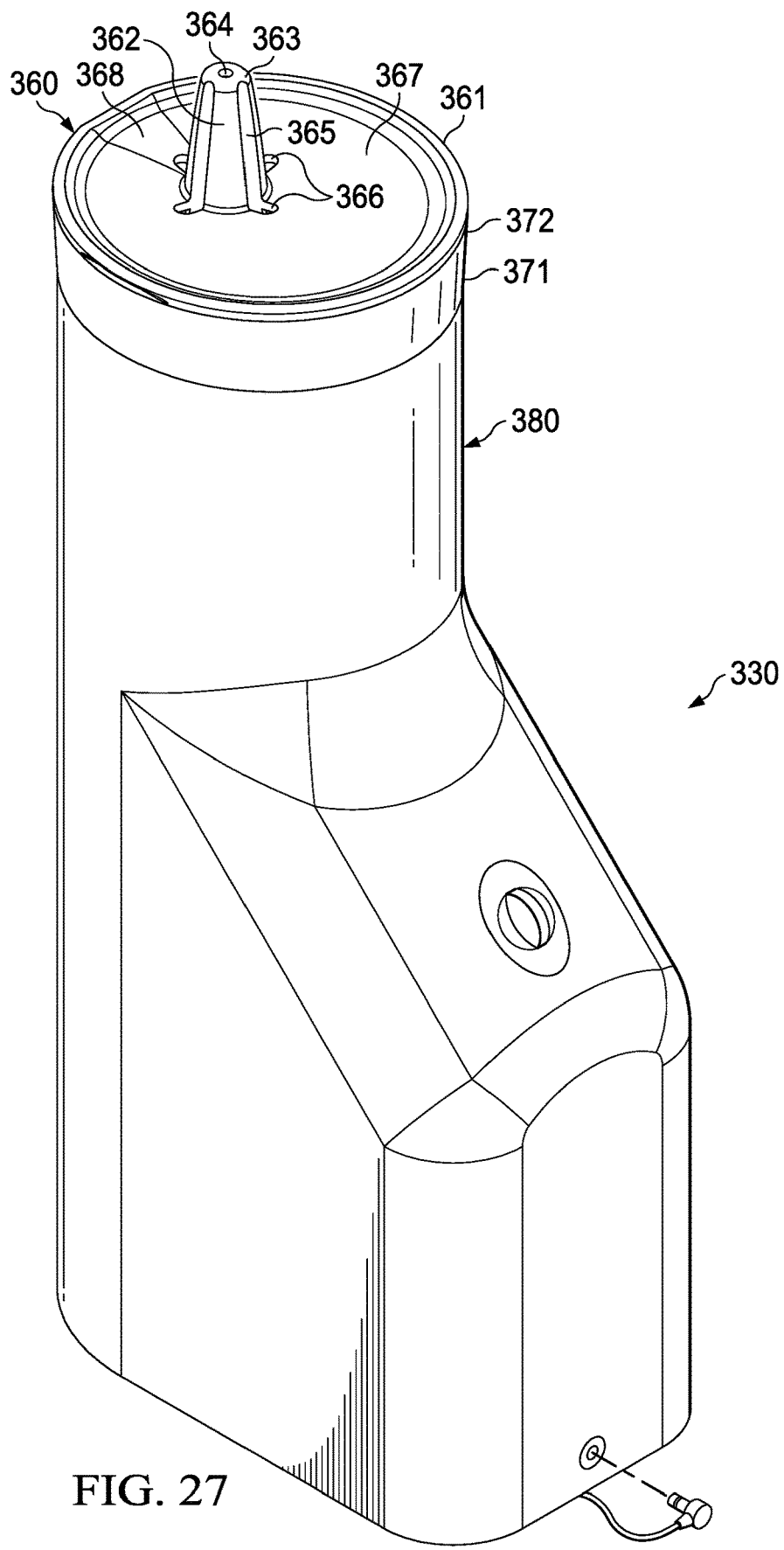

Similar to the above embodiments, the portable irrigator 330 comprises a cap 350, insert 360, and a cup or canister 370. FIG. 24 shows an expanded view of each of these components and their general placement over one another and the pressurized air supply source 380. FIG. 25 shows the canister 370 connected to the pressurized air supply source 380, while FIG. 27 shows an assembled irrigator 330 with placement of the insert 360 over the canister 370 while connected to the pressurized air supply source 380 for usage by a consumer, and FIG. 29 shows placement of the cap 350 over the insert for storage or transport by a consumer.

As depicted in FIGS. 24 and 25B, the pressurized air supply source 380 is a generally elongated structure comprising a concave opening 332 with an airflow regulating system therein, which will be further described below. In one embodiment, the pressurized air supply source 380 comprises a first larger bottom depth and a second smaller top depth, with an angled surface there between. The shape of the pressurized air supply source thus provides for a grip zone along the length of the pressurized air supply source for consumer handling. The size may be any size that allows for handheld usage. The narrow neck top accommodates single-handed use, while the wider bottom section accommodates a two-handed grip, if desired.

A single membrane 390 along one external side of the pressurized air supply source 380 incorporates a single ribbon connector (not shown) and comprises an indicator light 393, and a raised dome switch 392 integrated therein, to turn the irrigator on or off. In one embodiment, the switch 392 is an intermittent operating switch. In another embodiment, the switch is a latching switch. In one embodiment (not shown) the switch is discrete from the other components.

In the embodiment depicted in FIG. 24, the indicator light 393 comprises a light pipe, which may house one or more light therein. However, in other embodiments, the indicator light may comprise any number of shapes or symbols including, for example, any number of icons or shapes to depict battery power. By way of example, the indicator light 393 may comprise a light pipe, a battery icon, or gas gauge, which may comprise a number of rectangles in a line on the switch. An indicator light may indicate when the irrigation device is charging in one embodiment; or, when the irrigator requires charging in another embodiment; or when the device is operating, in another embodiment. The indicator light may illuminate for a sufficient amount of time for a user to recognize a need for charging after use. For example, the indicator light may illuminate for 5-30 seconds after an operation to indicate when charging is required. In one embodiment, the indicator light may illuminate to indicate when charging is needed while there is still sufficient power to run the device for a full expected dose; ensuring the user is aware of the need to charge and avoid a missed dose. In one embodiment, the indicator light is an LED light source. The LED light source may be a single color LED, multi-color LED or multiple LEDs of a single color or of different colors. In one embodiment, the indicator light uses a light pipe 393 to transmit light to the outside of the device.

In one embodiment, the single membrane 390 contains all electrical components externalized to the user except a power jack, which may be optionally used, for example, to power the irrigator or charge a rechargeable battery within the pressurized air supply source or to operate the device when the battery is discharged such that the device cannot be operated with the battery alone. In one embodiment, the irrigator comprises a tethered cover for the power jack designed to reduce fluid and dust ingress to the device when the power supply is not plugged into the device. Optionally, in one embodiment, an audible indicator is incorporated into the pressurized air supply source of the irrigator to indicate a set time of operation, a need for charging, or the initiation of a charge. On an external side, opposite to the membrane 390, the pressurized air supply source 380 comprises the angled surface having a cover or cap 450 for a filter for incoming air, further described below.

With reference to FIG. 25A, the canister 370 is recessed within the pressurized air supply source 380, which has a concave opening. More specifically, a bottom portion of the canister rests within the pressurized air supply source once the canister 370 is attached to the pressurized air supply source 380. A lip 372 extends above the pressurized air supply source 380 and rests on the rim 331 of the pressurized air supply source. In one embodiment, the lip is of an elliptical shape. The lip 372 surrounds the entirety of the top perimeter edge of the canister 370 and prevents spills from the inner volume or reservoir 373. In one embodiment, the periphery 371 is elliptically shaped to match an elliptical opening of the pressurized air supply source 380. A flat portion 377 assists with proper placement and alignment of the canister 370 in one embodiment. Thus, the pressurized air supply source 380 and the canister 370 may employ visual or tactile alignments marks to ensure the user is able to easily join the two components. As with the above-discussed irrigator embodiments, within the reservoir 373 is a tube portion 374 that tapers into an air exit port 376, which is above a rim of the irrigator. In one embodiment, the air exit port 376 comprises a size of between 0.020" and 0.060" (0.508 mm-1.524 mm) in diameter and a web-thickness or hole length of between 0.030" and 0.200" (0.762 mm-5.08 mm). In one embodiment, the canister 370 is reusable. In one embodiment, the canister 370 is disposable.

Figure 26A:
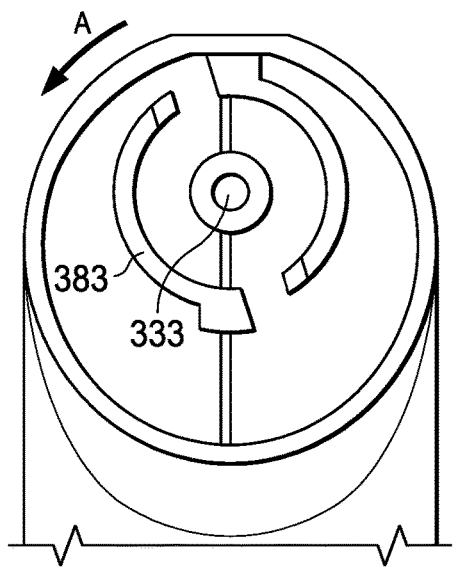
Figure 26B:
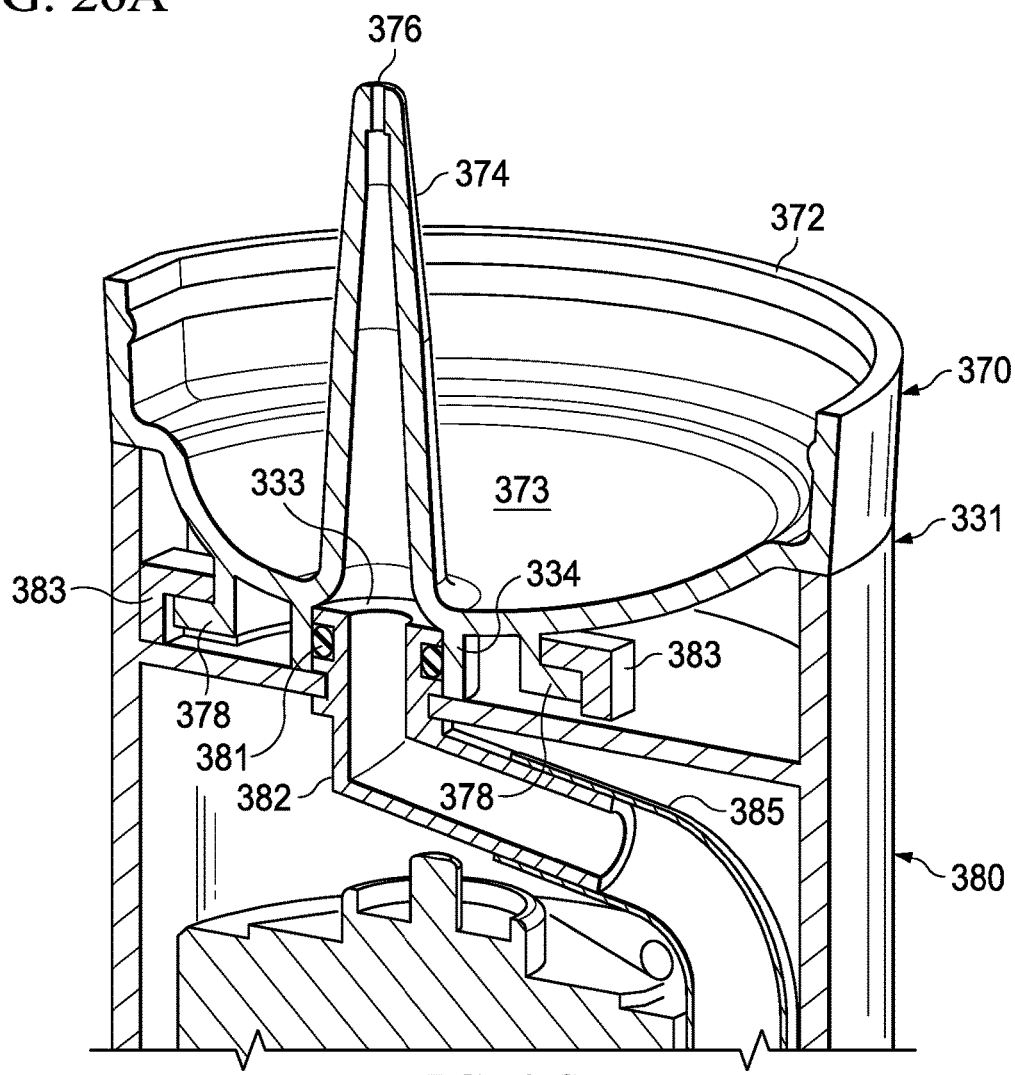

In one embodiment, as best shown in FIGS. 24 and 26A-B, the canister 370 is positively held to the pressurized air supply source 380 by a locking mechanism, which is comprised of at least one tab 378 on the canister 370 that interfaces with a mating portion 383 that captures the tab 378. The mating portion 383 protrudes from and is located within the concave opening 332 of the pressurized air supply source 380 and may comprise any shape capable of locking with a corresponding tab 378 of the main canister 370. In one embodiment, the mating portion 383 comprises one or more rounded or curved protruded edges with a thicker end piece at one end under which one or more tabs 378 may lock. One or more tabs 378 on the base of the canister 370, below the reservoir 373, then securely fits within the upper end of the pressurized air supply source 380 by way of the locking mechanism. The tab 378 or bottom of the main canister 370 fits within an opening 332 of the pressurized air supply source 380, and the canister 370 is then turned in the direction of arrow A. The tab 378 then slides under the mating portion 383 until the canister 370 locks into place. The locking mechanism in effect presses the canister 370 into a seal that seals the air channel between the canister 370 and the pressurized air supply source 380. In one embodiment, the tab 378 has a protrusion, bump or other feature that mates with a similar feature on the mating portion 383 to securely lock the two pieces together during operation and provide a tactile and auditory indication that the mating process is secure and the canister 370 and the pressurized air supply source 380 are properly connected.

Figure 31:
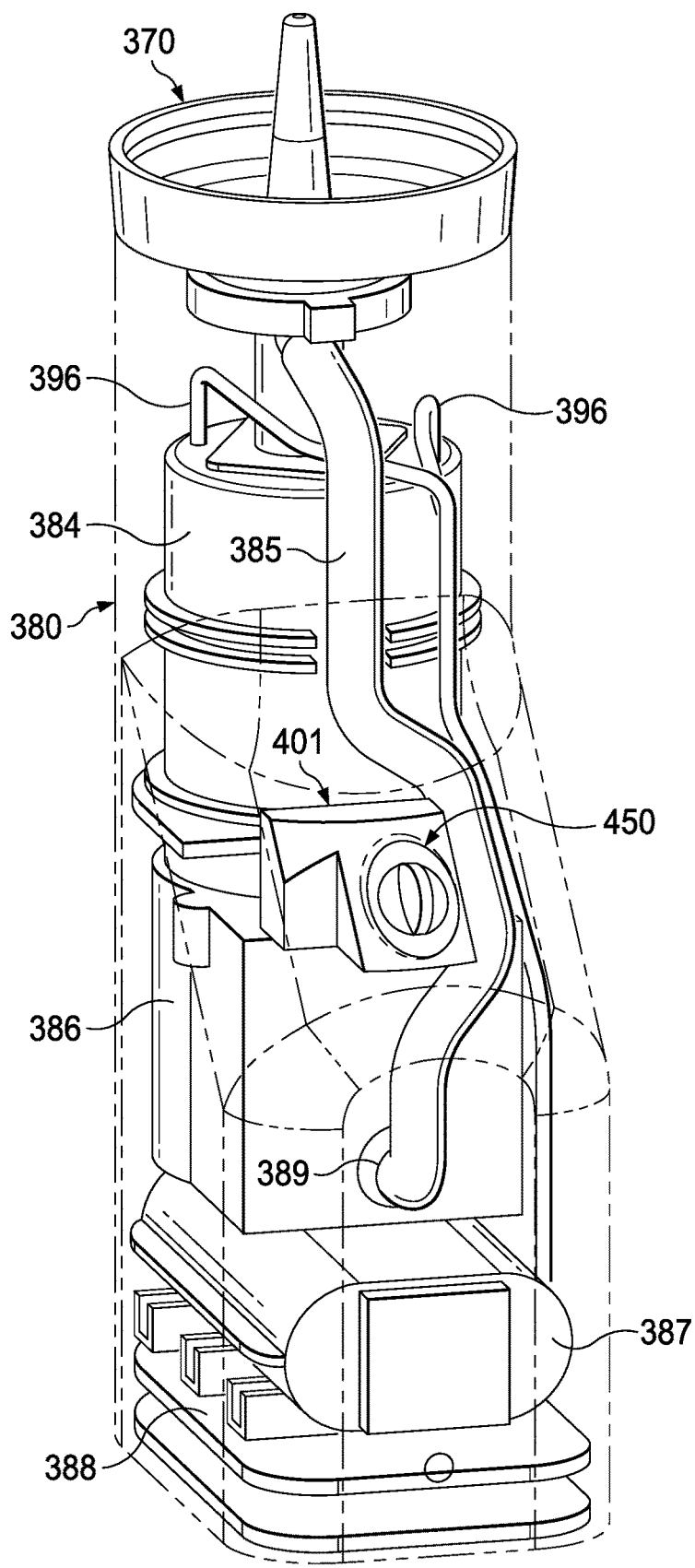
Figure 32:
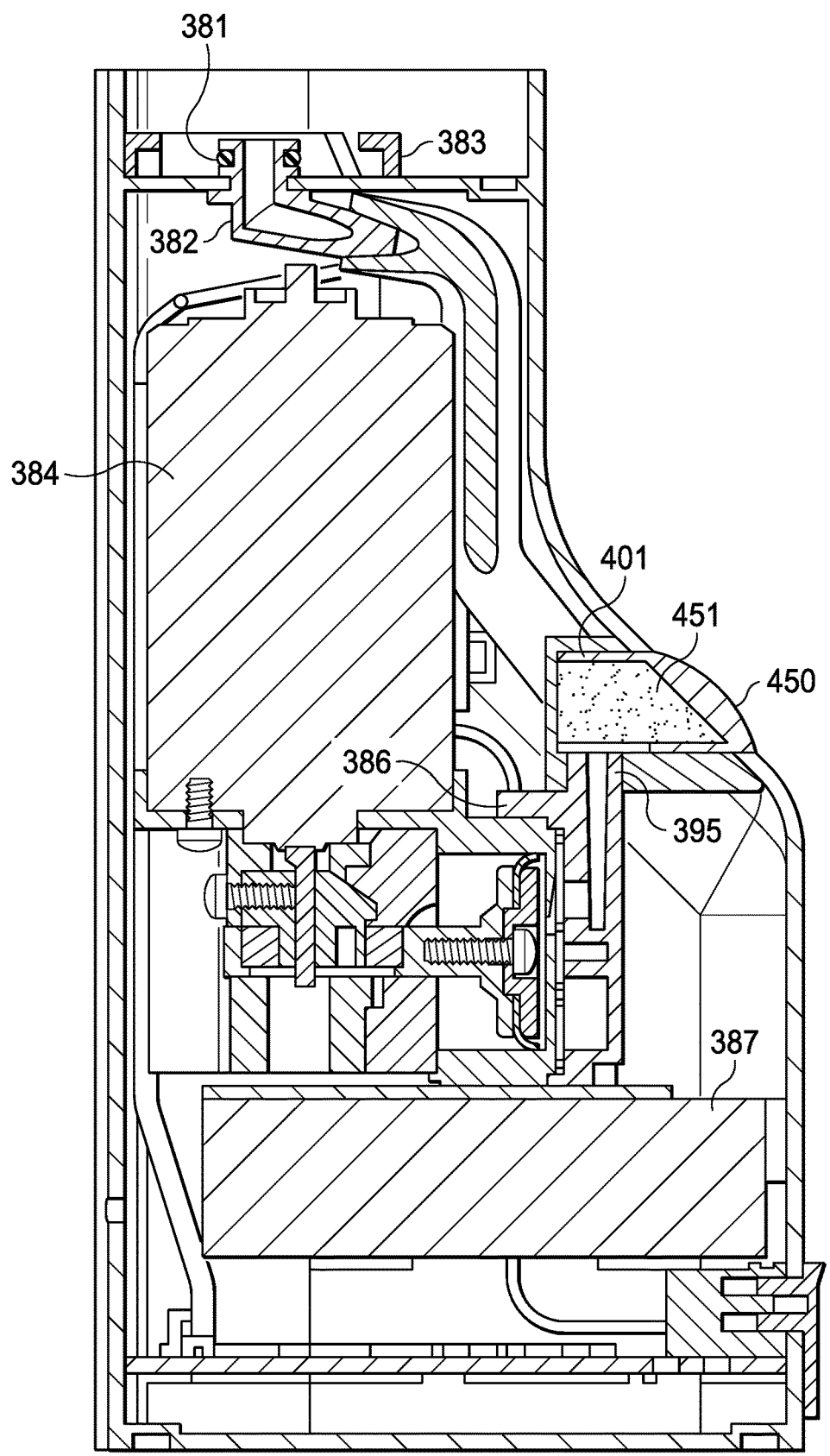

Similar to the portable irrigator described above in FIGS. 19-23, the canister 370 comprises an air inlet 334 at its bottom end below the reservoir 373, which connects to an air outlet 333 of the pressurized air supply source 380. In one embodiment, the air inlet 334 comprises an extended bottom portion to aid in sealing with the pressurized air supply source 380. In one embodiment, air outlet 333 of the pressurized air supply source 380 comprises an air outlet elbow 382 connected to the air inlet 334 of the main canister 370. An outlet tubing 385 on an opposing end of the elbow 382 connects to a pump 386 as further described below in one embodiment. More specifically, the outlet tubing 385 connects the air outlet 333 to a pump outlet 389, as shown in FIG. 31. In one embodiment, the air outlet elbow comprises an angle of between about 30 degrees to about 90 degrees in between its substantially vertical portion extending down from the air inlet 334 and its somewhat horizontal portion connected to the tubing 385, sufficient to circumvent a motor 384 within the pressurized air supply source 380, as best shown in FIG. 31. In one embodiment, an o-ring 381 helps form a seal between the canister 370 and the air outlet elbow 382 of the air outlet 333.

Referring now to FIGS. 27-28, when assembled, the irrigator comprises an insert 360 placed over the canister 370. As shown in FIG. 27, only the periphery 371 with the rim 372 of the canister 370 is visible when the insert is present for usage of the irrigator. Generally, the insert 360, also shown in FIGS. 28 and 30, is substantially similar to the inserts described in above embodiments and can thus comprise one or more of the limitations described above. The insert 360 comprises a base 391 that fits within the reservoir 373, an extension 367 above the base 391 protruding outwardly to the lip 372 of the canister 370, and a fluid channel 394 that fits over the tube 374, the elongated fluid channel 394 having a somewhat larger bottom diameter converging up to a smaller diameter at its top end 362. The discharge port 364 is concentrically aligned with the air exit port 376. In one embodiment, the base 391 of the insert 360 comprises a curved surface flush with an inner bottom surface of the reservoir 373. The fluid channel 394 tapers from one diameter around its bottom opening to a smaller diameter at its top end 362 with the discharge port 364. The fluid channel 394 is slightly larger in diameter than the tube 374 along the entire length of both the fluid channel 394 and the tube 374, with the tube 374 comprising a similar conical shape having the smaller diameter on its top end. The distance between the outer surface of the tube 374 and the inner surface of the fluid channel 394 should be sufficient to create a venturi effect. When used, the discharge port 364 is the uppermost part of the irrigator 330, with no additional barrier or structure breaking up the size or flow of the fluid drawn up from the canister 370. In one embodiment, the distance between the outer surface of the tube 374 and the inner surface of the fluid channel 394 is about 0.0001 to about 0.010 inches (about 0.00254-0.254 mm)). One or more bumps 369 may be used, by way of example, to secure a tight fit and/or proper alignment between the insert 360 and the main canister 370.

An indicator 368 (best depicted in FIG. 27) may be used on one side of the extension 367 to assist with alignment of the flat portion 377 on the main canister 370. The extension 367 comprises a rim 361 positioned on top of the main canister 370 and below the discharge port 364, through which mist will pass for irrigation of a nasal passage. In one embodiment, the rim 361 engages the lip 372 of the canister 370. In one embodiment, the extension 367 is slightly concave.

Similar to the inserts described above with extensions, the extension 367 comprises at least one groove 365 extending vertically along an exterior of the fluid channel 394 to an aperture 366 at the bottom of the fluid channel 394 or within the extension 367 adjacent to the fluid channel. The groove 365 runs vertically from a point below the discharge port 364 of the fluid channel 362 down to the aperture 366. During use, deflected fluid will begin to flow back down the vertical groove 365. The aperture 366 forms a channel of communication back into the reservoir 373, which is an inner chamber formed by the mating of the canister 370 and the extension 367 of the insert 360. As fluid exits the inner chamber, a vacuum is created which is relieved by the inflow of air and the deflected fluid into the reservoir 373 through the aperture 366, thereby ensuring maximum usage and minimized waste of the fluid. In one embodiment, the aperture 366 in the extension 367 is located at a bottommost level of concavity of the extension 367.

Similar to the embodiment above related to FIG. 12b, the insert 360 has a bottom face with at least one groove (as depicted as FIG. 25B) forming a communication channel between the canister 370 and the insert 360. In one embodiment, as depicted in FIG. 12b, the bottom face of the insert 360 may also comprise a peripheral groove surrounding the bottom opening of the fluid channel to which the groove may extend from the outside edge of the bottom face. In one embodiment, the groove extends from the outside of the base to the inside of the insert. The base should comprise at least one groove but may also comprise more than one. The number of grooves as well as the width and depth of the groove will help regulate the flow of fluid up to the point that the airflow takes over the upper limit of flow. In one embodiment, the grooves may range in width from about 0.005" to about 0.150" (0.127 mm to about 3.81 mm). In one embodiment, the grooves may range in depth from about 0.001" to about 0.050" (0.0254 to about 1.27 mm). In one embodiment, the base 391 of the insert comprises a curved surface flush with an inner bottom surface of the reservoir of the main canister 370.

A cap 350 is optional but must be removed during use. When present, as shown in the assembled perspective view of FIG. 27, the cap helps seal fluid within the irrigator to provide for storage or travel with the irrigator. The cap comprises no holes and covers the entire fluid channel 394 of the insert 360, comprising a sealing plug (best shown in FIG. 30) for the discharge port 364. As with above embodiments, the cap 350 fits over the fluid channel 394 and comprises a sealing plug, in one embodiment, which projects into and fits within both the discharge port 364 and the air exit port 376 of the canister 370 to seal the reservoir 373 from the air exit port 376 and fluid channel discharge port 364 when the cap 350 is placed over the insert, as shown in the assembled view of FIG. 27. Similar to above embodiments, the sealing plug of the cap may also seal or fit within only the discharge port 364 in other embodiments. The cap 350 may comprise an elongated conical shape in one embodiment to ensure a good fit over the insert and its apertures. Optionally, the cap 350 may comprise a flattened edge to help with alignment over the insert 360. The bottom portion 351 of the cap mates with a portion of the top face of the extension 367 and thus its shape will depend on the curvature of the top face of the insert's extension. The cap 350 may optionally comprise one or more vertically extending indentations 352 or curved ends 353, as best shown in FIG. 29, to mate with the grooves 365 and/or apertures 366, respectively, of the insert.

Beginning with FIG. 30, one embodiment of an airflow regulating system within the contiguously attached pressurized air supply source 380 is depicted. Preferably, the internal components of the pressurized air supply source 380 are placed to enhance stability and feel of the irrigation device with a low center of gravity and torque generated by the motor being in the vertical axis. Such an arrangement helps engage the large muscles of the forearm for improved stability.

In one embodiment, the airflow regulating system comprises: a pump 386 in communication with a motor 384 and the air inlet 334 (shown in FIG. 26B); and a filter 451 (shown in FIG. 33B) for filtering incoming air, the filter 451 comprising an inlet air manifold 401 connected to the pump 386 and sealing against a pump air inlet post 395 of the pump 386, as further described below. The pressurized air supply source 380 further comprises a circuit board 388. In one embodiment, the circuit board uses a pulse-width modulation to ensure consistent motor speed. In one embodiment, the circuit board uses a programmable digital control to ensure consistent motor speed. In one embodiment, the circuit board also charges the battery from an external AC/DC converter and ensures that the motor behaves consistently whether powered by an AC/DC converter or by the battery. In one embodiment, the circuit board communicates the status of the battery to the user via an LED on the outside of the unit. In one embodiment, the motor 384 is a brushed motor. In one embodiment, the motor 384 employs caged brushes. In another embodiment, the motor 384 is a brushless motor. The outlet tubing 385, described above, circumvents the motor 384 in one embodiment, to connect the canister 370 to a pump outlet 389 of the pump 386. A battery 387 within the pressurized air supply source drives the motor 384 in one embodiment. In one embodiment, the battery 387 is a rechargeable lithium ion battery. In some embodiments, the battery 387 may be accessible or removable by a user. In one embodiment, the battery is not accessible to a user. In another embodiment, the motor 384 is driven by an external power supply. In one embodiment, a motor controller board utilizes pulse width modulation to control the motor speed so as to maintain a very narrow band of motor speed to regulate the airflow generated by the pump. More specifically, the motor will operate within a wide range of +/−15% and within an operating range of +/−4% of its set point. In one embodiment motor wires 396 are twisted to mitigate electrical noise to meet IEC-60601-1 third edition requirements for electrical emissions. In one embodiment, the motor wires 396 may also include an electronic filter that may incorporate ferrites to suppress noise. In yet another embodiment, motor wires 396 are comprised of a coaxial cable to mitigate electrical noise to suppress noise. In one embodiment, the motor 384 and the pump 386 contact the pressurized air supply source 380 through vibration dampers.

Figure 33A:
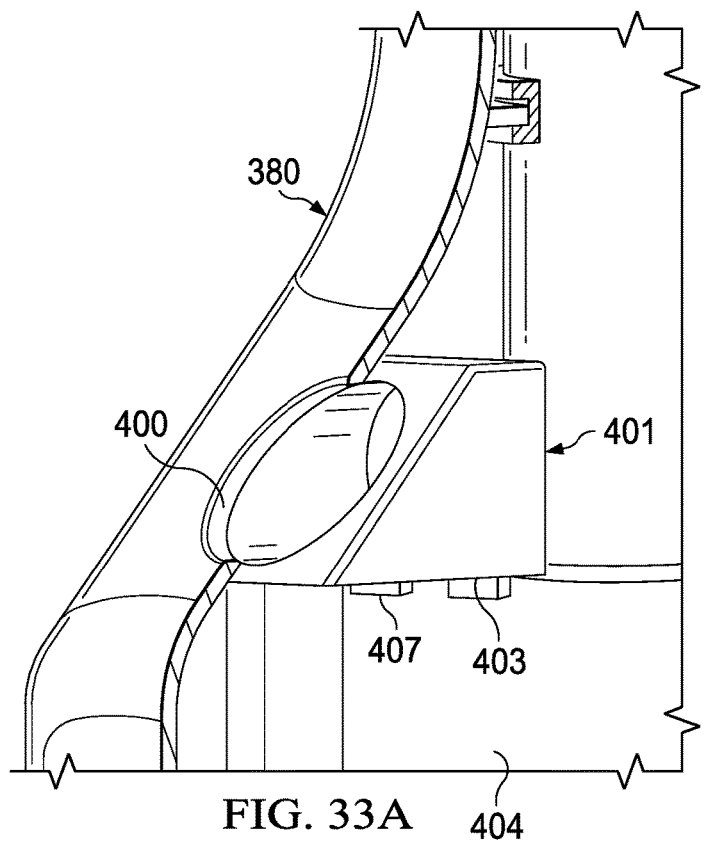
Figure 33B:
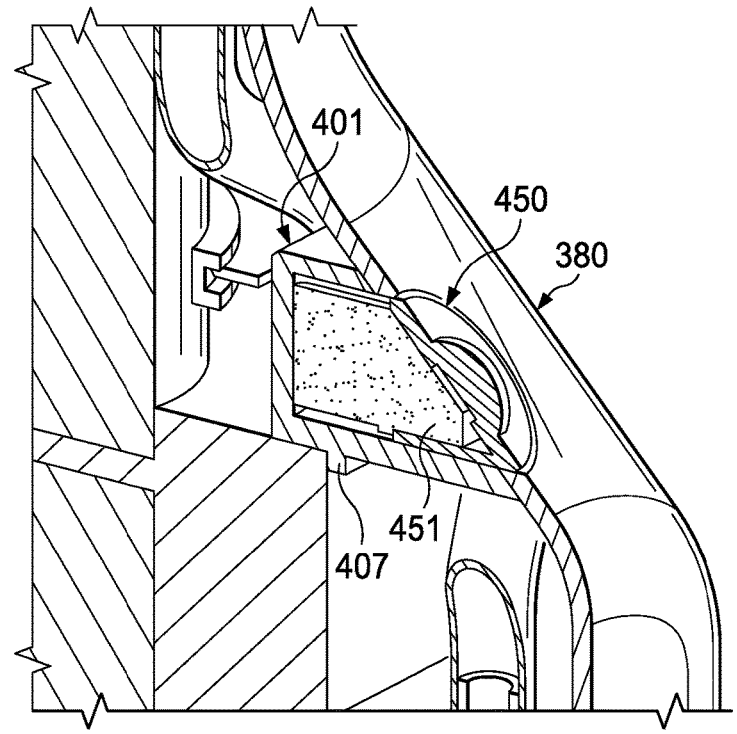

FIGS. 33A and 33B depict partial views of opposing sides of the pressurized air supply source 380, with either half of the pressurized air supply source removed to better reflect some of its adjacent interior components; in particular to depict the air inlet manifold or 401 and filter 451 under the filter cover 450, which resides within the opening 400 of the pressurized air supply source 380. The air inlet manifold 401 is a small box that forms a small fitting that seals around the air inlet of the pump, eliminating the need for a tube-like communication from the outlet to the pump 386. An opening 400 is located along the angled surface of the pressurized air supply source 380 in one embodiment. When assembled, the filter cover 450 is visible on an external side of the pressurized air supply source, within the opening 400. In one embodiment, the filter cover 450 may be removable for access to the filter 451.

Figure 34A:
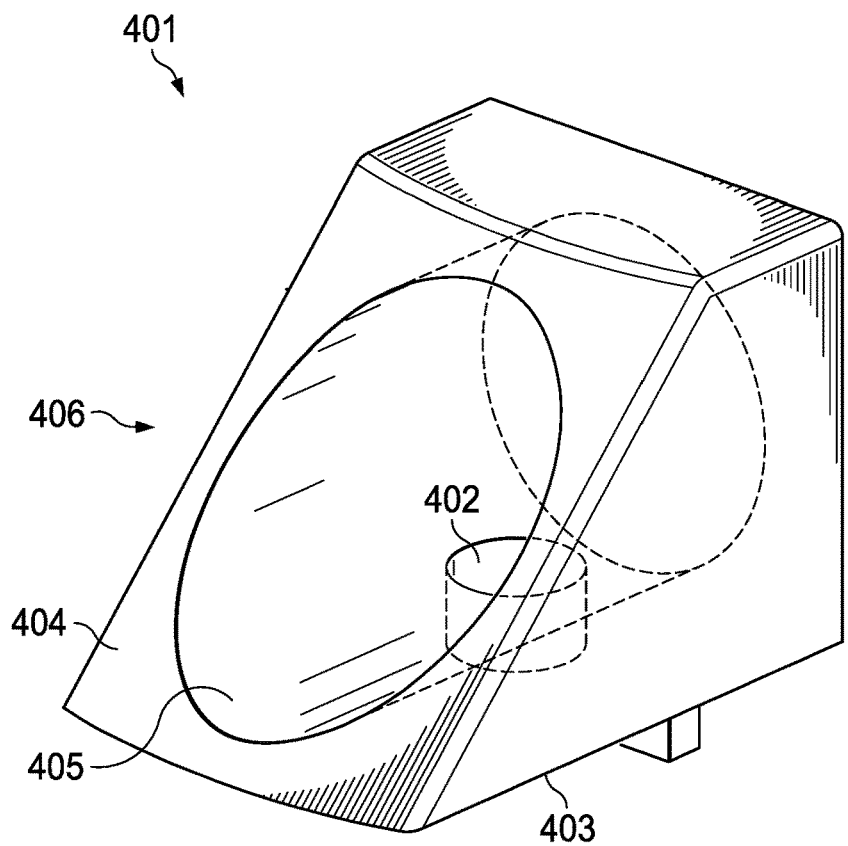
Figure 34B:
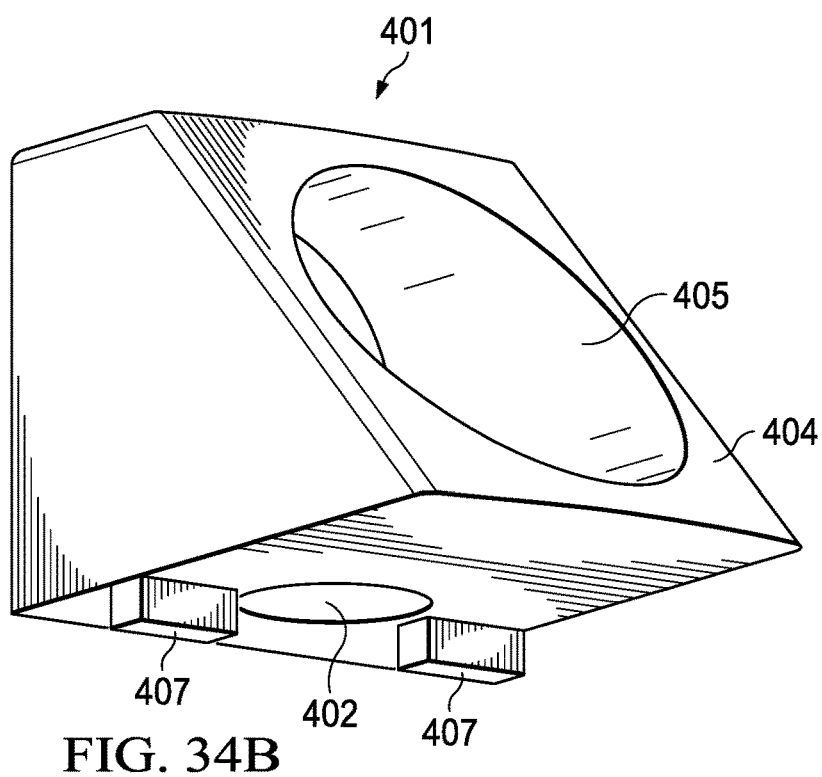

In one embodiment, the filter cover 450 is shaped to exactly match the opening 400 in the pressurized air supply source 380. As best shown in FIG. 34A, air inlet manifold 401 comprises a cutout 405, which also matches the opening 400, wherein the filter 451 is placed. The angled surface 404 of the air inlet manifold 401 matches and seals against the inside of the pressurized air supply source 380. A cutout 402 forms an air channel within the air inlet manifold 401 to the air inlet of the pump. The cutout 402, perhaps best shown in FIG. 34B is at the bottom of the air inlet manifold 401 aligning with a centerline of the pump 386. Thus, the air pathway is centered within the air inlet manifold 401. A flat bottom 403 of the air inlet manifold 401 rests on the pump 386. The air inlet manifold 401 thus connects and seals against a pump air inlet post 395 of the pump 386 in one embodiment. In one embodiment, the air inlet manifold 401 comprises an anti-rotation tab 407 along its bottom side to prevent movement. In one embodiment, the air inlet manifold 401 may comprise more than one anti-rotation tab 407 adjacent to the cutout 402.

Figure 35:
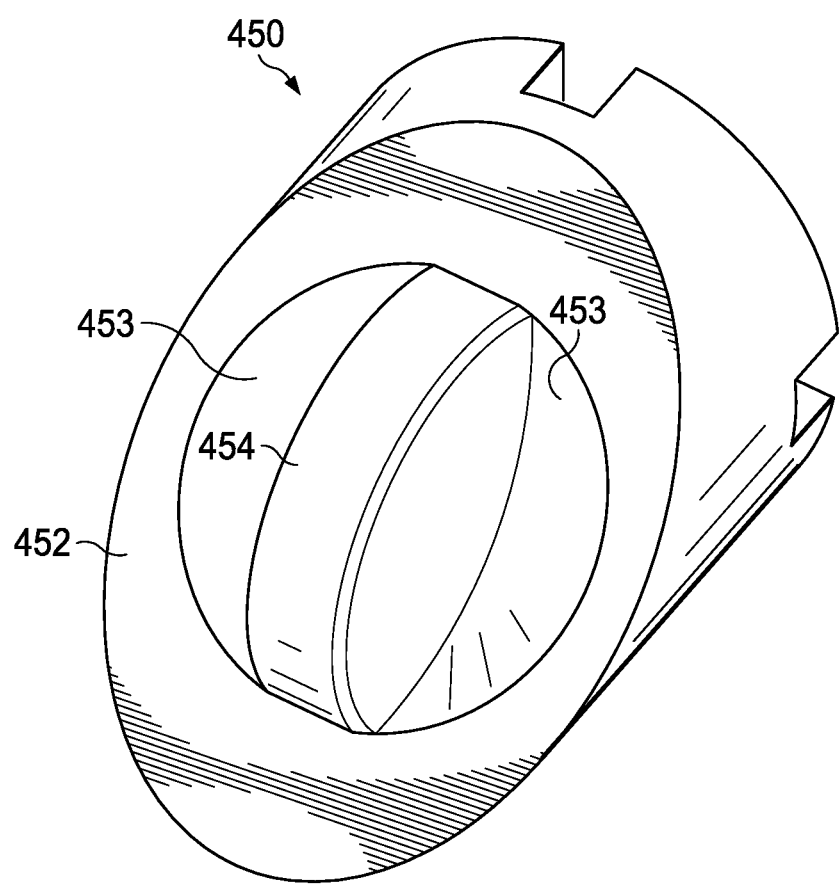

The filter cap or cover 450 is shown in more detail in FIG. 35. The filter 451 within the air inlet manifold 401 may be composed of 80 ppi reticulated polyurethane foam in one embodiment. In one embodiment, the filter 451 is pressed and shaped within the filter cover 450. In one embodiment, the filter 451 is accessible to a user for replacement or cleaning. Access to remove or replace the filter 451 may be accomplished by any means known in the art. A centerpiece 454 may comprise a raised, arch ridge, in one embodiment, for removal of the filter cover 450 from the manifold 401. Face 452 is flush with the pressurized air supply source 380. Vent 453 opens to filter 451 to allow air to pass and centerpiece 454 secures the filter inside the filter cover 450 and provides for a place for a user's fingers to insert the filter cover 450 into the manifold 401.

As described for previous embodiments, the portable nasal irrigator 330 creates a variable particle size up to 100 microns under a pressure of 1-15 psi (0.069-1.0345 bar), creating a pressurized airflow that enables the resultant air-mist stream to stent-open the soft tissues of the upper airway and reach the whole nasal cavity independent of the patient's breathing. A vast majority of the particles are sized at about 20 microns. In one embodiment, the mist expelled through the exit hole comprises air and fluid particles or droplets, 100% of particles or droplets being greater than 5 microns in diameter and 99.8% of the particles or droplets are greater than 10 microns in diameter. In one embodiment, the particle or droplet diameter distribution has a mode centered around 23 microns, the mist is expelled under a pressure of 1-15 psi with a fluid delivery rate of 1-20 ml per minute, and airflow of 3-8 liters per minute, creating an air column that drives the resultant mist past the nasal valve and antrum of the nose to coat the turbinates, middle meatus to reach the posterior and superior regions of the nasal cavity and the paranasal sinus cavities without introducing the aerosol into the lungs. In one embodiment, the air pressure ranges from about 3-12 psi (0.207-0.823 bar), with about 1-12 lpm of airflow, and a fluid delivery rate of about 1-20 ml per minute. In one embodiment, the air pressure ranges from about 4-8 psi (0.276-0.552 bar), with about 3.5-8 lpm airflow, and about 15 ml per minute fluid delivery. The resultant aerosol mist reaches the area of the nasal cavity above the inferior and posterior to the nasal turbinate or chonchae to ensure that the mist reaches the areas of the sinus ostia to clear this area of the nasal cavity and enable the natural mucociliary flow to clear the sinuses.

By way of example, a portable nasal irrigator device as described herein may be comprised of ABS, Polycarbonate, glass, stainless steel, styrolene, styrene-butadiene copolymer, co-polyester BPA-free plastics or any other plastics appropriate for medical device use, and any combination thereof. The device may further be comprised of an antimicrobial compound in some embodiments. In one embodiment, the canister and insert are constructed of a BPA-free material. In one embodiment, the canister is USP class VI compliant for the storage and delivery of drugs. In another embodiment, no latex is used in the construction of the device.

In one embodiment, the portable nasal irrigator is "smart" which can also be achieved through the use of an analog-digital hybrid programmable controller/circuit board, allowing for programmable operation of the device to fit the needs of the patient depending on the therapy being delivered. Examples of this programmability include absolute run time for a single actuation, charge status of the battery when employed, absolute number of runs within a given period of time, and various overrides for these programmable features. For instance, to reduce abuse and diversion of controlled and addictive substances, the device could be programmed to allow no more than 5 actuations in a 5 minute period, with a time limit of 3 minutes total for all actuations, and then no actuations until the next appropriate dosing period. One skilled in the art, armed with this disclosure, can envision any number of permutations to this pattern. For instance, a pattern of use that might enhance absorption of a drug could include 5-subdoses over an hour, wherein the external indicators for the device help the user keep track of the timing of doses and even limit the window of doses appropriate to the drug. This programmability may be performed at the factory or by a technician or the caregiver. There is also a need for the device to include memory to store patterns-of-use information, and there is a need for this information to be communicated to a computer, smart phone or other device via a USB port, blue tooth connection, WIFI, cellular or other methods. There is also a need for the device to include a unique identifier, such as the global unique device identification number associated with the US FDA global unique device identification database. This identifier could be stored in the device memory or on an embedded RFID chip or other such chip.

Figure 36:
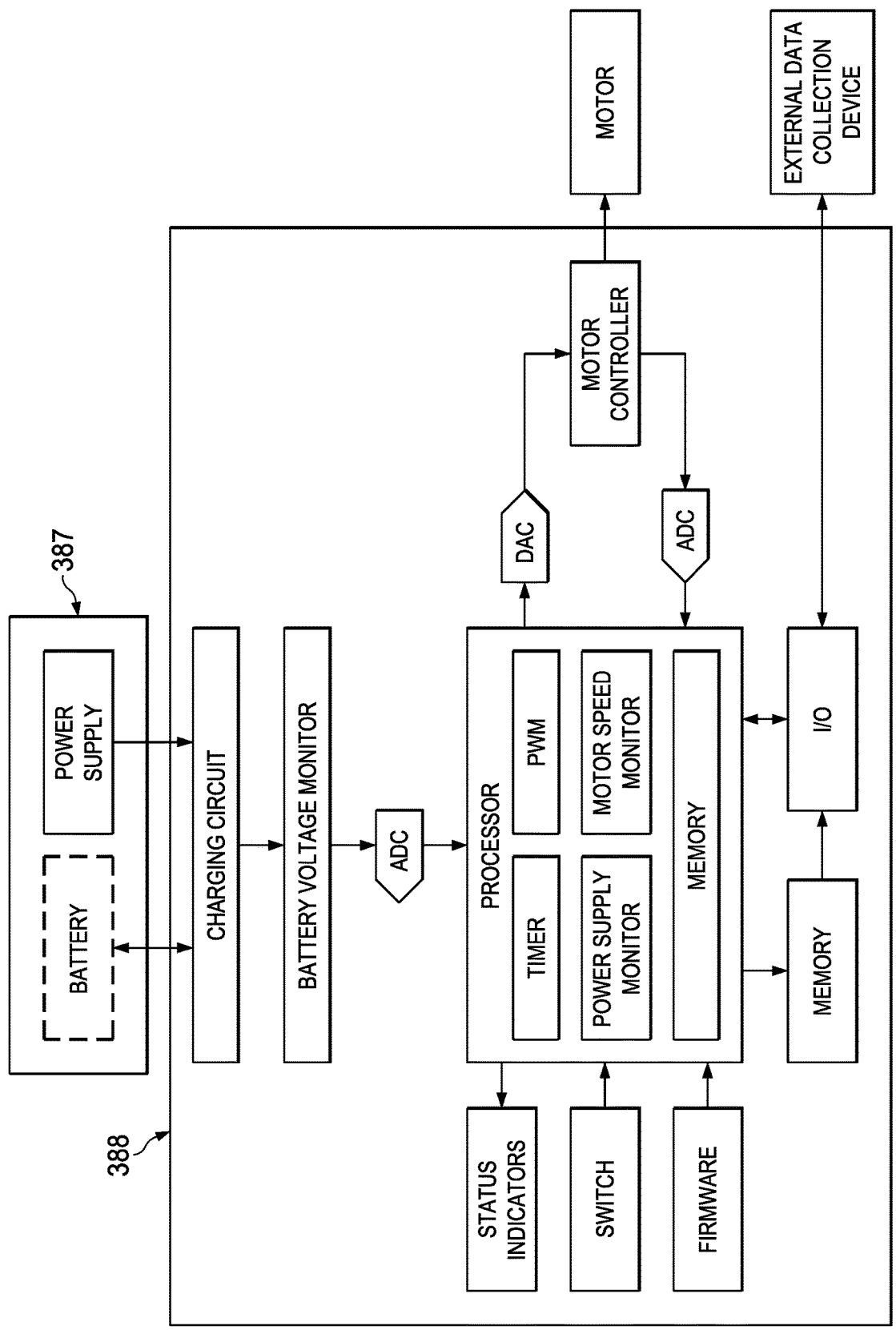

FIG. 36 depicts a block diagram of one embodiment of the programmable circuit board. The programmable circuit board is a component of the airflow regulating system of a portable nasal irrigator device. As mentioned with previous embodiments, the programmable circuit board precisely controls the motor speed to ensure the proper airflow, ensures the battery voltage is maintained for operation, and drives status indicators to inform the user when the battery requires charging and is being charged. In FIG. 36, the circuit board may comprise a charging circuit connected to a either a power supply or a battery and a battery voltage monitor. The circuit board may also have any number of analog-to-digital converters and digital-to-analog converters for controlling either the power supply or the motor of the portable nasal irrigator. The circuit board may use a pulse-width modulation module or a programmable digital control to ensure consistent motor speed, and may be programmed to control the motor speed regardless of battery power, such that the motor operation is discontinued when the battery voltage is no longer capable of maintaining the motor speed, without sputtering or altering the speed as the battery voltage drops. The circuit board may be connected to the status indicators to indicate whether the battery needs charging or is charging, switches, and may include a status indicator, either programmed as an alert to an external device or as a status indicator light, to notify the user that the battery requires charging such that there is at least one actuation of the portable nasal irrigator to deliver a full dose of the irrigator fluid. The circuit board may also be connected to various input/output connectors for connecting to other components of the portable nasal irrigator or to external data collection devices. The circuit board may also comprise a processor and memory devices (or any other tangible non-transitory computer useable medium) for automating the airflow regulating system.

The circuit board may be connected to a computer, smartphone, tablet, or any other computing device. By connecting the circuit board to a computing device, the portable nasal irrigator may be programmed to perform certain tasks, like those further disclosed below. A computing device may be any electrical device capable of accepting stored program instructions from a computer readable medium and processing those program instructions to perform a defined task. Such devices include, but are not limited to, a mainframe, workstation, desktop, laptop, notebook, or tablet computer, a database server, web server, or the like. One of ordinary skill in the art will appreciate that the construction, choice of programming language, programming, operation, and functionality of such computer processing devices is well known, rendering further description of such devices unnecessary in this regard.

The portable nasal irrigator may be extemporaneously programmed in an ad-hoc fashion based on information provided with each prescription information provided with a drug and/or medical fluid. The prescription information may be contained in a smart chip, dot matrix, bar code or other encoded information that may be read from the drug and/or fluid package, and the portable nasal irrigator may have a smart chip reader, bar code reader, or other computing device capable of detecting and processing the encoded information. The encoded information processed by the reader may then be used by the portable nasal irrigator to perform in different ways.

A series of pre-determined scenarios may also be programmed into the portable nasal irrigator and accessed via a lookup table that includes all the run time, lockout periods, and other parameters. The scenarios may be associated with the national drug code, a bar code, or any other such instruction that may be included with the drug to select or determine the appropriate pre-programmed scenario. The portable nasal irrigator, in this embodiment, may incorporate a reader to read the encoded prescription information. An example of the lookup table of this exemplary embodiment is provided below:

| Scenario | Max run time per activation | Max run time per interval | Max runs per interval | Dispensing Period | Max intervals | Lockout |
| --- | --- | --- | --- | --- | --- | --- |
| 1 | 3 minutes | null | null | null | null | null |
| 2 | 20 seconds | 3 minutes | 10 | 30 minutes | null | null |
| 3 | 20 seconds | 3 minutes | 10 | 30 minutes | null | 360 minutes |
| 4 | 3 minutes | 3 minutes | 10 | 30 minutes | null | null |
| 5 | 3 minutes | 3 minutes | 10 | 30 minutes | null | 360 minutes |
| 6 | 3 minutes | 3 minutes | 10 | 30 minutes | 2 | 360 minutes |

To further secure the usage of the portable nasal irrigator, the portable irrigator may incorporate technology to identify authorized users via a personal ID, e.g., fingerprint, eye scan, mobile application, ID card embedded with an RFID, or other identification technology. For example, a mobile application may require a user to verify his or her identity before unlocking the portable nasal irrigator for use. An administrator (physician or healthcare personnel) may use the mobile application to temporarily alter the information from the pre-determined scenario lookup table for the special needs of the user of the portable nasal irrigator. User identification may be cross-checked against the drug prescription to ensure the portable nasal irrigator is used by the proper person, increasing safety for patients, in particular where multiple patients may use the same base unit with their own cup and insert.

In one embodiment, the airflow regulating system controls the performance of the portable nasal irrigator by automating the motor and regulating the power supply. The airflow regulating system automates the motor to perform at certain motor speeds and at certain time intervals. The airflow regulating system may use lockout periods to prevent abuse and diversion of controlled substances, such as Ketamine, its analogs and metabolites that may be particularly subject to abuse. A lockout period is a time period that the portable nasal irrigator will not actuate even though a user or an administrator may request actuation. When the airflow regulating system determines that a certain number of actuations have been performed in a predetermined dispensing period, the airflow regulating system will lock and prevent any more actuations of the system until the lockout period is passed. An administrator of the portable nasal irrigator may program or set up the airflow regulating system for a certain number of actuations of the system in a certain dispensing period before a programmed lockout period by directly connecting to the airflow regulating system or by other input/output connections, such as Wi-Fi, Bluetooth, Ethernet, etc.

In another embodiment, the airflow regulating system may control the maximum run time of the portable nasal irrigator by use of a timer. The maximum run time prevents the portable nasal irrigator from being left on or left running inadvertently. A timer on the programmable circuit board may alert and trigger other components on the programmable circuit board. The timer may be programmed or set up in any way a person of ordinary skill in the art would program or set up a timer. The airflow regulating system with the timer monitors the time the portable nasal irrigator delivers irrigation fluid, and calculates this monitored time toward the maximum run time. This limitation of run time of the portable nasal irrigator may be used in conjunction with a lockout period. A user or an administrator may set up the portable nasal irrigator to lock and prevent delivering any more of the irrigation fluid once the airflow regulating system determines that the maximum run time has been reached, and will only allow the delivery of more irrigation fluid once a lockout period has passed. Alternatively, the user or administrator may set up the portable nasal irrigator to deliver fractions of a dosage of irrigation fluid over a longer period of time than a full dosage requires, and the airflow regulating system may compensate for this set up.

Run time, as used herein, may differ from a dispensing period in some embodiments. When used together, the run time of the portable nasal irrigator is the time measured from the first actuation of the portable nasal irrigator, while the dispensing period is the time interval that the user or administrator is allowed to use or actuate the portable nasal irrigator. Both the run time and the dispensing period, either individually or together, may be predetermined or preset by the manufacturer, or programmed by a user and/or administrator of the portable nasal irrigator.

For example, in a default scenario, the user and/or administrator of the portable nasal irrigator may set up the airflow regulating system to run continuously for three minutes once an on/off button or switch is pushed or until the on/off button/switch is pushed again. The user and/or administrator may also set up the airflow regulating system with split dosage, so that the portable nasal irrigator runs for twenty seconds or until the on/off button is pushed for a total accumulated time of three minutes with a thirty minute time span. The rationale for this split dosage set up with an overall time span monitor is to ensure that the user receives the full dosage within a time frame, and to prevent abuse of the portable nasal irrigator.

To further prevent abuse of the portable nasal irrigator, a lockout period may be implemented in one embodiment. The user pushes the on/off button of the portable nasal irrigator, and the airflow regulating system runs for twenty seconds or until the on/off button is pushed. The airflow regulating system may monitor its run time toward the total accumulated time during an overall run time for delivery of irrigator fluid. Once a total accumulated run time of three minutes is reached within a thirty minute dispensing period, the airflow regulating system does not deliver any more irrigator fluid until a lockout time period passes (6 hours, 12 hours, or 24 hours). Once the lockout time period passes, the airflow regulating system may then allow for the delivery of irrigator fluid.

The airflow regulating system may limit the number of actuations so as to provide an escape for a user who has to stop the use of the portable nasal irrigator during the dispensing period. The airflow regulating system monitors the number of dosages (or sub-dosages) delivered by the portable nasal irrigator, and calculates this monitored number towards the limited number of actuations. Sub-doses, also called sub-dosages, help improve absorption of the irrigator fluid and are portions of a full dosage, divided up.

This limitation of actuations may be used in conjunction with a lockout period. A user or an administrator may set up the portable nasal irrigator to lock and prevent delivering any more of the irrigation fluid once the airflow regulating system determines that the maximum number of actuations has been reached. Alternatively, the user or an administrator may set up the portable nasal irrigator to deliver fractions of a dosage of irrigation fluid over a longer period of time than a full dosage requires, and the airflow regulating system may compensate for this set up. The administrator of the portable nasal irrigator may program or set up the airflow regulating system for limiting the number of actuations by directly connecting to the airflow regulating system or by other input/output connections, such as Wi-Fi, Bluetooth, Ethernet, etc.

In an exemplary embodiment, the airflow regulating system may permit delivery for as long as the user requires actuation or delivery of the irrigator fluid. This embodiment of the airflow regulating system limits the number of actuations or deliveries of irrigator fluid. So, once a user presses the on/off button, irrigator fluid is dispensed via the portable nasal irrigator and will continue until the on/off button is pressed again. The user can continue to actuate the portable nasal irrigator until the limit of the number of actuations is reached. Once the actuation limit has been reached, the airflow regulating system may prevent any more actuations for a lockout period (6, 12, or 24 hours).

In one embodiment of the portable nasal irrigator, the airflow regulating system may monitor and store patterns of use of the portable nasal irrigator. These patterns of use may be used by the user or the administrator of the portable nasal irrigator, or by a healthcare professional, in determining whether the usage of the portable nasal irrigator is effective. The patterns of use may be transmitted from the programmable circuit board through its input/output ports to an external data collection device, which may comprise any computing device. The transmission may be across any communication channel, such as Wi-fi, BlueTooth, cellular, telephonic, cable, etc. The user or administrator, or healthcare professional, in turn, may program the airflow regulating system to perform the above mentioned tasks, and the programmed instructions may be stored in memory or any other tangible non-transitory computer useable medium.

FIGS. 37-42 illustrate one embodiment of an improved nasal drug delivery device. Generally, the improved nasal drug delivery device comprises a canister or main canister as described in any of the above embodiments, the canister comprising a puncturing element within its reservoir, an insert as described in any of the above embodiments, a pressurized air supply source as described in any of the above embodiments.

Figure 37:
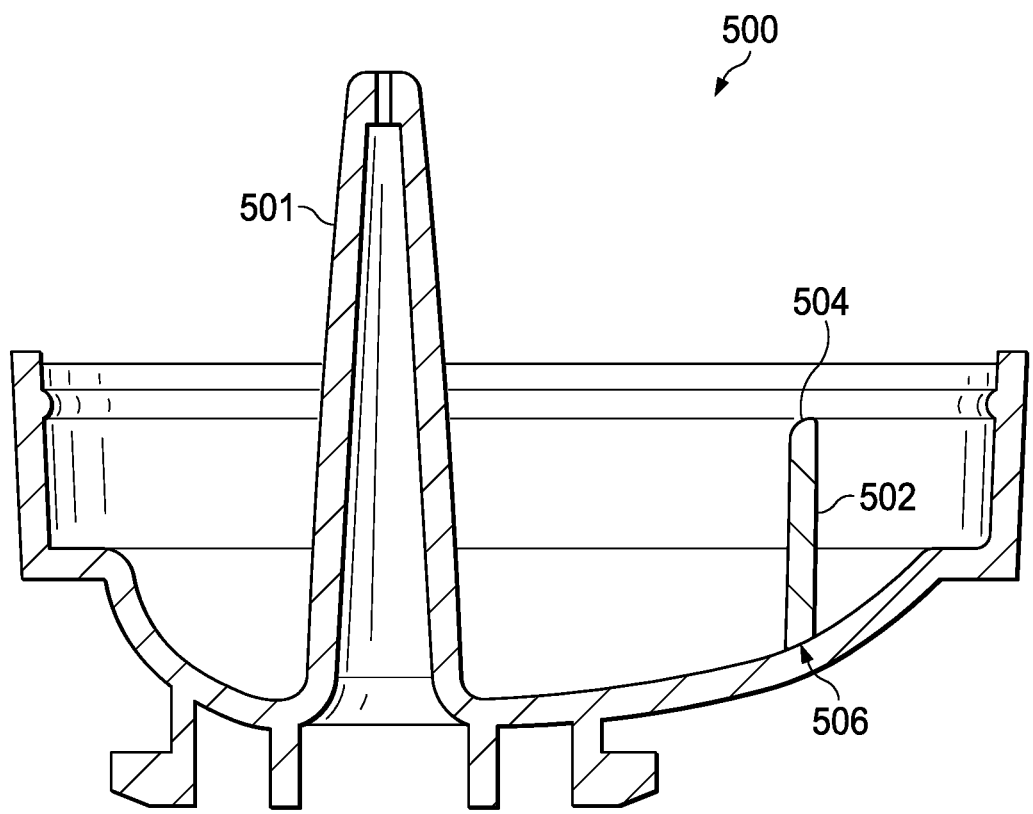
Figure 38:
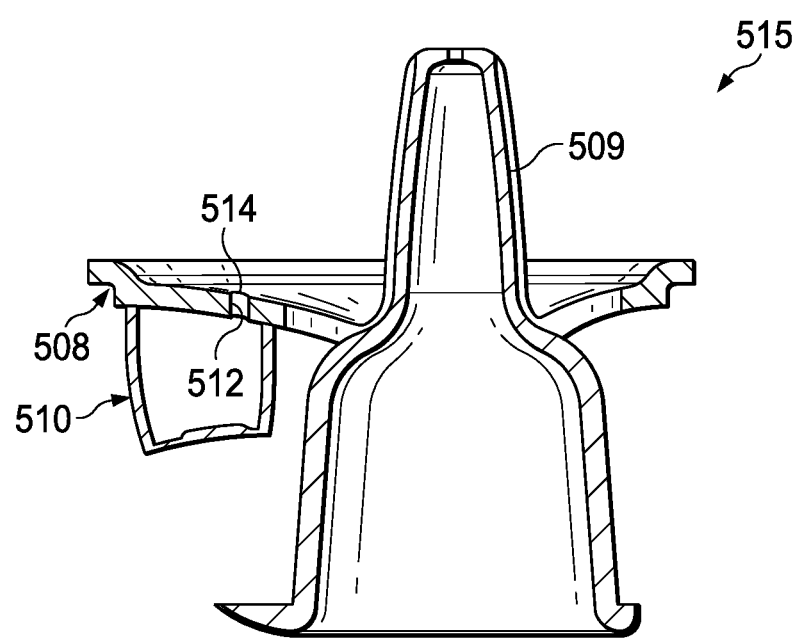
Figure 39:
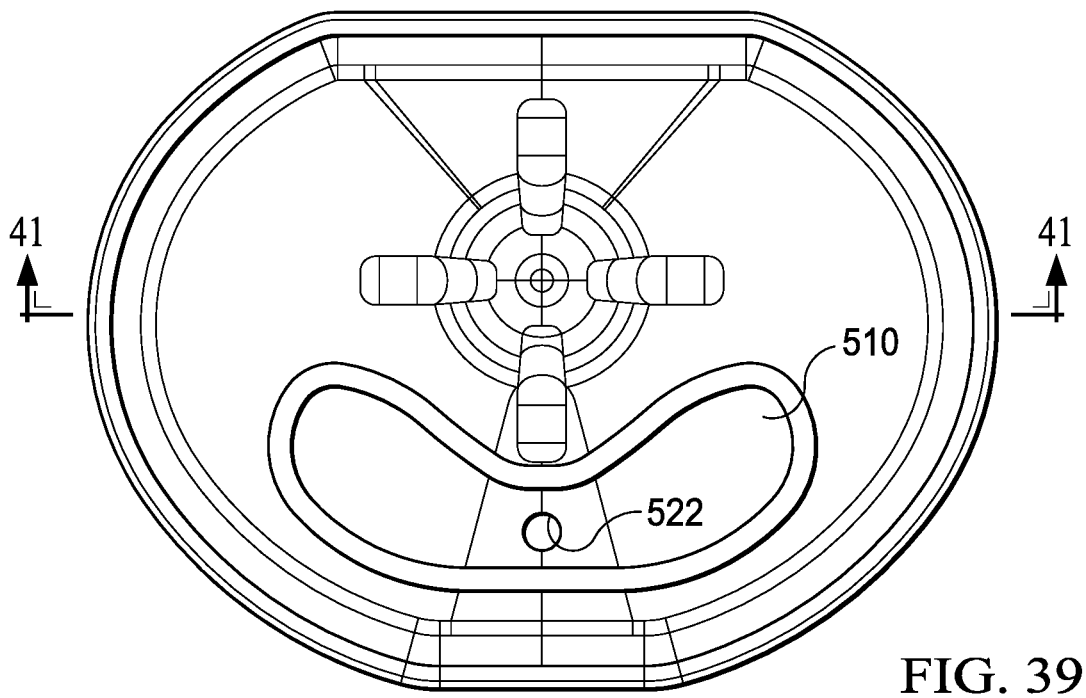
Figure 40:
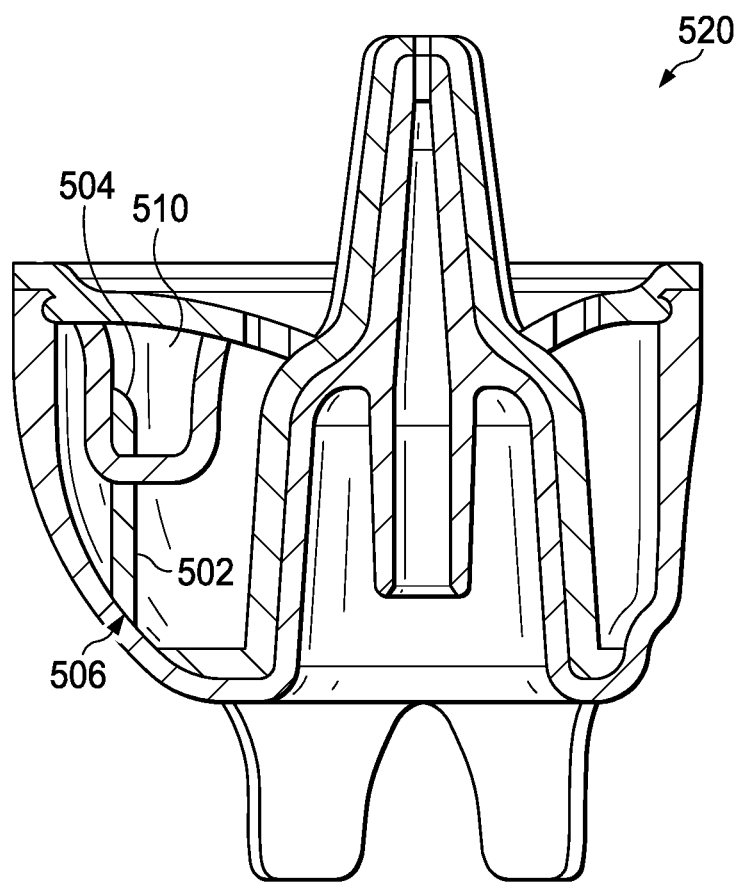

FIG. 37 is a cross section view of a portion of a canister according to one embodiment. The nasal drug delivery device comprises a canister 500 comprising a reservoir, an air exit port 501 extending beyond a rim of the canister 500 and a puncturing element 502 on an inner surface 506 of the canister. In one embodiment, further described below, the nasal drug delivery device comprises an extension between the fluid channel and the canister, and a storage compartment comprising a filling, the storage compartment attached to the extension, wherein at least a portion of the storage compartment is formed of a material that can be penetrated by the puncturing element to release the filling into the canister and form a medicated liquid prior to dispensing of a medicated mist through an exit hole of the fluid channel directly to a user. In another embodiment, the storage compartment is a separate and individual piece, unattached from, but for use in combination with, the improved device.

In some embodiments, the canister may comprise any of the above described canisters or main canisters; for example, as described with regard to FIGS. 1-17, 19A-27, and/or 29-31. In some embodiments, the insert may comprise any of the above insert embodiments; for example, as described with regard to FIGS. 1-17, and/or 19A-31. In one embodiment, the extension may comprise any of the above embodiments beginning at FIG. 12; for example, as shown in FIGS. 12-14, and 19A-30.

Turning to FIG. 37, the puncturing element 502 comprises a tip 504 that is capable of piercing at least a portion of a storage compartment, as described below. In one embodiment, the tip is curved. In one embodiment, the tip is C-shaped. In one embodiment, the tip is J-shaped. In one embodiment, the puncturing element 502 is substantially vertical. However, angled puncturing elements 502 are also within the purview of one skilled in the art, having read this disclosure. In one embodiment, one end of the puncturing element 502 is bonded, attached, or molded to an inner surface 506 of the canister. To accommodate for the insert of the device, the puncturing element 502 should be attached on an inner surface 506 outside a surface in which the foot or base of the insert fits. That is, the pointed end or tip 504 is located outside of the area of the foot of the insert when placed within the canister. In one embodiment, the opposite, pointed end 504 of the puncturing element is contained within the reservoir; that is, the length of the puncturing element is such that the puncturing tip is below the rim and does not extend above the rim. The length of the puncturing element 502 may therefore vary in some embodiments. As described above, the canister may be manufacture or formed by any means known in the art including without limitation molding, forming, shaping or any combination thereof. Thus, the puncturing element 502 and the tip 504 may be molded within the reservoir as part of the canister in one integral piece in one embodiment. In one embodiment, the reservoir may comprise a medication able to be expelled through the device as a mist as described in any of the above embodiments.

FIG. 38 is a cross section view of an insert 515 in accordance with one embodiment. In one embodiment, the nasal drug delivery device comprises an extension 508 between an exterior portion of the fluid channel 509 and the rim of the canister 500. In one embodiment, the extension 508 extends from the insert to the rim. That is, the insert comprises the extension in one embodiment. In one embodiment, the extension 508 extends from the fluid channel 509 to the rim of the canister, as described in above embodiments. In one embodiment, the extension 508 comprises a parabolic shape. As shown in FIG. 38, the insert comprises a storage compartment 510 below the extension 508. In one embodiment, the storage compartment 510 is detachably connected to a bottom surface of the extension 508. In one embodiment, the storage compartment 510 is permanently affixed to a bottom surface of the extension 508. In one embodiment, the storage compartment 510 comprises an accessible filling port 512, which extends from a top surface of the extension 508 through to the bottom surface of underside of the extension 508. The size of the filling port may vary so long as it does not exceed the boundaries of the storage compartment. In one embodiment, the size is only large enough to allow for medication to be inserted into the storage compartment. One skilled in the art, armed with this disclosure, will recognized that a needle, for example, may be used for the inserting of the filling. In one embodiment, the accessible filling port 512 comprises a seal 514, which can be placed over the accessible filling port 512 after the storage compartment is filled. In one embodiment, the seal 514 is a hermetic seal.

FIG. 39 shows a top view of an assembled canister and insert within the canister, with a view of one shape possible for the storage compartment. The device also comprises an air vent 522. In some embodiments, the air vent is located on an exterior surface of an extension so that it may readily accessed and opened by a user. In some embodiments, the puncturing tip 504 punctures both the storage compartment 510 and the vent 522 to allow the filling to escape the bottom of the storage compartment, while allowing air to enter the storage compartment through the vent. In this case, the vent would be placed on a concave section of the extension where the upper surface of the extension is lower than the length of the distance the insert is inserted into the canister to be fully seated. Alternatively, the air vent may be punctured by a secondary spike inside the canister. The exact placement of an air vent can be readily determined by one skilled in the art, having read this disclosure.

The storage compartment may comprise a filling in any form capable of insertion into the storage compartment for flowing into the reservoir due to piercing by the puncturing element. In some embodiments, the filling works in combination with a substance within the canister. In some embodiments, the filling within the storage compartment may work in combination with a liquid or powder substance within the reservoir. In some embodiments, the filling within the storage compartment is a dry solid such as powder or flakes. In such embodiments, the reservoir of the canister comprises a liquid substance adapted to substantially dissolve the dry powder. For example, in some embodiments, the filling within the storage compartment may comprise an excipient for a drug. An excipient may comprise a sugar such as mannitol or xylitol, poloxamers, and/or methylcellulose, and/or any other component that would enable a drug to go into a solution or suspension. In some embodiments, the filling comprises a medication. In some embodiments, the filling may comprise an active pharmaceutical agent in the form of a dry powder. In one embodiment, the filling within the storage compartment is a liquid. In some embodiments, the filling within the storage compartment comprises a diluent. In some embodiments, the reservoir within the storage compartment comprises a diluent. In some embodiments, the filling within the storage compartment combines with the secondary substance within the reservoir of the canister upon puncturing to form a suspension.

FIG. 40 is a cross sectional view of an assembled device 520 wherein the insert comprising an extension and an attached storage compartment is placed within the canister, wherein the fluid channel is placed over the air exit port in one embodiment. As depicted in FIG. 40, the puncturing element 502 pierces the storage compartment 510 with the puncturing tip 504. In embodiments comprising an extension wherein the storage compartment is attached to an underside or bottom surface of the extension, the piercing takes places upon assembly or insertion of the insert into the canister. One skilled in the art, armed with this disclosure, will also recognize that the length of the puncturing element 502 may be shorter with attachment to a button element that would cause the puncturing tip 504 to move up and through the storage compartment 510. Upon piercing, the filling within the storage compartment flows into the reservoir. The device may then be shaken if necessary to form a material capable of exiting the device as a mist.

Figure 41:
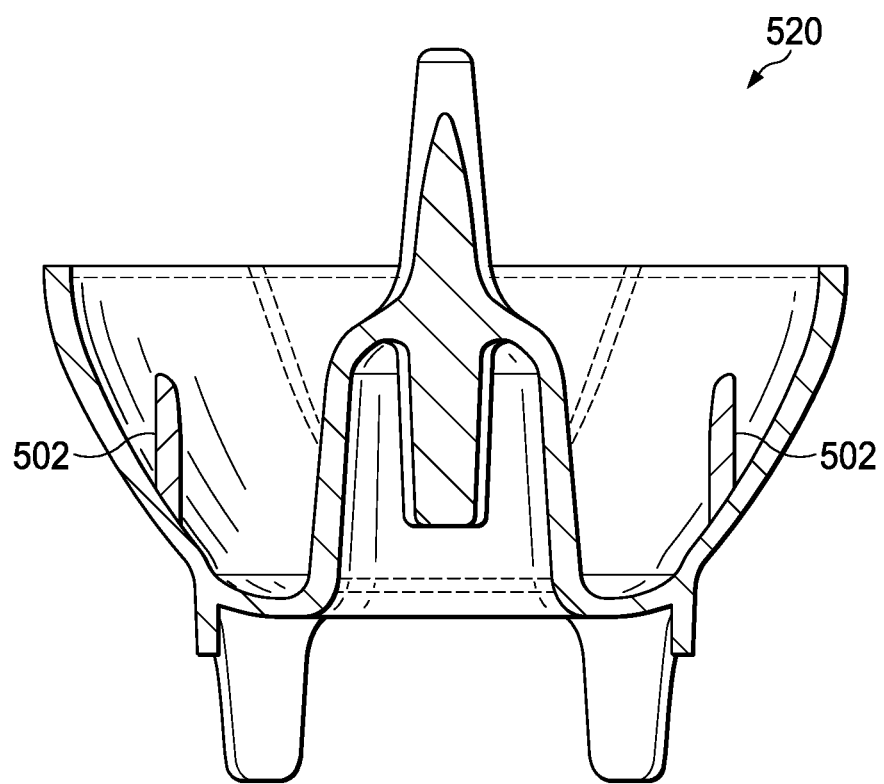

FIG. 41 depicts a cross section view of another embodiment of an assembled device 520 with insert and canister, the device comprising more than one puncturing element 502. While omitted in the Figure for clarity, the insert may also comprise an attached storage compartment as described above. In such embodiments, the shape of the storage compartment may comprise a larger percentage of the interior of the reservoir. Alternatively, the device may also comprise more than one storage compartment. For example, the device may comprise an equal number of storage compartments and puncturing elements such that each storage compartment has a corresponding puncturing element.

Figure 42:
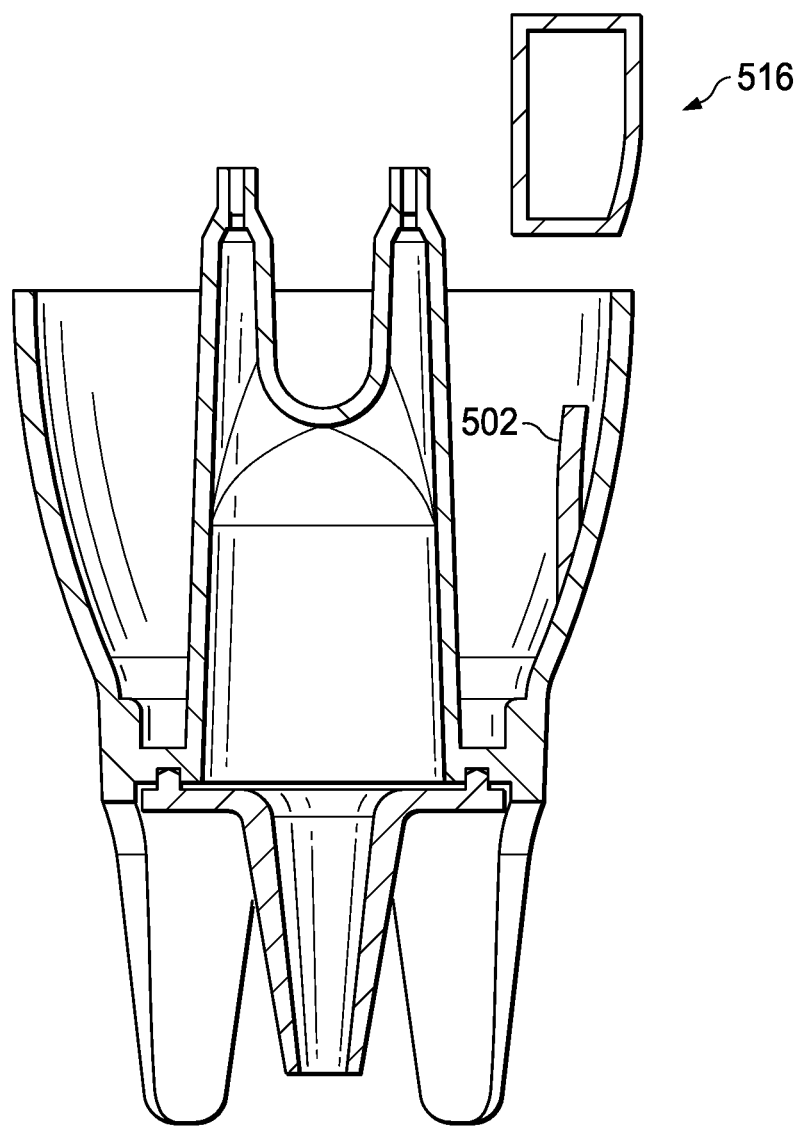

FIG. 42 depicts another embodiment of an assembled nasal drug delivery device for which an extension is absent. In such embodiments, a separate storage compartment 516 may be pierced through manual insertion by a user to fill the reservoir with a medicating or irrigating solution.

Sample medications particularly useful in the improved nasal drug delivery device may comprise any of: antibiotics including macrolides such as clarithromycin and azithromycin; glycopeptides such as vancomycin; aminoglycosides such as gentamicin or tobramycin; fluoroquinolones such as levofloxacin and ciprofloxacin; monoxycarbolic acids such as mupirocin; beta-lactams including cephalosporins such as ceftriaxone and ceftazadine; carbapenems such as meropenem and imipenem; penicillins such as tazobactam; ureidopenicillins such as piperacillin; lincosamide such as clindamycin; corticosteroids including glucocorticosteroids such as fluticasone proprionate, budesonide, mometasone fuorate, betamethasone, beclamethasone; anti-fungals including macrolide antifungals such as ampohetericin B, nystatin, azole antifungals including triazole antifungals such as fluconazole and itraconazole; leukotriene receptor antagonists such as montelukast; antihistamines such as levozeterizine and loratadine; and methylxanthines such as theophylline.

The method of the nasal drug delivery device described herein may comprise the steps of providing a canister comprising a reservoir, an air exit port and a puncturing element, the air exit port extending beyond a rim of the canister; providing an insert comprising a fluid channel, an extension between the fluid channel and the canister, and a storage compartment, wherein the fluid channel fits over the air exit port to provide a small space between an outer surface of the air exit port and an inner surface of the fluid channel; and inserting a filling into the storage compartment and a substance into the reservoir, such that a medication (or medication mixture in some embodiments) is created when the filling and substance are combined and/or mixed together. In one embodiment, the filling is a medication. In one embodiment, the substance is a medication. In one embodiment, the filling is a dry solid. In one embodiment, the substance is a dry solid. In various embodiments, the dry solid is a powder. The dry solid may comprise an active pharmaceutical agent. In one embodiment, the substance is a solution. In one embodiment, the substance is a diluent. In one embodiment, the filling is a solution.

In one embodiment, the method further comprises the step of sealing the storage compartment after the inserting step. In such embodiments, seal may comprise a hermetic seal. In one embodiment, the method further comprises the step of attaching the storage compartment to the insert prior to the inserting of the filling. In one embodiment, the storage compartment is attached to an extension of the insert. In one embodiment, the storage compartment is detachable or separate. In one embodiment, the method comprises the step of sealing together the canister and the insert. Such embodiment may comprise a permanent seal.

In one embodiment, the inserting step comprises inserting a filling through a filling port. The filling port provides access to the reservoir of the canister in some embodiments. In one embodiment, the canister comprises the filling port. In one embodiment, the insert comprises the filling port.

A number of benefits exist with the use of the aforementioned improved embodiments. By using a dry powder as the filling within the reservoir, and a liquid substance within the storage compartment, for example, a dry powder medication can be used within the reservoir and a saline solution within the storage compartment can dissolve the dry powder into a medication that can be dispensed to the user as a mist. By sealing the insert and the canister, the shelf life is thus limited only to that of the saline or the shortest use before date for the medication. With proper testing of a saline solution, the medication may comprise an extended shelf life of one to two years.

The invention illustratively disclosed herein suitably may be practiced in the absence of any element, which is not specifically disclosed herein. It should also be noted that the invention is not limited to human use, but may also be used with any number of mammals including without limitation equine, canine, feline, non-human primate, rodent, bovine, ovine, and porcine.

The description of the present invention has been presented for purposes of illustration and description, and is not intended to be exhaustive or limited to the invention in the form disclosed. Many modifications and variations will be apparent to those of ordinary skill in the art. The embodiment was chosen and described in order to best explain the principles of the invention, the practical application, and to enable others of ordinary skill in the art to understand the invention for various embodiments with various modifications as are suited to the particular use contemplated. It will be understood by one of ordinary skill in the art that numerous variations will be possible to the disclosed embodiments without going outside the scope of the invention as disclosed in the claims.

I claim:

1. An interface for a nasal drug delivery device comprising:
    a canister comprising a reservoir, an air exit port and a puncturing element on an inner surface of the canister, wherein the air exit port extends beyond a rim of the canister and the puncturing element comprising a puncturing tip positioned below the rim;
    an insert comprising a fluid channel that fits over the air exit port; and
    wherein the air exit port defines an end of a tube portion extending from a pressurized air supply source interface at an opposite end of the tube portion from the air exit port, the air supply source interface configured for receiving pressurized air from a pressurized air supply source and directing pressurized air through the air exit port to dispense a medication within the reservoir in the form of a mist.

2. The interface of claim 1 comprising an extension between the fluid channel and the canister, and a storage compartment comprising a filling, the storage compartment attached to the extension and the extension comprising an air vent on the storage compartment, wherein at least a portion of the storage compartment is formed of a material that can be penetrated by the puncturing element to release the filling into the canister to provide for the medication to be dispensed through an exit hole of the fluid channel directly to a user.

3. The interface of claim 2 wherein the filling comprises a liquid.

4. The interface of claim 2 wherein the storage compartment is permanently attached to the extension.

5. The interface of claim 2 wherein the storage compartment is detachable.

6. The interface of claim 2 wherein the storage compartment comprises an accessible filling port.

7. The interface of claim 2 wherein the storage compartment comprises a hermetic seal.

8. The interface of claim 2 wherein the fluid channel comprises a groove extending vertically along the exterior of the fluid channel to an aperture in the extension, said aperture creating a channel to the reservoir of the canister.

9. The interface of claim 1 wherein the medication is derived at least in part from a separate, detached storage compartment, said detached storage compartment pierceable by the puncturing tip to provide for filling the reservoir with the medication due to piercing.

10. The interface of claim 1 wherein the reservoir comprises a powder.

11. The interface of claim 10 wherein the storage compartment comprises a liquid capable of substantially dissolving the powder.

12. The interface of claim 1 wherein the canister and the insert are sealed together.

13. The interface of claim 1 comprising more than one storage compartment.

14. The interface of claim 1 comprising more than one puncturing element.

15. The interface of claim 1 wherein the fluid channel fits over the air exit port to provide a small space between an outer surface of the air exit port and an inner surface of the fluid channel.

16. The interface of claim 1 wherein the medication comprises an antibiotic.

17. The interface of claim 1 wherein the medication comprises a glycopeptide antibiotic.

18. The interface of claim 17 wherein the medication comprises glycopeptide vancomycin.

19. The interface of claim 1 wherein the medication comprises a corticosteroid.

20. The interface of claim 1 wherein the medication comprises an anti-fungal.

* * * * *